(12) United States Patent
Piomelli et al.

(10) Patent No.: US 10,213,416 B2
(45) Date of Patent: *Feb. 26, 2019

(54) SUBSTITUTED BENZOXAZOLONE DERIVATIVES AS ACID CERAMIDASE INHIBITORS, AND THEIR USE AS MEDICAMENTS

(71) Applicants: FONDAZIONE ISTITUTO ITALIANO DI TECNOLOGIA, Genoa (IT); THE REGENTS OF THE UNIVERSITY OF CALIFORNIA, Oakland, CA (US)

(72) Inventors: Daniele Piomelli, Irvine, CA (US); Daniela Pizzirani, Genoa (IT); Anders Bach, Valby (DK); Rita Scarpelli, Rome (IT); Laurin Melzig, Genoa (IT); Marco Mor, Ghedi (IT)

(73) Assignees: The Regents of the University of Chicago, Oakland, CA (US); Fondazione Istituto Italiano di Technologia, Genoa (IT)

( * ) Notice: Subject to any disclaimer, the term of this patent is extended or adjusted under 35 U.S.C. 154(b) by 0 days.

This patent is subject to a terminal disclaimer.

(21) Appl. No.: 15/346,457

(22) Filed: Nov. 8, 2016

(65) Prior Publication Data
US 2017/0182009 A1 Jun. 29, 2017

Related U.S. Application Data

(63) Continuation of application No. PCT/EP2015/060292, filed on May 11, 2015.

(30) Foreign Application Priority Data

May 12, 2014 (IT) .............................. MI2014A0862

(51) Int. Cl.
*A61K 31/421* (2006.01)
*C07D 263/58* (2006.01)

(52) U.S. Cl.
CPC .......... *A61K 31/421* (2013.01); *C07D 263/58* (2013.01)

(58) Field of Classification Search
None
See application file for complete search history.

(56) References Cited

U.S. PATENT DOCUMENTS 7,709,513 B2 * 5/2010 Zoller .................. C07D 263/58
514/375
2017/0182010 A1 6/2017 Piomelli et al.

FOREIGN PATENT DOCUMENTS

| EP | 1287815 A1 | 3/2003 |
|---|---|---|
| GB | 2 074 561 A | 11/1981 |
| WO | WO-2005/051891 A1 | 6/2005 |
| WO | WO-2006/050264 A1 | 5/2006 |
| WO | WO-2006/131233 A1 | 12/2006 |
| WO | WO-2007/136635 A1 | 11/2007 |
| WO | WO-2007/136635 A8 | 11/2007 |
| WO | WO-2010/054223 A1 | 5/2010 |
| WO | WO-2013/178545 A1 | 12/2013 |
| WO | WO-2013/178576 A1 | 12/2013 |
| WO | WO-2015/173168 A1 | 11/2015 |
| WO | WO-2015/173169 A1 | 11/2015 |

OTHER PUBLICATIONS

Bai, A. et al. (Mar. 1, 2009, e-published Jan. 31, 2009). "Synthesis and bioevaluation of omega-N-amino analogs of B13," *Bioorg Med Chem* 17(5):1840-1848.
Bedia, C. et al. (Nov. 2008, e-published Aug. 8, 2008). "Cytotoxicity and acid ceramidase inhibitory activity of 2-substituted aminoethanol amides," *Chem Phys Lipids* 156(1-2):33-40.
Bedia, C. et al. (Dec. 2010, e-published Sep. 24, 2010). "A simple fluorogenic method for determination of acid ceramidase activity and diagnosis of Farber disease," *J Lipid Res* 51(12):3542-3547.
Bhabak, K.P. et al. (Oct. 15, 2012, e-published Aug. 31, 2012). "Novel amide- and sulfonamide-based aromatic ethanolamines: effects of various substituents on the inhibition of acid and neutral ceramidases," *Bioorg Med Chem* 20(20):6162-6170.
Bhabak, K.P. et al. (Feb. 15, 2013, e-published Dec. 21, 2012). Effective inhibition of acid and neutral ceramidases by novel B-13 and LCL-464 analogues.
Bielawska, A. et al. (May 24, 1996). "(1S,2R)-D-erythro-2-(N-myristoylamino)-1-phenyl-1-propanol as an inhibitor of ceramidase," *J Biol Chem* 271(21):12646-12654.
Bielawska, A. et al. (Jan. 15, 2008, e-published Aug. 24, 2007). "Novel analogs of D-e-MAPP and B13. Part 2: signature effects on bioactive sphingolipids," *Bioorg Med Chem* 16(2):1032-1045.
Draper, J.M. et al. (Nov. 2011, e-published Sep. 1, 2011). "Discovery and evaluation of inhibitors of human ceramidase," *Mol Cancer Ther* 10(11):2052-2061.
International Search Report dated Jul. 20, 2015, for PCT Application No. PCT/EP2015/060291, filed on May 11, 2015, 4 pages.
International Search Report dated Jul. 20, 2015, for PCT Application No. PCT/EP2015/060292, filed on May 11, 2015, 4 pages.
Gangoiti, P. et al. (Oct. 2010, e-published Mar. 1, 2010). "Control of metabolism and signaling of simple bioactive sphingolipids: Implications in disease," *Prog Lipid Res* 49(4):316-334.
Grijalvo, S. et al. (Oct. 2006, e-published Aug. 7, 2006). "Design, synthesis and activity as acid ceramidase inhibitors of 2-oxooctanoyl and N-oleoylethanolamine analogues," *Chem Phys Lipids* 144(1):69-84.

(Continued)

*Primary Examiner* — Kamal A Saeed
(74) *Attorney, Agent, or Firm* — Anson M. Nomura; Mintz, Levin, Cohn, Ferris, Glovsky and Popeo, P.C.

(57) ABSTRACT

The present invention relates to substituted benzoxazolone derivatives as acid ceramidase inhibitors, pharmaceutical compositions containing these inhibitors and methods of inhibiting acid ceramidase for the treatment of disorders in which modulation of the levels of ceramide is clinically relevant. The invention also provides substituted benzoxazolone derivatives for use in the treatment of cancer, inflammation, pain, inflammatory pain or pulmonary diseases.

11 Claims, 2 Drawing Sheets

(56) References Cited

OTHER PUBLICATIONS

Guenadil, F. et al. (2011). "Design and synthesis of 3-acyl-2(3H)-benzoxazolone and 3-acyl-2(3H)-benzothiazolone derivatives," *Monatsh Chem* 142:67-80.

Hannun, Y.A. et al. (Feb. 2008). "Principles of bioactive lipid signalling: lessons from sphingolipids," *Nat Rev Mol Cell Biol* 9(2):139-150.

Holman, D.H. et al. (Feb. 2008, e-published Apr. 12, 2007). "Lysosomotropic acid ceramidase inhibitor induces apoptosis in prostate cancer cells," *Cancer Chemother Pharmacol* 61(2):231-242.

Mahdy, A.E. et al. (Mar. 2009, e-published Dec. 23, 2008). "Acid ceramidase upregulation in prostate cancer cells confers resistance to radiation: AC inhibition, a potential radiosensitizer," *Mol Ther* 17(3):430-438.

Mao, C. et al. (Sep. 2008, e-published Jun. 13, 2008). "Ceramidases: regulators of cellular responses mediated by ceramide, sphingosine, and sphingosine-1-phosphate," *Biochim Biophys Acta* 1781(9):424-434.

Martin, R.E. et al. (Mar. 2007). "Remote modulation of amine basicity by a phenylsulfone and a phenylthio group," *ChemMedChem* 2(3):285-287.

Morad, S.A. et al. (Jan. 2013, e-published Dec. 13, 2012). "Ceramide-orchestrated signalling in cancer cells," *Nat Rev Cancer* 13(1):51-65.

Ogretmen, B. et al. (Aug. 2004). "Biologically active sphingolipids in cancer pathogenesis and treatment," *Nat Rev Cancer* 4(8):604-616.

Patti, G.J. (Jan. 22, 2012). "Metabolomics implicates altered sphingolipids in chronic pain of neuropathic origin," *Nat Chem Biol* 8(3):232-234.

Pizzirani, D. et al. (May 2013, e-published Apr. 24, 2013). "Discovery of a new class of highly potent inhibitors of acid ceramidase: synthesis and structure-activity relationship (SAR)," *J Med Chem* 56(9):3518-3530.

Proksch, D. et al. (2011, e-published Dec. 9, 2010). "Potent inhibition of Acid ceramidase by novel B-13 analogues," *J Lipids* 2011:971618, 8 pages.

Realini, N. et al. (2013, e-published Jan. 8, 2013). "Discovery of highly potent acid ceramidase inhibitors with in vitro tumor chemosensitizing activity," *Sci Rep* 3:1035.

Saied, E.M. et al. (2014, e-published Jun. 16, 2014). "Small molecule inhibitors of ceramidases," *Cell Physiol Biochem* 34(1):197-212.

Salvemini, D. et al. (Feb. 2013, e-published Jan. 12, 2013). "Therapeutic targeting of the ceramide-to-sphingosine 1-phosphate pathway in pain," *Trends Pharmacol Sci* 34(2):11-118.

Stohandl, J. et al. (Jan. 1, 1979). "Study of Solvolysis Mechansim of Some Ureas Derived from 2-Benzoxazolone," Collection of Czechoslovak Chemical Communications, *Institute of Organic Chemistry Biochemistry* 44(6):1790-1798.

Szulc, Z.M .et al. (Jan. 15, 2008, e-published Aug. 24, 2007). "Novel analogs of D-e-MAPP and B13. Part 1: synthesis and evaluation as potential anticancer agents," *Bioorg Med Chem* 16(2):1015-1031.

Timberlake, J.W. et al. (1981). "Thiadiaziridine 1,1-Dioxides: Synthesis and Chemistry," *J Org Chem* 46(10):2082-2089.

Written Opinion dated Jul. 20, 2015, for PCT Application No. PCT/EP2015/060291, filed on May 11, 2015, 6 pages.

Written Opinion dated Jul. 20, 2015, for PCT Application No. PCT/EP2015/060292, filed on May 11, 2015, 6 pages.

Wymann, M.P. et al. (Feb. 2008). "Lipid signalling in disease," *Nat Rev Mol Cell Biol* 9(2):162-176.

Xia, Z. et al. (Feb. 2010, e-published Jan. 6, 2010). "Improved synthesis of a fluorogenic ceramidase substrate," *Bioorg Med Chem* 18(3):1003-1009.

\* cited by examiner

SUBSTITUTED BENZOXAZOLONE DERIVATIVES AS ACID CERAMIDASE INHIBITORS, AND THEIR USE AS MEDICAMENTS

CROSS-REFERENCES TO RELATED APPLICATIONS

This application is a continuation of international Patent Application No. PCT/EP2015/060292, filed May 11, 2015, which claims the benefit of IT Patent Application No. MI2014A000862 filed on May 12, 2014, all of which are incorporated herein by reference in their entirety and for all purposes.

STATEMENT AS TO RIGHTS TO INVENTIONS MADE UNDER FEDERALLY SPONSORED RESEARCH OR DEVELOPMENT

This research was made, in part, with government support under NIH Grant R01 DA12413 awarded by the National Institutes of Health; the United States Government has certain rights in the invention.

FIELD OF THE INVENTION

The present invention relates to acid ceramidase inhibitors and their use as medicaments.

In particular, the present invention concerns acid ceramidase inhibitors, pharmaceutical compositions containing them and methods for preparing these inhibitors.

The present invention also provides methods of inhibiting acid ceramidase for the treatment of disorders in which modulation of the levels of ceramide is clinically relevant, in particular for the treatment of cancer, inflammation, pain and inflammatory pain, and pulmonary diseases.

BACKGROUND OF THE INVENTION

The sphingolipids are a family of membrane lipids derived from the aliphatic amino alcohol sphingosine and its related sphingoid bases. They are present in eukaryote membranes, where they exert important structural roles in the regulation of fluidity and subdomain structure of the lipid bilayer. In addition, they have emerged as key effectors in many aspects of cell biology including inflammation, cell proliferation and migration, senescence and apoptosis [Hannun Y A, Obeid L M. *Principles of bioactive lipid signalling: lessons from sphingolipids. Nat. Rev. Mol. Cell Biol.* 2008, 9, 139-150]. Ceramide is considered a central molecule in sphingolipid catabolism. The generic term "ceramide" comprises a family of several distinct molecular species deriving from the N-acylation of sphingosine with fatty acids of different chain length, typically from 14 to 26 carbon atoms. Ceramide can be synthesized de novo from condensation of serine with palmitate, catalyzed by serine palmitoyltransferase, to form 3-keto-dihydrosphingosine. In turn, 3-keto-dihydrosphingosine is reduced to dihydrosphingosine, followed by acylation by a (dihydro)-ceramide synthase. Ceramide is formed by the desaturation of dihydroceramide. Alternatively, ceramide can be obtained by hydrolysis of sphingomyelin by sphingomyelinases. Ceramide is metabolized by ceramidases to yield sphingosine and fatty acid [Hannun Y A, Obeid L M, *Nat. Rev. Mol. Cell Biol.* 2008, 9, 139-150]. Ceramide plays an important role in a variety of cellular processes. Ceramide concentrations increase in response to cellular stress, such as DNA damage, exposure to cancer chemotherapeutic agents and ionizing radiation, and increased ceramide levels can trigger senescence and apoptosis in normal cells [Wymann M P, Schneiter R. Lipid signalling in disease. *Nat. Rev. Mol. Cell. Biol.* 2008, 9, 162-176]. Moreover, ceramide is also involved in the regulation of cancer cell growth, differentiation, senescence and apoptosis [Morad S and Cabot M. *Ceramide-orchestrated signaling in cancer cells. Nat. Rev. Cancer* 2013, 13, 51-65; Ogretmen B and Hannun Y A. *Biologically active sphingolipids in cancer pathogenesis and treatment. Nat. Rev. Cancer* 2004, 4, 604-616]. Many anticancer drugs increase ceramide levels in cells by stimulating its de novo synthesis and/or hydrolysis of sphingomyelin. For example, daunorubicin elicits ceramide production through the de novo pathway [Bose R et al., *Ceramide synthase mediates daunorubicin-induced apoptosis: an alternative mechanism for generating death signals. Cell* 1995, 82, 405-414]. De novo ceramide induction was observed in various human cancer cells after treatment with camptothecin and fludarabine [Chauvier D et al. *Ceramide involvement in homocamptothecin-and camptothecin induced cytotoxicity and apoptosis in colon HT29 cells.* Int. J. Oncol. 2002, 20, 855-863; Biswal S S et al., *Changes in ceramide and sphingomyelin following fludarabine treatment of human chronic B-cell leukemia cells. Toxicology* 2000, 154, 45-53], and with gemcitabine [Chalfant C E et al., *De novo ceramide regulates the alternative splicing of caspase 9 and Bcl-x in A549 lung adenocarcinoma cells. Dependence on protein phosphatase-1. J. Biol. Chem.* 2002, 277, 12587-12595]. In many of these studies, inhibition of de novo ceramide synthesis was found to prevent, at least in part, the cytotoxic responses to these agents, thus indicating that the de novo pathway might function as a common mediator of cell death. Therefore, increasing or sustaining the levels of ceramide in cancer cells could be envisaged as a novel therapeutic strategy to induce cancer cell death.

One approach to increase or sustain the levels of ceramide in cells is to inhibit the enzymes responsible for ceramide clearance. Enzymes that contribute to decreasing the intracellular levels of ceramide are glucosylceramide synthase, which incorporates ceramide into glucosylceramide, sphingomyelin synthase, which synthesizes sphingomyelin, and ceramidases, which hydrolyze ceramide to sphingosine and fatty acid. Currently, there are five known human ceramidases: acid ceramidase (AC), neutral ceramidase, alkaline ceramidase 1, alkaline ceramidase 2, and alkaline ceramidase 3 [Mao C, Obeid L M. *Ceramidases: regulators of cellular responses mediated by ceramide, sphingosine, and sphingosine-1-phosphate. Biochim. Biophys. Acta* 2008, 1781, 424-434]. Among them, acid ceramidase is emerging as an important enzyme in the progression of cancer and in the response to tumor therapy [Gangoiti P et al., *Control of metabolism and signaling of simple bioactive sphingolipids: Implications in disease. Prog. Lipid Res.* 2010, 49, 316-334]. Messenger RNA and protein levels of acid ceramidase are heightened in a wide variety of cancers including prostate cancer [Seelan R S et al., *Human acid ceramidase is overexpressed but not mutated in prostate cancer. Genes Chromosomes Cancer* 2000, 29, 137-146], head and neck cancer [Norris J S et al., *Combined therapeutic use of AdGFPFasL and small molecule inhibitors of ceramide metabolism in prostate and head and neck cancers: a status report. Cancer Gene Ther.* 2006, 13, 1045-1051; Elojeimy S et al., *Role of acid ceramidase in resistance to FasL: therapeutic approaches based on acid ceramidase inhibitors and FasL gene therapy. Mol. Ther.* 2007, 15, 1259-1263], and melanoma [Musumarra G et al., *A bioinformatic* approach to the identification of candidate genes for the development of new cancer diagnostics. *Biol. Chem.* 2003, 384, 321-327]. In prostate cancer, acid ceramidase expression correlates with the malignant stage of the disease [Seelan R S et al., *Human acid ceramidase is overexpressed but not mutated in prostate cancer. Genes Chromosomes Cancer* 2000, 29, 137-146]. Up-regulation of acid ceramidase has also been observed in prostate cancer cells in response to radiotherapy, and this mechanism desensitizes cells to both chemotherapy and radiotherapy. Restoration of acid ceramidase levels in radio-resistant cells by either gene silencing or inhibition of acid ceramidase activity confers radiation sensitivity to prostate cancer cells. Improvement of tumor sensitivity to ionizing radiation by inhibition of acid ceramidase has been shown in vivo in a PPC-1 xenograft model [Mandy A E et al., *Acid ceramidase upregulation in prostate cancer cells confers resistance to radiation: AC inhibition, a potential radiosensitizer. Mol. Ther.* 2009, 5 17, 430-438]. Together, these data suggest that acid ceramidase provides a growth advantage to cancer cells and contributes to the altered balance between proliferation and death eventually leading to tumor progression. Therefore, inhibition of acid ceramidase appears to be a promising strategy for cancer treatment.

The aforementioned balance between cellular proliferation and death is mainly regulated by the ceramide/sphingosine 1-phosphate S1P rheostat [Mao C, Obeid L M. *Ceramidases: regulators of cellular responses mediated by ceramide, sphingosine, and sphingosine-1-phosphate. Biochim. Biophys. Acta* 2008, 1781, 424-434]. Compelling evidences implicate this pathway as contributor to inflammatory conditions and pain of diverse etiologies [Salvemini D, Doyle T, Kress M, Nicol G. *Therapeutic targeting of the ceramide-to-sphingosine 1-phosphate pathway in pain. Trends in Pharmacological Sciences* 2013, 34(2)110-118. Patti G J, Yanes O, Shriver L, Courade J P, Tautenhahn R, Manchester M, Siuzdak G. *Metabolomics implicates altered sphingolipids in chronic pain of neuropathic pain. Nat Chem Biol* 2013, 8(3), 232-234]. Blocking acid ceramidase implies an upstream inhibition of ceramide to sphingosine 1-phosphate S1P pathway and, therefore, seems to be a promising approach to inflammatory and pain conditions treatment.

Certain methods for inhibiting ceramidase activity by compounds containing a sphingoid base, a derivative of a sphingoid base, or a salt of a sphingoid base are described in the EP1287815. Other methods for inhibiting ceramidase activity using cyclopropenyl-sphingosine derivatives are described in WO2005/051891. Still other methods for inhibiting ceramidase activity in cells using cationic ceramide derivatives are reported in WO2006/050264. Further methods for inhibiting or modulating acid ceramidase activity are disclosed in WO2007/136635 and WO2010/054223. Acid ceramidase inhibitors disclosed in the scientific and patent literature, such as B13 [Selzner M et al., *Induction of apoptotic cell death and prevention of tumor growth by ceramide analogues in metastatic human colon cancer. Cancer Res.* 2001, 61, 1233-1240], D-e-MAPP [Bielawska A et al., *(1S,2R)-D-Erythro-2-(N-myristolamino)-1-phenyl-1-propanol as an inhibitor of ceramidase. J. Biol. Chem.* 1996, 271, 12646-12654], B13 and D-MAPP analogues [Proksch et al., *Potent Inhibition of Acid Ceramidase by Novel B-13 Analogues, J. Lipids*, Article ID 971618, 8 pages; Bielawska A et al., *Novel analogs of D-e-MAPP and B13. Part 2: Signature effects on bioactive sphingolipids, Bioorg. Med. Chem.* 2008, 16, 1032-1045; Szulc Z et al., *Novel analogs of D-e-MAPP and B13. Part 1: Synthesis and evaluation as potential anticancer agents. Bioorg. Med. Chem.* 2008, 16, 1015-1031; Bhabak K P and Arenz C, *Novel amide-and sulfonamide-based aromatic ethanolamines: Effects of various substituents on the inhibition of acid and neutral ceramidases, Bioorg. Med. Chem.* 2012, 20, 6162-6170], oleoylethanolamides such as NOE and NOE analogues [Grijalvo S et al., Design, *synthesis and activity as acid ceramidase inhibitors of 2-oxooctanoyl and N-oleoylethanolamine analogues, Chem. Phys. Lipids* 2006, 144, 69-84], LCL-204 [Holman D H et al., *Lysosomotropic acid ceramidase inhibitor induces apoptosis in prostate cancer cells. Cancer Chemother. Pharmacol.* 2008, 61, 231-242,], LCL-464 and analogues [Bai A et al., *Synthesis and bioevaluation of omega-N amino analogs of B13, Bioorg. Med. Chem.* 2009, 17, 1840-1848; Bhabak K P et al., *Effective inhibition of acid and neutral ceramidases by novel B-13 and LCL-464 analogues, Bioorg. Med. Chem.* 2013, 21, 874-882], or E-tb [Bedia C et al., *Cytotoxicity and acid ceramidase inhibitory activity of 2-substituted aminoethanol amides. Chem. Phys. Lipids* 2008, 156, 33-40] are ceramide analogs that inhibit acid ceramidase activity in cell-free assays and proliferation of cancer cell lines only at high micromolar concentrations.

However, recently, two different small-molecule chemotypes were reported to be acid ceramidase inhibitors—quinolinones [Draper J M et al., *Discovery and Evaluation of Inhibitors of Human Ceramidase, Mol. Cancer Ther.* 2011, 10, 2052-2061] and 2,4-dioxopyrimidine-1-carboxamides [Realini N et al., *Discovery of highly potent acid ceramidase inhibitors with in vitro tumor chemosensitizing activity, Sci. Rep.* 2013, 3, 1035; Pizzirani D et al., *Discovery of a New Class of Highly Potent Inhibitors of Acid Ceramidase: Synthesis and Structure-Activity Relationship (SAR), J. Med. Chem.* 2013, 56, 3518-3530] that have been disclosed in WO2013/178545 and WO2013/178576.

Although both series showed effects in vitro and in vivo, they may suffer from developability issues; therefore, there is a substantial need for novel acid ceramidase inhibitors with improved potency and drug-likeness, in particular selectivity over related proteins and intrinsic stability.

Certain benzoxazolonyl ureas are disclosed in FR1469297 for their fungicide, herbicide and pesticide properties and, more in general, as disinfectants of general use. Other benzoxazolones containing the urea moiety and their compositions are disclosed in FR2478635 as fungicides.

Finally, U.S. Pat. No. 7,709,513B2 discloses benzoxazol-2-one derivatives as lipase and phospholipase inhibitors. This reference only discloses that certain benzoxazol-2-one derivatives are active in metabolic diseases such as atherosclerosis and dyslipidemia and merely claims the treatment of insulin resistance and diabetes mellitus.

SUMMARY OF THE INVENTION

One of the aims of the present invention resides in the provision of novel acid ceramidase (AC) inhibitors featuring the benzoxazolone urea scaffold. It is an additional aim of the present invention to provide alternative benzoxazolone compounds which are useful in the prevention or treatment of disorders or diseases in which the modulation of ceramide levels is clinically relevant, in particular for the treatment of cancer, inflammation, pain and inflammatory pain, and pulmonary diseases.

The present invention origins from the finding that compounds featuring the benzoxazolone urea scaffold bearing specific substituent groups on the benzoxazolone ring and on the side chain connected to the ureido moiety, as depicted in the forthcoming Formula (I), possess a remarkable pharmacological activity and found specific application in the prevention and treatment of disorders associated with increased levels of acid ceramidase protein or function.

In particular, the inventors have found that specific benzoxazolone derivatives that selectively inhibit acid ceramidase display an antiproliferative profile that makes them uniquely suitable to treat diseases characterized by abnormal cell proliferation, including but not limited to cancer, psoriasis and rheumatoid arthritis.

In a first aspect, the present invention provides a compound of Formula (I) or a pharmaceutically acceptable salt thereof

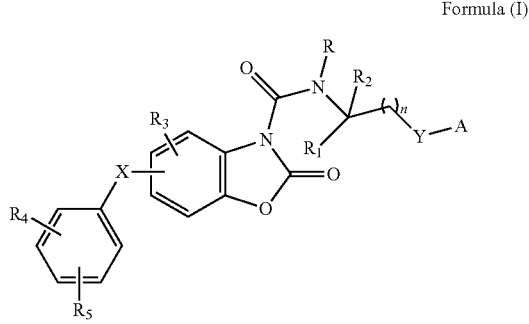

Formula (I)

wherein A, R, $R_1$, $R_2$, $R_3$, $R_4$, $R_5$, X, Y, n are as defined below or in the appended claims.

In a second aspect, the present invention provides a pharmaceutical composition comprising one or more compounds of Formula (I), as defined above or a pharmaceutically acceptable salt thereof, and pharmaceutically acceptable excipients, carriers or diluents.

In a third aspect the present invention relates to a compound of Formula (I) as a medicament, in particular for use in the treatment of a disorder associated with increased, compared with physiological or desired, levels of acid ceramidase protein or function, such as in cancer or precancerous conditions, inflammation, pain and inflammatory pain, and pulmonary diseases.

In a fourth aspect, the present invention provides a method of treatment of diseases or disorders associated with increased (relative to physiological or desired) levels of acid ceramidase protein or function, for example in subjects where acid ceramidase is overactive or over-expressed, by administering a therapeutically effective amount of a compound of Formula (I), as defined above or a pharmaceutically acceptable salt thereof, according to the invention.

In some embodiments, the compounds of Formula (I) and their pharmaceutical compositions and methods of administering them, are useful in treating diseases or disorders involving abnormal cell proliferation and/or dysfunctional sphingolipid signal transduction. These diseases and disorders include, but are not limited to, primary and metastatic neoplastic diseases.

In a fifth aspect, the present invention provides methods for preparing the compounds of Formula (I), as defined above, through a process consisting of suitable synthetic transformations.

In a sixth aspect, the present invention provides biological in vitro methods for testing the compounds of Formula (I), therefore assessing their therapeutic potential.

DETAILED DESCRIPTION OF THE INVENTION

Figure 1:
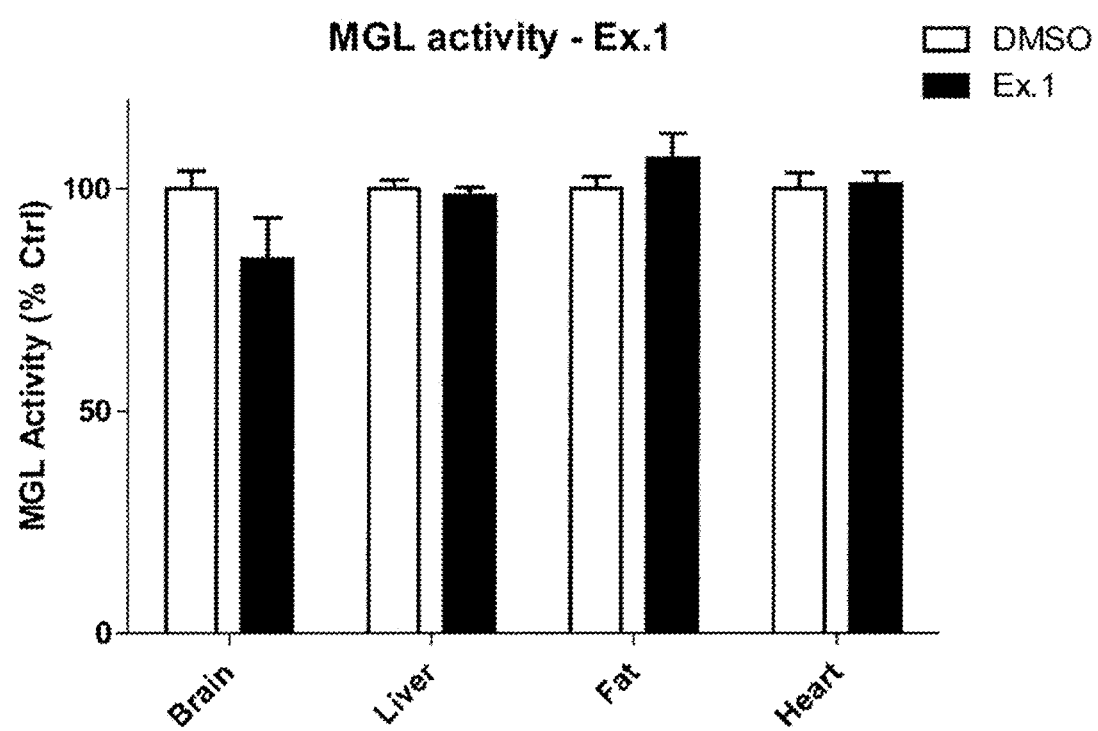
FIG. 1 illustrates the lack of effect of the compound of Example 1 on mouse MAG-hydrolysing activity ex vivo.

The inventors have discovered that specific compounds bearing a benzoxazolone urea scaffold are effective in the treatments of disorders associated with altered ceramide levels, in particular for the treatment of cancer, inflammation, pain and inflammatory pain, and pulmonary diseases.

Accordingly, the compounds of the invention are useful in the treatment of diseases associated with altered levels of ceramide in certain body compartments of a subject.

I. Compounds of Formula (I)

In accordance with a first aspect, the present invention provides a compound of Formula (I) or a pharmaceutically acceptable salt thereof

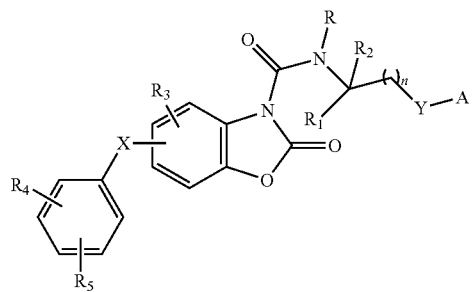

Formula (I)

wherein:

X is a bond, CO, CH(OH) or $CH_2$; X can be attached to any position of the ring to which it is connected;

R, $R_1$ and $R_2$ are independently hydrogen, linear or branched $C_{1-6}$ alkyl;

n is an integer from 1 to 6;

A is a linear or branched $C_{1-9}$ alkyl, $C_{2-9}$ alkenyl or $C_{2-9}$ alkynyl group or a group:

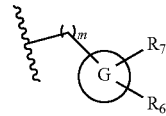

wherein:

m is 0 or an integer from 1 to 6;

G is a 3-10 membered saturated or unsaturated, aromatic or heteroaromatic, single or fused ring comprising up to three heteroatoms selected from N, O, S; and $R_6$ and $R_7$ are as defined below;

$R_3$ is hydrogen, halogen, linear or branched $C_{1-6}$ alkyl, $C_{1-6}$ alkoxy or OH; $R_3$ can be attached to any position of the ring to which it is connected;

$R_4$ and $R_5$ are independently selected from the group consisting of hydrogen, halogen, linear or branched $C_{1-6}$ alkyl, $C_{1-6}$ alkoxy, hydroxy $C_{1-6}$ alkyl, OH, CN, $NO_2$, fluoro $C_{1-6}$ alkyl, fluoro $C_{1-6}$ alkoxy, $COOR_8$, $CONR_9R_{10}$, $SO_2NR_9R_{10}$, $SO_2R_{11}$;

$R_6$ and $R_7$ are independently selected from the group consisting of hydrogen, halogen, linear or branched $C_{1-6}$ alkyl, optionally substituted $C_{3-6}$ cycloalkyl, $C_{1-6}$ alkoxy, hydroxy $C_{1-6}$ alkyl, OH, CN, $NO_2$, fluoro $C_{1-6}$ alkyl, fluoro $C_{1-6}$ alkoxy, optionally substituted aryl or heteroaryl, $COOR_8$, $CONR_9R_{10}$, $SO_2NR_9R_{10}$, $SO_2R_{11}$;

$R_4$, $R_5$, $R_6$ and $R_7$ can be attached to any position of the ring to which they are connected;

Y is a bond or a heteroatom selected from the group consisting of O, S, SO, $SO_2$ or $NR_{12}$;

$R_8$, $R_9$, $R_{10}$, $R_{11}$ and $R_{12}$ are independently selected from the group consisting of hydrogen, linear or branched $C_{1-6}$ alkyl;

provided that when Y is a bond, both the following conditions are met:

A is a group

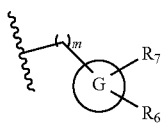

and n+m is ≥4.

In certain embodiments compounds of Formula (I) as defined above are provided wherein:

X is a bond, CO, CH(OH);

R is hydrogen;

$R_1$ and $R_2$ are independently hydrogen, linear or branched $C_{1-6}$ alkyl, preferably methyl;

n is an integer from 1 to 6;

A is a linear $C_{1-6}$ alkyl or a group

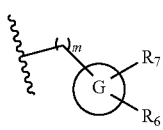

m is an integer from 1 to 6;

G is an aryl selected from naphthyl or phenyl $(C_3-C_{10})$cycloalkyl, a heteroaryl which is pyridyl, thiophenyl, pyrimidinyl, furyl, indolyl;

$R_3$ is hydrogen, halogen, preferably chlorine or fluorine;

$R_4$ and $R_5$ are independently selected from the group consisting of hydrogen, halogen preferably F, linear or branched $C_{1-6}$ alkyl preferably $C_{1-3}$ alkyl, $C_{1-6}$ alkoxy preferably MeO and EtO, OH, CN, $NO_2$, $CF_3$, hydroxy $C_{1-6}$ alkyl;

$R_6$ and $R_7$ are independently selected from the group consisting of hydrogen, halogen, linear or branched $C_{1-6}$ alkyl, $C_{1-6}$ alkoxy, preferably MeO and EtO, hydroxy $C_{1-6}$ alkyl, OH, CN, $NO_2$, $CF_3$; preferably both $R_6$ and $R_7$ are hydrogen;

Y is a bond or a heteroatom selected from the group consisting of O, S, SO, $SO_2$;

with the proviso that when Y is a bond, A is a group

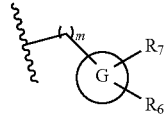

and n+m is ≥4.

II. Subset of Compounds of Formula (Ia)

In accordance with certain embodiments of the invention, a subset of the compounds of Formula (I) is provided, endowed with high inhibitory activity of acid ceramidase enzyme, having the Formula (Ia)

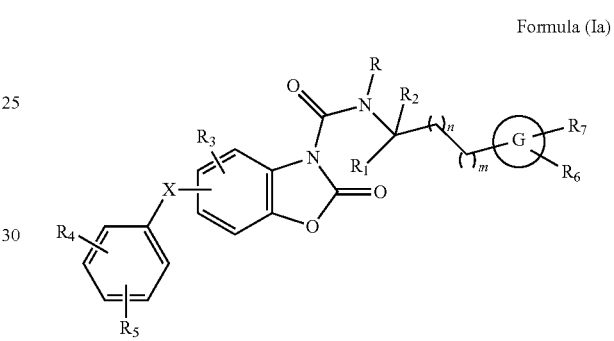

Formula (Ia)

wherein:

X, G, R, $R_1$, $R_2$, $R_3$, $R_4$, $R_5$, $R_6$, $R_7$, n and m are as defined in Formula (I) with the proviso that n+m is ≥4.

Preferred compounds of the subset of compounds of Formula (Ia) are those in which:

X is a bond, CO, CH(OH); X can be attached to any position of the ring to which it is connected;

R is hydrogen;

$R_1$ and $R_2$ are independently hydrogen or Me;

n is an integer from 2 to 4;

m is an integer from 2 to 4;

G is phenyl, thiophenyl, pyridyl, naphthyl or $C_{3-7}$ cycloalkyl and preferably is cyclohexyl;

$R_3$ is hydrogen, chlorine; $R_3$ can be attached to any position of the ring to which it is connected;

$R_4$ is hydrogen;

$R_5$ is independently selected from the group consisting of halogen, preferably F or Cl, Me, Et, MeO, EtO, OH, CN, $NO_2$, $CF_3$;

$R_6$ and $R_7$ are independently selected from the group consisting of hydrogen, halogen, Me, Et, MeO, EtO, OH, CN, $NO_2$, $CF_3$, preferably both $R_6$ and $R_7$ are hydrogen;

$R_4$, $R_5$, $R_6$ and $R_7$ can be attached to any position of the ring to which they are connected; with the proviso that n+m is ≥4.

III. Subset of Compounds of Formula (Ib)

In accordance with certain embodiments of the invention, a subset of compounds of Formula (Ib) is provided, in which Y is a heteroatom selected from the group consisting of O, S, SO, $SO_2$ or $NR_{12}$ as defined in Formula (I);

A, X, G, R, $R_1$, $R_2$, $R_3$, $R_4$, $R_5$, $R_6$, $R_7$, n and m are as defined in Formula (I).

Preferred compounds of the compounds of the subset of Formula (Ib) are those in which:

X is a bond, CO, CH(OH); X can be attached to any position of the ring to which it is connected;

R is hydrogen;

$R_1$ and $R_2$ are independently hydrogen or Me;

n is an integer from 1 to 4;

m is 0 or an integer from 1 to 4;

G is phenyl, thiophenyl, pyridyl, naphthyl or $C_{3-7}$ cycloalkyl, preferably cyclohexyl;

$R_3$ is hydrogen, chlorine; $R_3$ can be attached to any position of the ring to which it is connected;

$R_4$ is hydrogen;

$R_5$ is independently selected from the group consisting of halogen, preferably F or Cl, Me, Et, MeO, EtO, OH, CN, $NO_2$, $CF_3$;

$R_6$ and $R_7$ are independently selected from the group consisting of hydrogen, halogen, Me, Et, MeO, EtO, OH, CN, $NO_2$, $CF_3$, preferably both $R_6$ and $R_7$ are hydrogen;

$R_4$, $R_5$, $R_6$ and $R_7$ can be attached to any position of the ring to which they are connected.

IV. Definitions

All technical and scientific terms used herein have the same meaning as commonly understood by a person of ordinary skill in the art, unless otherwise defined. The following terms, used in the specification and claims of this application, have the meaning specified hereunder, unless otherwise defined.

The term "alkyl", as used herein, indicates a saturated aliphatic hydrocarbon radical, including straight chain and branched chain radicals of 1 to 6 carbon atoms. Non-limiting examples of alkyl are, for instance, methyl, ethyl, propyl, isopropyl, n-butyl, iso-butyl, tert-butyl, n-amyl, iso-amyl, n-hexyl, and the like. The term Me, as used herein, means a methyl group, similarly the term Et means the ethyl group.

The term "alkenyl", as used herein, indicates an alkyl group, as defined herein, consisting of at least two carbon atoms and containing at least one carbon-carbon double bond. Representative examples include, but are not limited to, ethenyl, 1-propenyl, 2-propenyl, 1- or 2-butenyl, and the like.

The term "alkynyl", as used herein, indicates an alkyl group, as defined herein, consisting of at least two carbon atoms and containing at least one carbon-carbon triple bond. Representative examples include, but are not limited to, ethynyl, 1-propynyl, 2-propynyl, 1- or 2-butynyl, and the like.

The term "cycloalkyl", as used herein, indicates a 3- to 7-membered all-carbon monocyclic ring, which may contain one or more double bonds but does not have a completely conjugated pi-electron system. Examples of cycloalkyl groups include, without limitation, cyclopropane, cyclobutane, cyclopentane, cyclopentene, cyclohexane, cyclohexene, cyclohexadiene, and cycloheptane.

The term "aryl", as used herein, indicates a hydrocarbon consisting of a mono-, bi- or tricyclic ring system, wherein the rings are fused together or linked to each other covalently and at least one of the carbocyclic rings is aromatic. The term "aryl" means a cyclic aromatic such as a 6-membered hydrocarbon, a two six-membered fused hydrocarbon, and a two six-membered hydrocarbon covalently bonded.

Examples of aryl groups include phenyl, alpha- or beta-naphthyl, 9,10-dihydroanthracenyl, indanyl, fluorenyl, biphenyl and the like.

The term "heteroaryl", as used herein, indicates a mono-, bi- or tricyclic ring system containing from one to four heteroatoms selected from nitrogen, oxygen and sulphur, wherein the rings are fused together or linked to each other covalently and at least one of the rings is aromatic. Examples of heteroaryl groups include pyrrolyl, furyl, thiophenyl, imidazolyl, pyrazolyl, oxazolyl, isoxazolyl, thiazolyl, isothiazolyl, indolyl, benzofuranyl, benzothiophenyl, benzimidazolyl, benzopyrazolyl, benzoxazolyl, benzoisoxazolyl, benzothiazolyl, benzoisothiazolyl, triazolyl, oxadiazolyl, tetrazolyl, pyridyl, pyrazinyl, pyrimidinyl, pyridazinyl, quinolinyl, isoquinolinyl, quinazolinyl, quinoxalinyl.

The terms "heterocyclyl" or "heterocyclic ring", as used herein mean a 3- to 7-membered, saturated or partially unsaturated carbocyclic ring wherein one or more carbon atoms are independently replaced by nitrogen, oxygen or sulfur. The heteroatom nitrogen and sulfur are optionally oxidized, and the nitrogen atom(s) are optionally quaternized. Examples of heterocyclyl groups include, for instance, radicals derived from oxirane, aziridine, oxetane, azetidine, tetrahydrofuran, dihydrofuran, tetrahydrothiophene, dihydrothiophene, pyrrolidine, dihydropyrrole, pyran, dihydropyran, tetrahydropyran, tetrahydrothiopyran, piperidine, pyrazoline, oxazoline, isoxazolidine, isoxazoline, thiazolidine, thiazoline, isothiazoline, dioxane, piperazine, morpholine, thiomorpholine, examethyleneimine, homopiperazine, and the like.

The term "aromatic" refers to a moiety wherein the constituent atoms make up an unsaturated ring system, all atoms in the ring system are $sp^2$ hybridized and the total number of pi electrons is equal to 4n+2, wherein n is an integer.

Any of the above mentioned alkyl, alkenyl, alkynyl, cycloalkyl, aryl, heteroaryl, heterocyclyl or heterocyclic ring group may be unsubstituted or substituted by one or more substituents.

Unless otherwise indicated, the term "substituted" as used herein means that one or more hydrogen atoms of the above mentioned groups are replaced with another atom or functional group including, by way of example, alkyl, substituted alkyl, aryl, substituted aryl, arylalkyl, alkoxy, cycloalkyloxy, aryloxy, arylalkyloxy, hydroxy, heteroaryl, heteroaryloxy, heterocyclyloxy, trifluoromethyl, trifluoromethoxy, carboxy, acyl, aroyl, heteroaroyl, halogen, nitro, cyano, alkoxycarbonyl, aryloxycarbonyl, aralkyloxycarbonyl, cycloalkyloxycarbonyl, heteroaryloxycarbonyl, acyloxy, alkylthio, arylthio, alkylsulfinyl, arylsulfinyl, alkylsulfonyl, arylsulfonyl, —O-aroyl, —O-heteroaroyl, oxo (=O), —C(=O)—$NR^hR^k$, and —$NR^pR^q$, wherein each of $R^h$, $R^k$, $R^p$, and $R^q$ independently represents hydrogen, unsubstituted or substituted alkyl, unsubstituted or substituted cycloalkyl, unsubstituted or substituted aryl, unsubstituted or substituted arylalkyl, unsubstituted or substituted heteroaryl, unsubstituted or substituted heterocyclyl, acyl, aroyl, heteroaroyl, and when $R^h$ and $R^k$, or $R^p$ and $R^q$ are taken together with the nitrogen atom to which they are bound, the group —$NR^hR^k$ or the group $NR^pR^q$ represent a heterocyclyl residue and wherein the terms alkyl, cycloalkyl, aryl, heteroaryl, heterocyclyl are as above defined.

The term "alkoxy", as used herein, means an unsubstituted or substituted alkyl chain linked to the remainder of the molecule through an oxygen atom. Examples of alkoxy include, but are not limited to, methoxy, ethoxy, propyloxy, isopropyloxy, benzyloxy and the like. The term MeO means methoxy, the term EtO means ethoxy.

The term "halogen", as used herein, indicates fluorine (F), chlorine (Cl), bromine (Br) or iodine (I).

The term "hydroxy" means a —OH radical.

The term "trifluoromethyl" means a —CF$_3$ radical.

The term "trifluoromethoxy" means a —OCF$_3$ radical.

Examples of compounds of the invention, as reported in the following Table 1, are:

6-(4-fluorophenyl)-2-oxo-N-(5-phenylpentyl)-1,3-benzoxazole-3-carboxamide 6-(2-fluorophenyl)-2-oxo-N-(5-phenylpentyl)-1,3-benzoxazole-3-carboxamide 2-oxo-N-(6-phenylhexyl)-5-[4-(trifluoromethyl)phenyl]-1,3-benzoxazole-3-carboxamide 7-(4-fluorophenyl)-2-oxo-N-(6-phenylhexyl)-1,3-benzoxazole-3-carboxamide 7-(4-methoxyphenyl)-2-oxo-N-(5-phenylpentyl)-1,3-benzoxazole-3-carboxamide 6-(4-methoxybenzoyl)-2-oxo-N-(5-phenylpentyl)-1,3-benzoxazole-3-carboxamide (±)-6-[hydroxy-(4-methoxyphenyl)methyl]-2-oxo-N-(5-phenylpentyl)-1,3-benzoxazole-3-carboxamide 5-(4-methoxybenzoyl)-2-oxo-N-(6-phenylhexyl)-1,3-benzoxazole-3-carboxamide 7-(4-fluorobenzoyl)-2-oxo-N-(5-phenylpentyl)-1,3-benzoxazole-3-carboxamide N-(1,1-dimethyl-5-phenyl-pentyl)-7-(4-methoxyphenyl)-2-oxo-1,3-benzoxazole-3-carboxamide N-(1,1-dimethyl-5-phenyl-pentyl)-6-(4-fluorophenyl)-2-oxo-1,3-benzoxazole-3-carboxamide (±)-6-(4-fluorophenyl)-N-(1-methyl-5-phenyl-pentyl)-2-oxo-1,3-benzoxazole-3-carboxamide N-(3-butoxypropyl)-6-(4-fluorophenyl)-2-oxo-1,3-benzoxazole-3-carboxamide 5-chloro-7-(4-fluorophenyl)-2-oxo-N-(5-phenylpentyl)-1,3-benzoxazole-3-carboxamide 5-(4-fluorophenyl)-2-oxo-N-(4-phenylsulfanylbutyl)-1,3-benzoxazole-3-carboxamide N-[4-(benzenesulfonyl)butyl]-5-(4-fluorophenyl)-2-oxo-1,3-benzoxazole-3-carboxamide (±)-N-[4-(benzenesulfinyl)butyl]-6-(4-fluorophenyl)-2-oxo-1,3-benzoxazole-3-carboxamide Applying the synthetic procedures reported below, the following compounds can be prepared:

6-(4-chlorobenzoyl)-N-[5-(4-fluorophenyl)pentyl]-2-oxo-1,3-benzoxazole-3-carboxamide 6-(4-fluorobenzoyl)-2-oxo-N-[5-(p-tolyl)pentyl]-1,3-benzoxazole-3-carboxamide N-[5-(4-fluorophenyl)pentyl]-6-(4-methoxybenzoyl)-2-oxo-1,3-benzoxazole-3-carboxamide 6-(4-chlorobenzoyl)-N-[5-(2-naphthyl)pentyl]-2-oxo-1,3-benzoxazole-3-carboxamide 6-(4-chlorobenzoyl)-2-oxo-N-[5-(2-thienyl)pentyl]-1,3-benzoxazole-3-carboxamide 6-(4-chlorobenzoyl)-N-(5-cyclohexylpentyl)-2-oxo-1,3-benzoxazole-3-carboxamide N-(5-cyclohexylpentyl)-6-(4-fluorophenyl)-2-oxo-1,3-benzoxazole-3-carboxamide 6-(4-chlorobenzoyl)-2-oxo-N-(5-phenylpentyl)-1,3-benzoxazole-3-carboxamide 6-(4-chlorobenzoyl)-2-oxo-N-(5-phenylhexyl)-1,3-benzoxazole-3-carboxamide 7-(4-chlorobenzoyl)-2-oxo-N-(5-phenylpentyl)-1,3-benzoxazole-3-carboxamide 7-(4-methoxybenzoyl)-2-oxo-N-(5-phenylpentyl)-1,3-benzoxazole-3-carboxamide 6-(3-fluorobenzoyl)-2-oxo-N-(5-phenylpentyl)-1,3-benzoxazole-3-carboxamide 6-(2-fluorobenzoyl)-2-oxo-N-(5-phenylpentyl)-1,3-benzoxazole-3-carboxamide (±)-6-(4-chlorobenzoyl)-N-[1-methyl-5-phenyl-pentyl]-2-oxo-1,3-benzoxazole-3-carboxamide (±)-6-[(4-chlorophenyl)-hydroxy-methyl]-2-oxo-N-(5-phenylpentyl)-1,3-benzoxazole-3-carboxamide (±)-6-[(4-fluorophenyl)-hydroxy-methyl]-2-oxo-N-(5-phenylpentyl)-1,3-benzoxazole-3-carboxamide 5-chloro-7-(4-chlorobenzoyl)-2-oxo-N-(5-phenylpentyl)-1,3-benzoxazole-3-carboxamide 6-(4-chloro-3-fluoro-benzoyl)-2-oxo-N-(5-phenylpentyl)-1,3-benzoxazole-3-carboxamide 5-(3,4-difluorophenyl)-2-oxo-N-(5-phenylpentyl)-1,3-benzoxazole-3-carboxamide 6-(3,4-difluorophenyl)-2-oxo-N-(5-phenylpentyl)-1,3-benzoxazole-3-carboxamide N-(3-butoxypropyl)-6-(4-chlorobenzoyl)-2-oxo-1,3-benzoxazole-3-carboxamide N-(3-butylsulfanylpropyl)-6-(4-chlorobenzoyl)-2-oxo-1,3-benzoxazole-3-carboxamide N-(3-butylsulfanylpropyl)-6-(4-fluorophenyl)-2-oxo-1,3-benzoxazole-3-carboxamide N-(3-benzyloxypropyl)-6-(4-chlorobenzoyl)-2-oxo-1,3-benzoxazole-3-carboxamide N-(3-benzyloxypropyl)-5-(4-fluorophenyl)-2-oxo-1,3-benzoxazole-3-carboxamide N-(3-benzylsulfanylpropyl)-6-(4-chlorobenzoyl)-2-oxo-1,3-benzoxazole-3-carboxamide N-(3-benzylsulfanylpropyl)-5-(4-fluorophenyl)-2-oxo-1,3-benzoxazole-3-carboxamide N-(4-benzyloxybutyl)-6-(4-chlorobenzoyl)-2-oxo-1,3-benzoxazole-3-carboxamide N-(4-benzylsulfanylbutyl)-5-(4-fluorophenyl)-2-oxo-1,3-benzoxazole-3-carboxamide N-(4-benzyloxybutyl)-5-(4-fluorophenyl)-2-oxo-1,3-benzoxazole-3-carboxamide.

V. Methods for Preparing Compounds of Formula (I), (Ia), (Ib)

In another aspect, the present invention also provides methods for preparing the compounds of Formula (I), (Ia), (Ib) as defined above, through a process consisting of suitable synthetic transformations reported, for instance, in Michael Smith, Jerry March—*March's Advanced Organic Chemistry: reactions mechanisms and structure*—6th Edition, John Wiley & Sons Inc., 2007, which is herein incorporated as reference. It is well known to one of ordinary skill in the art that transformation of a chemical function into another may require that one or more reactive centers in the compound containing this function be protected in order to avoid undesired side reactions. Protection of such reactive centers, and subsequent de-protection at the end of the synthetic transformations, can be accomplished following standard procedures described, for instance, in Theodora W. Green and Peter G. M. Wuts—*Protective Groups in Organic Synthesis*, Fourth Edition, John Wiley & Sons Inc., 2006, which is herein incorporated as reference.

In one embodiment, a compound of Formula (I), (Ia), (Ib) can be obtained by application of the chemical transformations reported in Scheme 1 described below.

Synthesis of Compounds of Formula (I), (Ia), (Ib):

Scheme 1

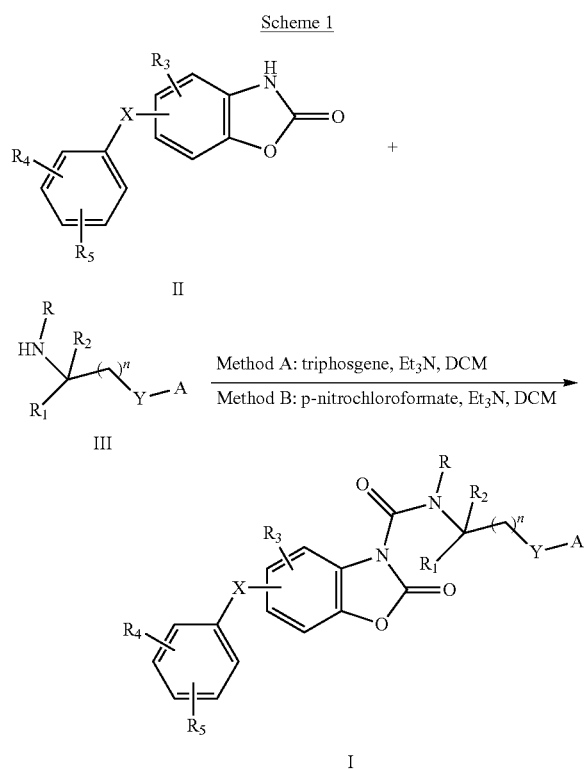

Synthesis of Compounds of Formula (II):

Scheme 2a

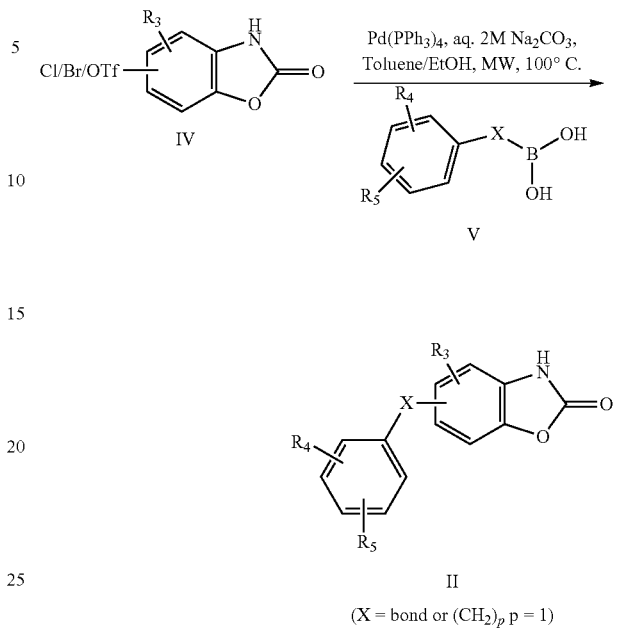

Compounds of Formula (I), (Ia), (Ib) can be obtained by two main methodologies, herein described as Method A and Method B (Scheme 1). Optionally substituted benzoxazol-2-ones of Formula II, or salts thereof, wherein $R_3$, $R_4$, $R_5$ and X are as defined above, can react with amines of Formula III, or salts thereof, wherein A, R, $R_1$, $R_2$, Y and n are as defined above, upon activation of the nitrogen of benzoxazol-2-one II with triphosgene (Method A) or p-nitrochloroformate (Method B) in dichloromethane in the presence of triethylamine. Similar to Method A and B, a compound of Formula (I), (Ia), (Ib), as defined above, can be prepared by treating a compound of Formula II (as defined in Scheme 1, Method A-B) with an activating agent such as phosgene, ethyl chloroformate, tert-butyl dicarbonate, 1,1'-carbonyldiimidazole, and the like, and subsequent reaction with an amine of Formula III, as defined above. Such reaction is carried out in a so-called "one-pot" procedure, in a suitable solvent such as dichloromethane, chloroform, acetonitrile, tetrahydrofuran, pyridine, or mixtures thereof, and in the presence of a suitable base such as triethylamine, diisopropylethylamine, or pyridine, at a temperature ranging from −10° C. to 40° C., and for a period of time from 15 min to 72 h.

Synthesis of Compounds of Formula (II):

Compounds of Formula II, where $R_3$, $R_4$, $R_5$ and X are as defined in Formula (I), (Ia), (Ib), can be prepared starting from compounds of Formula IV in one or more synthetic steps, according to standard synthetic methods as reported, for instance, in Michael Smith, Jerry March—*March's Advanced Organic Chemistry: reaction mechanisms and structure*—6$^{th}$ Edition, John Wiley & Sons Inc., 2007.

In certain embodiments, compounds of Formula II, where X is a bond or a group $(CH_2)_p$ with p equal to 1, can be obtained by a metal-catalyzed cross coupling reaction between a compound of Formula IV (i.e. the benzoxazol-2-one building block substituted with a halogen such as chlorine, bromine, iodine or with a triflate group), and boronic acids of Formula V, as exemplified using the Suzuki-Miyaura reaction (Scheme 2a). Boronic esters and organotrifluoroborate salts may be used instead of boronic acids. Boronic acids of Formula V, as defined above, are either commercially available or can be prepared from suitable precursors, as known to a person skilled in the art, according to standard synthetic methods as reported, for instance, in Norio Miyaura and Akira Suzuki, *Palladium-Catalyzed Cross-Coupling Reactions of Organoboron Compounds. Chemical Review* 1995, 95, 2457-2483, or in Michael Smith, Jerry March—*March's Advanced Organic Chemistry: reaction mechanisms and structure*—6$^{th}$ Edition, John Wiley & Sons Inc., 2007, and references cited therein, which are incorporated herein as references.

Scheme 2b

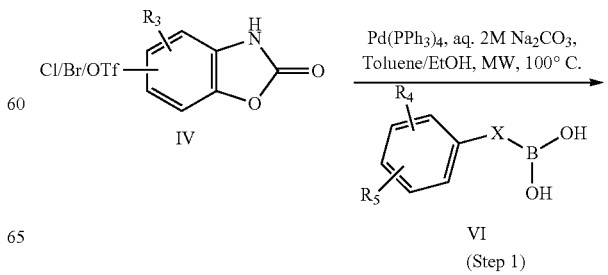

(Step 1)

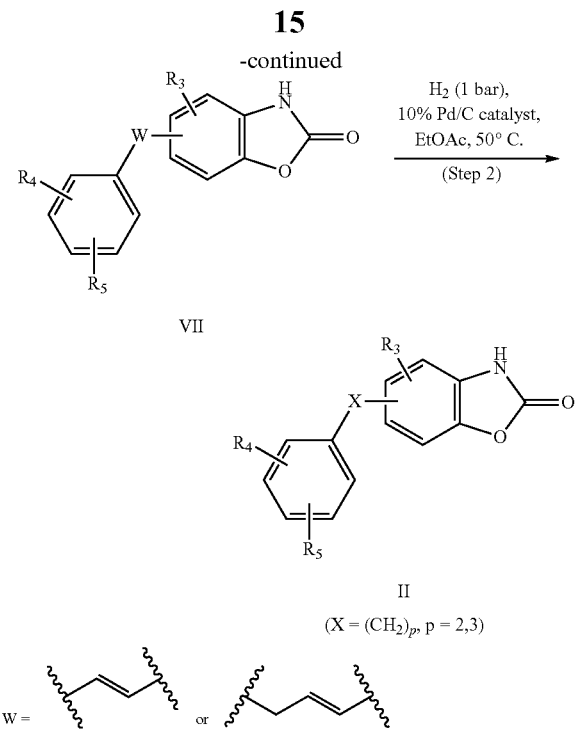

In certain embodiments, compounds of Formula II, where X is a group $(CH_2)_p$ with p equal to 2 or 3, can be prepared by coupling of compounds of Formula IV to the appropriate vinyl boronic acids of Formula VI under Suzuki-Miyaura reaction conditions (Scheme 2b, Step 1). Hydrogenation of the alkenylic double bond of compounds of Formula VII can afford the corresponding benzoxazol-2-ones of Formula II (Scheme 2b, Step 2).

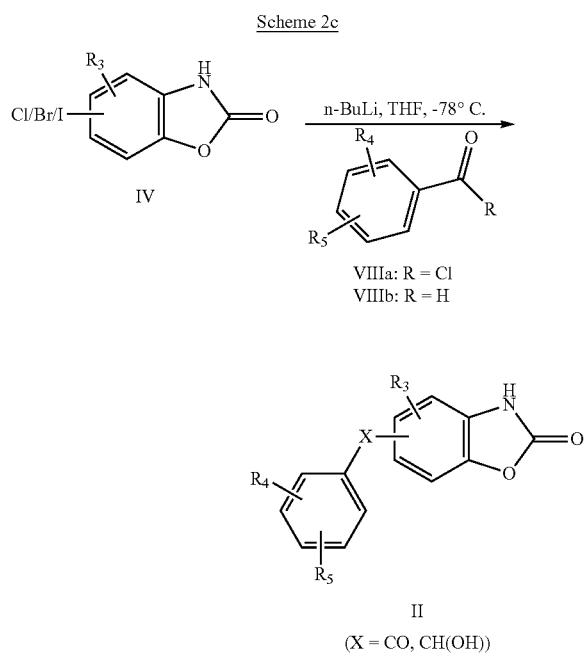

In certain embodiments, benzoxazol-2-ones of Formula II, where X is CO or CH(OH), can be obtained by metal-halogen exchange reaction, followed by addition of appropriate acyl chlorides of Formula VIIIa or aldehydes of Formula VIIIb, to form the corresponding aryl ketones or secondary alcohols, respectively, as exemplified in Scheme 2c. N-protected compounds of Formula IV can also be used in the reaction and, upon cleavage of the protecting group, can afford the desired compounds of Formula II. Suitable protecting groups, stable under basic reaction conditions, such as benzyl bromide, p-methoxybenzyl bromide and the like, can be used as known to one of ordinary skill in the art of transformation of a chemical function into another. Besides n-butyllithium, other lithium reagents such as tert-butyllithium, or Grignard reagents, such as i-propyl magnesium chloride or bromide, and the like, can be used in the reaction as known to a person skilled in the art, according to standard synthetic methods as reported, for instance in Wakefield, B. J. *The Chemistry of Organolithium Compounds—Pergamon,* 1974 or in Michael Smith, Jerry March—*March's Advanced Organic Chemistry: reaction mechanisms and structure*—6$^{th}$ Edition, John Wiley & Sons Inc., 2007, and references cited therein, which are incorporated herein as references. Acyl chlorides of Formula VIIIa and aldehydes of Formula VIIIb are either commercially available or can be prepared from the corresponding carboxylic acids following standard synthetic methods, as known to a person of ordinary skills in the art.

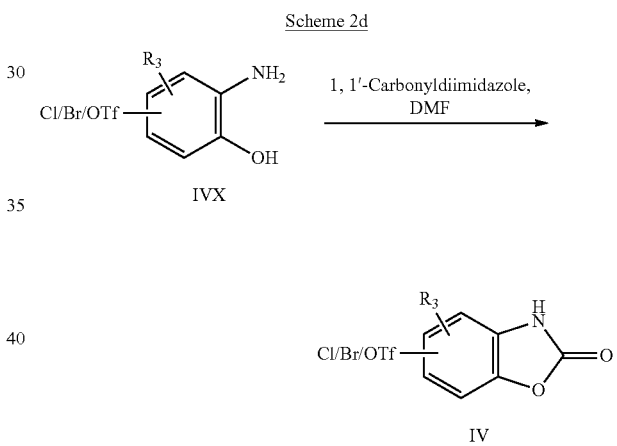

Benzoxazol-2-ones of Formula IV are commercially available or can be obtained, according to Scheme 2d, from the appropriate 2-aminophenol of Formula IX by an intramolecular cyclization reaction in the presence of 1,1'-carbonyldiimidazole, as described in literature (Nachman R J, *J. Heterocyclic Chem.*, 1982, 19, 1545-1547; Moon J-K et al., *J. Agric. Food Chem.* 2010, 58, 12357-12365), which is incorporated herein as reference. Also, other reagents can be used instead of 1,1'-carbonyldiimidazole, e.g. urea, di-2-pyridyl carbonate, phosgene, or triphosgene.

Synthesis of Compounds of Formula (III):

Compounds of Formula III, where A, $R_1$, $R_2$, Y and n are as defined in Formula (I), (Ia), (Ib), are either commercially available or can be prepared according to standard synthetic methods as reported, for instance, in Michael Smith, Jerry March—*March's Advanced Organic Chemistry: reaction mechanisms and structure*—6$^{th}$ Edition, John Wiley & Sons Inc., 2007.

Scheme 3a

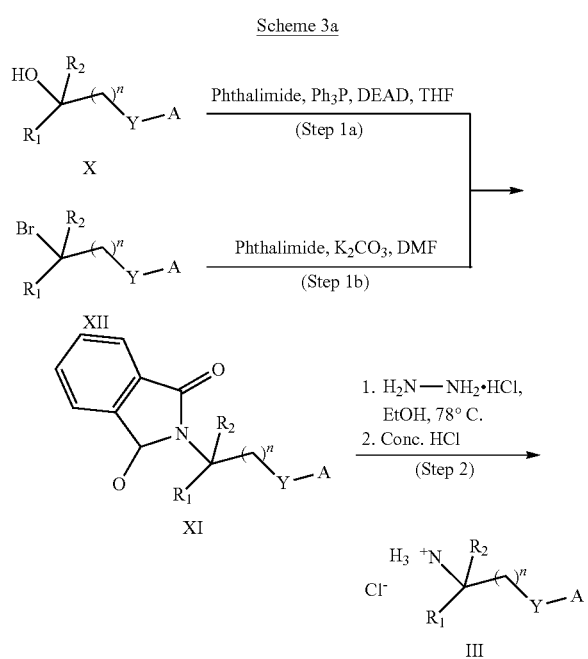

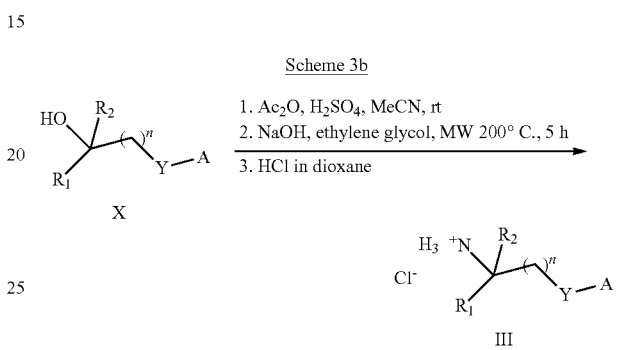

In certain embodiments, amines of Formula III, where $R_1$ is hydrogen and A, $R_2$, Y and n are as defined in Formula (I), (Ia), (Ib), can be prepared as described in Scheme 3a. Alcohols of Formula X can be reacted with phthalimide under Mitsunobu reaction conditions to give the corresponding compounds of Formula XI (Scheme 3a, Step 1a), as reported in Więcek M et al., *Bioorg. Med. Chem.,* 2011, 19, 2850-2858; or Mitsunobu, O. *Synthesis,* 1981, 1; which are incorporated herein as reference. Alternatively, compounds of Formula XI can also be prepared under standard Gabriel reaction conditions, starting from the appropriate bromides of Formula XII (Scheme 3a, Step 1b). Bromides of Formula XII are commercially available or can be prepared from commercially available compounds according to general synthetic procedures described for instance in Michael Smith, Jerry March—*March's Advanced Organic Chemistry: reactions mechanisms and structure*—6th Edition, John Wiley & Sons Inc., 2007, which is incorporated herein as reference. The corresponding amines of Formula III can then be obtained as hydrochloric salts upon hydrazine-mediated cleavage in refluxing ethanol followed by acidic work-up (Scheme 3a, Step 2). If desired, amines of Formula III can also be prepared as free bases, by a neutralization step using inorganic bases such as sodium carbonate, sodium bicarbonate and the like, followed by extractions in organic solvents, such as dichloromethane, ethyl acetate and diethyl ether during the final work-up procedure.

Scheme 3b

In certain embodiments, amines of Formula III, where both $R_1$ and $R_2$ are different from hydrogen, and A, Y and n are defined as in Formula (I), (Ia), (Ib), can be prepared from the corresponding tertiary alcohols of Formula X by a two-step procedure, as exemplified in Scheme 3b, and reported in Timberlake J. W. et al, *J. Org. Chem.* 1981, 46, 2082-2089, which is incorporated herein as reference. Compounds of Formula X can be reacted with acetic anhydride under acidic conditions, followed by basic hydrolysis of the acetamide intermediate. Final treatment with hydrochloric acid in dioxane afforded the corresponding tertiary amines of Formula III as hydrochloric salts.

Scheme 3c

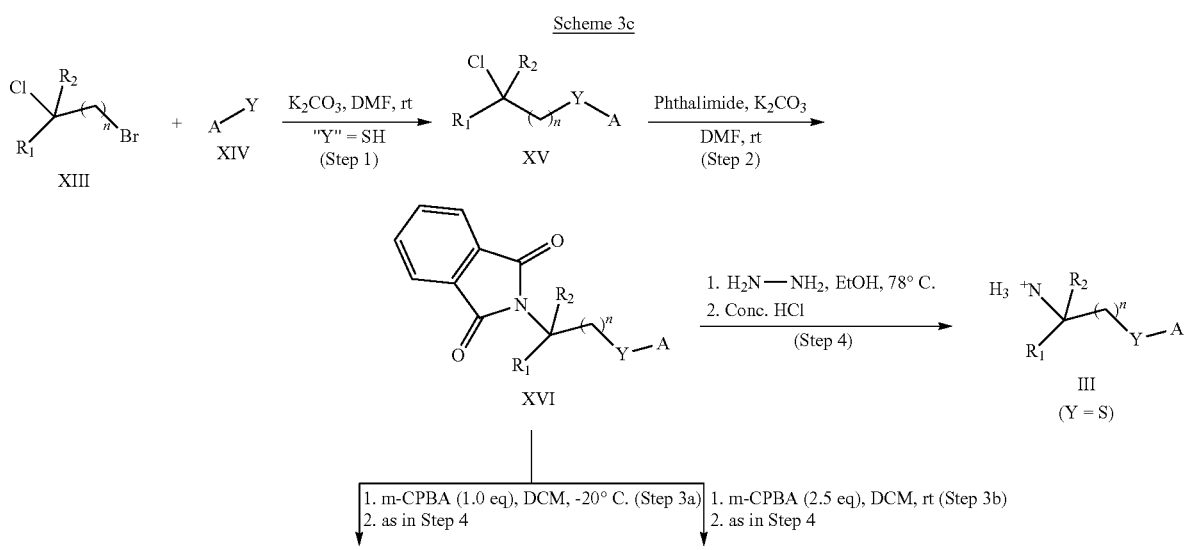

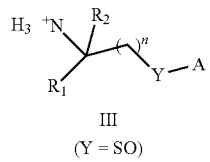

III
(Y = SO)

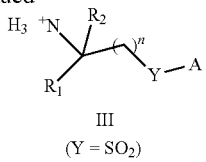

III
(Y = SO$_2$)

In certain embodiments, amines of Formula III, where Y is a group containing one heteroatom selected from the groups consisting of O, S, SO, SO$_2$ or NR$_{12}$, are either commercially available or can be obtained according to standard synthetic methods as reported, for instance, in Michael Smith, Jerry March—*March's Advanced Organic Chemistry: reaction mechanisms and structure*—6$^{th}$ Edition, John Wiley & Sons Inc., 2007, which is incorporated herein as reference. For instance, when Y is a heteroatom such as sulfur, or a group consisting of SO or SO$_2$, as exemplified in Scheme 3c, appropriate bromo-chloro alkanes of Formula XIII can be reacted with compounds of Formula XIV in the presence of inorganic bases, such as potassium carbonate, to deliver the corresponding chloro sulfides of Formula XV (Scheme 3c, Step 1), as described in Rainer E M et al. *ChemMedChem* 2007, 2, 285-287. Compounds of Formula XV can be converted to the appropriate phthalimides of Formula XVI under standard Gabriel reaction conditions (Scheme 3c, Step 2). Phthalimides of Formula XVI can be oxidized with m-chloroperbenzoic acid leading to the formation of the corresponding sulfoxides and sulfones (Scheme 3c, Step 3a and 3b). Amines of Formula III can be then obtained as hydrochloric salts upon hydrazine-mediated cleavage in refluxing ethanol followed by acidic work-up (Scheme 3c, Step 4). If desired, amines of Formula III can also be prepared as free bases, by a neutralization step using inorganic bases such as sodium carbonate, sodium bicarbonate and the like, followed by extractions in organic solvents, such as dichloromethane, ethyl acetate and diethyl ether during the final work-up procedure.

Synthesis of Compounds of Formula (X):

In certain embodiments, alcohols of Formula X, where R$_1$ and R$_2$ are both hydrogen, and A, Y and n are defined as in compounds of Formula (I), (Ia), (Ib), are either commercially available or can be prepared from the corresponding carboxylic acids or esters using common reducing agents, such as LiAlH$_4$, as reported, for instance, in Michael Smith, Jerry March—*March's Advanced Organic Chemistry: reaction mechanisms and structure*—6$^{th}$ Edition, John Wiley & Sons Inc., 2007, which is incorporated herein as reference.

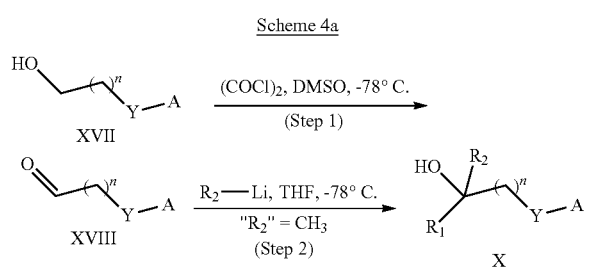

Scheme 4a

In certain embodiments, alcohols of Formula X, where R$_1$ is hydrogen, R$_2$ is different from hydrogen, and A, R$_2$, Y, and n are defined as in compounds of Formula (I), (Ia), (Ib), are either commercially available or can be accessed by a two-step procedure starting from suitable commercial alcohols of Formula XVII, as exemplified in Scheme 4a. Swern oxidation to the corresponding aldehydes of Formula XVIII followed by addition of the appropriate alkyllithium or Grignard reagent can deliver the α-substituted alcohols of Formula X.

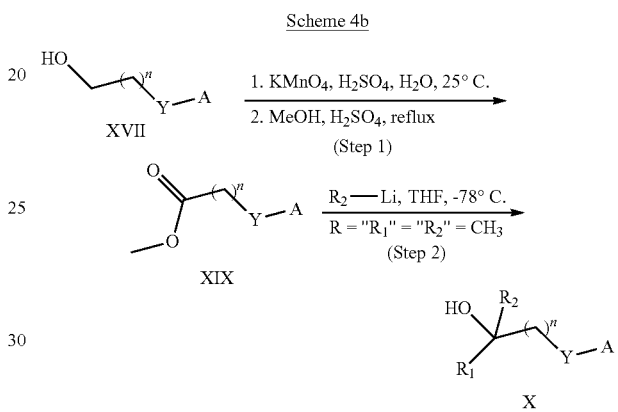

Scheme 4b

In certain embodiments, α-disubstituted alcohols of Formula X, where both R$_1$ and R$_2$ are different from hydrogen, and A, R$_1$, R$_2$, Y, and n are as defined in compound of Formula (I), (Ia), (Ib), can be obtained by a two-step procedure starting from suitable alcohols of Formula XVII, as exemplified in Scheme 4b. Oxidation to carboxylic acid and esterification to the corresponding methyl esters of Formula XIX, followed by addition of the appropriate alkyllithium can deliver the α-disubstituted alcohols of Formula X (Scheme 4b, Step 1-2).

VI. Pharmaceutically Acceptable Salts

It will be understood that, as used herein, references to the compounds of Formula (I), (Ia), (Ib) are meant to include also the pharmaceutically acceptable salts or derivatives thereof.

Furthermore, the compounds of Formula (I), (Ia), (Ib) may form an acid addition salt or a salt with a base, depending on the kind of the substituents, and these salts are included in the present invention, as long as they are pharmaceutically acceptable salts.

The terms "the compound of the invention" and "the compounds of the present invention" and "the compounds of Formula (I), (Ia), (Ib)" refer to each of the compounds of Formula (I), (Ia), (Ib) are meant to include their pharmaceutically acceptable salts, hydrates, solvates, and crystalline forms and also any suitable forms as illustrated hereinafter.

As used herein, the term "salt" refers to any salt of a compound according to the present invention prepared from an inorganic or organic acid or base and internally formed salts. Typically, such salts have a physiologically acceptable anion or cation.

Suitably physiologically or pharmaceutically acceptable salts of the compounds of the present invention include the hydrochloride, acetate, citrate, gluconate, lactate, tartrate, phosphate, borate, maleate, sulphate and nitrate, the hydrochloride being preferred.

The salts of compounds of Formula (I), (Ia), (Ib) may be prepared by reacting a basic compound with the desired acid in solution.

Physiologically or pharmaceutically acceptable salts are particularly suitable for medical applications because of their greater aqueous solubility relative to the parent compound.

Pharmaceutically acceptable salts may also be prepared from other salts including other pharmaceutically acceptable salts of the compounds of Formula Formula (I), (Ia), (Ib) using conventional methods.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compounds of the invention are within the scope of the invention. The compounds of Formula Formula (I), (Ia), (Ib) may readily be isolated in association with solvent molecules by crystallization or evaporation of an appropriate solvent to give the corresponding solvates.

The compounds of Formula Formula (I), (Ia), (Ib) may be in crystalline form. In certain embodiments, the crystalline forms of the compounds of Formula (I), (Ia), (Ib) are polymorphs.

The subject invention also includes isotopically-labelled compounds, which are identical to those recited in Formula (I), (Ia), (Ib) and following, but differ for the fact that one or more atoms are replaced by an atom having an atomic mass or mass number different from the atomic mass or mass number usually found in nature. Examples of isotopes that can be incorporated into the compounds of the invention and pharmaceutically acceptable salts thereof include isotopes of hydrogen, carbon, nitrogen, oxygen, phosphorous, sulfur, fluorine, iodine, and chlorine, such as $^2$H, $^3$H, $^{11}$C, $^{13}$C, $^{14}$C, $^{15}$N, $^{17}$O, $^{18}$O, $^{31}$P, $^{32}$P, $^{35}$S, $^{18}$F, $^{36}$Cl, $^{123}$I, $^{125}$I.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^3$H, $^{14}$C are incorporated, are useful in drug and/or substrate tissue distribution assays. Tritiated, i.e. $^3$H, and carbon-14, i.e. $^{14}$C, isotopes are particularly preferred for their ease of preparation and detectability. $^{11}$C and $^{18}$F isotopes are particularly useful in PET (Positron Emission Tomography), and $^{125}$I isotopes are particularly useful in SPECT (Single Photon Emission Computerized Tomography), all useful in brain imaging. Further, substitution with heavier isotopes such as deuterium, i.e. $^2$H, can afford certain therapeutic advantages resulting from greater metabolic stability, for example increased in vivo half-life or reduced dosage requirements and, hence, may be preferred in some circumstances. Isotopically-labelled compounds of Formula (I), (Ia), (Ib) and following of this invention can generally be prepared by carrying out the procedures disclosed in the Schemes and/or in the Examples below, by replacing a non-isotopically-labelled reagent with a readily available isotopically-labelled reagent.

Certain groups/substituents included in the present invention may be present as isomers or in one or more tautomeric forms. Accordingly, in certain embodiments, the compounds of Formula (I), (Ia), (Ib) may exist in the form of tautomers or geometrical isomers in some cases, depending on the kinds of the substituents. In the present specification, the compounds may be described in only one form of such isomers, but the present invention includes all such isomers, isolated forms of the isomers, or a mixture thereof. Furthermore, the compounds of Formula (I), (Ia), (Ib) may have asymmetric carbon atoms or axial asymmetries in some cases and, correspondingly, it may exist in the form of optical isomers such as an (R)-form, an (S)-form, and the like. The present invention includes within the scope all such isomers, including racemates, enantiomers and mixtures thereof.

In particular, within the scope of the present invention are included all stereoisomeric forms, including enantiomers, diastereoisomers, and mixtures thereof, including racemates and the general reference to the compounds of Formula (I), (Ia), (Ib) includes all the stereoisomeric forms, unless otherwise indicated.

In general, the compounds or salts of the invention should be interpreted as excluding those compounds (if any) which are so chemically unstable, either per se or in water, that they are clearly unsuitable for pharmaceutical use through all administration routes, whether oral, parenteral, or otherwise. Such compounds are known to the skilled chemist. Prodrugs or compounds which are stable ex vivo and which are convertible in the mammalian (e.g. human) body to the inventive compounds are, however, included.

The present invention also encompasses active metabolites of compounds of Formula (I), (Ia), (Ib).

VII. Pharmaceutical Compositions

Another aspect of the present invention relates to pharmaceutical compositions containing a compound of Formula (I), (Ia), (Ib).

The pharmaceutical compositions of the present invention encompass any compositions made by mixing a compound of the present invention and a pharmaceutically acceptable carrier. Such compositions are suitable for pharmaceutical use in an animal or human.

The pharmaceutical compositions of the present invention comprise a therapeutically effective amount of one or more compounds of Formula (I), (Ia), (Ib) or a pharmaceutically acceptable salt thereof, and a pharmaceutically acceptable carrier.

A pharmaceutical composition may optionally contain other active ingredients. The term "carrier" refers to a vehicle, excipient, diluents, or adjuvant with which the therapeutic or active ingredient is administered. Any carrier and/or excipient suitable for the form of preparation desired for administration is contemplated for use with the compounds disclosed herein.

The carrier may take a wide variety of forms depending on the form of preparation desired for administration, e.g. oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents, and the like in the case of oral solid preparations such as, for example, powders, hard and soft capsules and tablets, with the solid oral preparations being preferred over the liquid preparations.

In certain embodiments, the compounds of the present invention can be combined as the active ingredient in intimate admixture with a suitable pharmaceutical carrier and/or excipient according to conventional pharmaceutical compounding techniques.

The compositions include compositions suitable for parenteral, including subcutaneous, intramuscular, and intravenous, pulmonary, nasal, rectal, topical or oral administration. Suitable route of administration in any given case will depend in part on the nature and severity of the conditions being treated and on the nature of the active ingredient. An exemplary route of administration is the oral route. The compositions may be conveniently presented in unit dosage form and prepared by any of the methods well-known in the art of pharmacy. The preferred compositions include compositions suitable for oral, parenteral, topical, subcutaneous, or pulmonary, in the form of nasal or buccal inhalation, administration. The compositions may be prepared by any of the methods well-known in the art of pharmacy.

The pharmaceutical compositions may be in the form of tablets, pills, capsules, solutions, suspensions, emulsion, powders, suppositories and as sustained release formulations.

If desired, tablets may be coated by standard aqueous or non-aqueous techniques. In certain embodiments, such compositions and preparations can contain at least 0.1 percent of active compound. The percentage of active compound in these compositions may, of course, be varied and may conveniently be between about 1 percent to about 60 percent of the weight of the unit. The amount of active compound in such therapeutically useful compositions is such that therapeutically active dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil. Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavouring agent such as cherry or orange flavour. To prevent breakdown during transit through the upper portion of the gastrointestinal tract, the composition be an enteric coated formulation.

Compositions for topical administration include, but are not limited to, ointments, creams, lotions, solutions, pastes, gels, sticks, liposomes, nanoparticles, patches, bandages and wound dressings. In certain embodiments, the topical formulation comprises a penetration enhancer.

Compositions for pulmonary administration include, but are not limited to, dry powder compositions consisting of the powder of a compound of Formula (I), (Ia), (Ib) or a salt thereof, and the powder of a suitable carrier and/or lubricant. The compositions for pulmonary administration can be inhaled from any suitable dry powder inhaler device known to a person skilled in the art.

Administration of the compositions is performed under a protocol and at a dosage sufficient to reduce the inflammation and pain in the subject. In some embodiments, in the pharmaceutical compositions of the present invention the active principle or active principles are generally formulated in dosage units. The dosage unit may contain from 0.1 to 1000 mg of a compound of Formula (I), (Ia), (Ib) per dosage unit for daily administration.

In some embodiments, the amounts effective for topical formulation will depend on the severity of the disease, disorder or condition, previous therapy, the individual's health status and response to the drug. In some embodiments, the dose is in the range from 0.001% by weight to about 60% by weight of the formulation.

When used in combination with one or more other active ingredients, the compound of the present invention and the other active ingredient may be used in lower doses than when each is used singly.

With respect to formulations with respect to any variety of routes of administration, methods and formulations for the administration of drugs are disclosed in *Remington's Pharmaceutical Sciences*, 17$^{th}$ Edition, Gennaro et al. Eds., Mack Publishing Co., 1985, and *Remington's Pharmaceutical Sciences*, Gennaro A R ed. 20$^{th}$ Edition, 2000, Williams & Wilkins PA, USA, and *Remington: The Science and Practice of Pharmacy*, 21$^{st}$ Edition, Lippincott Williams & Wilkins Eds., 2005; and in *Ansel's Pharmaceutical Dosage Forms and Drug Delivery Systems*, 8$^{th}$ Edition, Lippincott Williams & Wilkins Eds., 2005, which are herein incorporated as reference.

VIII. Medical Uses of Compounds of Formula (I), (Ia), (Ib) and Therapeutic Treatments In accordance with another aspect of the present invention compounds of Formula (I), (Ia), (Ib) are provided for use as a medicament.

In accordance with some embodiments, the present invention provides the compounds of Formula (I), (Ia), (Ib) for use in treating diseases or disorders associated with increased (relative to physiological or desired) levels of acid ceramidase protein or function, for example in subjects where acid ceramidase is overactive or over-expressed.

In accordance with other embodiments, a method of treatment of diseases or disorders associated with increased (relative to physiological or desired) levels of acid ceramidase protein or function, for example in subjects where acid ceramidase is overactive or over-expressed, is also provided.

In some embodiments, the compounds of Formula (I), (Ia), (Ib) and their pharmaceutical compositions and methods of administering them, are useful in treating diseases or disorders involving uncontrolled cell proliferation and/or dysfunctional sphingolipid signal transduction.

Diseases and disorders involving uncontrolled cell proliferation include, but are not limited to, pre-malignant conditions, for example hyperplasia, metaplasia or dysplasia, cancer, cancer metastasis, benign tumors, hyperproliferative disorders and benign dysproliferative disorders. The treatment may be prophylactic or therapeutic. The subject to be treated may be an animal (e.g., mouse, rat, non-human primate and non-human mammal) or human.

In some embodiments, the compounds of Formula (I), (Ia), (Ib) and their pharmaceutical compositions and methods of administering them, are useful in treating diseases or disorders involving primary and metastatic neoplastic diseases.

Primary and metastatic neoplastic diseases and related disorders that can be treated and/or prevented by the methods, compounds and compositions of the presently disclosed subject matter include, but are not limited to, prostate cancer, colorectal cancer, liver cancer, head and neck cancer, breast cancer, melanoma, metastatic melanoma, precancerous skin conditions such as actinic keratosis, skin cancers such as squamous cell carcinoma and basal cell carcinoma, and hematological malignancies such as chronic myelogeneous leukemia.

In accordance with certain embodiments the present invention provides a method for the treatment or prevention of cancer, cancer metastasis, or psoriasis, comprising the administration of a therapeutically effective compound of Formula (I), (Ia), (Ib) according to one or more of the embodiments described above, in a subject in need of treatment.

Cancers and related disorders that can be treated and/or prevented by the methods and compositions of the presently disclosed subject matter include, but are not limited to acute and chronic leukemia; polycythemia vera; lymphomas such as Hodgkin's disease, non-Hodgkin's disease; multiple myelomas, plasmacytoma; Waldenstrom's acroglobulinemia; gammopathy; heavy chain disease; bone and connective tissue sarcomas; brain tumors; breast cancer; adrenal cancer; thyroid cancer; pancreatic cancer; pituitary cancers; eye cancers; vaginal cancers; vulvar cancer; cervical cancers; uterine cancers; ovarian cancers; head and neck squamous cell cancers (HNSCCs), esophageal cancers; stomach cancers; colon cancers; rectal cancers; liver cancers; cholangiocarcinomas; testicular cancers, prostate cancers; penal cancers; oral cancers; basal cancers; salivary gland cancers; pharynx cancers; skin cancers; kidney cancers; Wilms' tumor; bladder cancers, myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas. In certain embodiments, the present invention provides for compounds of Formula (I), (Ia), (Ib) for the use in the treatment and/or prevention of breast cancer, prostate cancer, melanoma, alveolar cancer, or head and neck cancer.

The inventors found that the compounds of Formula (I), (Ia), (Ib) play a role as regulator of cancer progression and are effective in the treatment of cancerous forms which are associated with an increased level of acid ceramidase protein or function, for example in subjects where acid ceramidase is overactive or over-expressed.

In accordance with certain embodiments the compounds of the invention are selective compounds for the treatment of prostate cancer, skin cancer especially melanoma, brain cancer, breast cancer, hepatocarcinoma, liver cancer, colon cancer or pancreatic cancer.

In certain embodiments, the present invention concerns compounds of Formula (I), (Ia), (Ib) for use in the treatment of inflammatory diseases, such as rheumatoid arthritis and ulcerative colitis.

In certain embodiments, the compounds of Formula (I), (Ia), (Ib) are useful in the treatment of different pain syndromes, disorders, diseases and conditions characterized by nociceptive pain, neuropathic pain, inflammatory pain, non-inflammatory pain, pain associated with acute conditions such as post-operative or post-traumatic stress disorders, pain associated with chronic conditions such as diabetes. Said method comprises administering a therapeutically effective amount of a compound of Formula (I), (Ia), (Ib) or a pharmaceutically acceptable salt thereof, or a pharmaceutical composition thereof to the mammal.

In certain embodiments, the present invention provides the compounds of Formula (I), (Ia), (Ib) for use in treating pulmonary diseases, such as asthma, chronic obstructive pulmonary disease (COPD), adult respiratory disease, acute respiratory distress syndrome, chronic bronchitis, emphysema and cough.

In certain embodiments, the present invention provides the compounds of Formula (I), (Ia), (Ib) for use in treating diseases or disorders associated with neurodegeneration, such as Parkinson's disease, Alzheimer's disease, Huntington's diseases, multiple sclerosis and amyotrophic lateral sclerosis.

In some embodiments, the compounds of Formula (I), (Ia), (Ib) and their pharmaceutical compositions and methods of administering them, are useful in treating or preventing a disease or disorder when administered in combination with other treatments.

In an additional aspect the present invention also concerns combination therapies or treatment with a compound of Formula (I), (Ia), (Ib) or pharmaceutical composition containing them. In some embodiments, the compounds of Formula (I), (Ia), (Ib), and their pharmaceutical compositions and methods of administering them, are useful in treating cancer when administered in combination with other pharmacological agents or active ingredients.

In certain embodiments these pharmacological agents are chemotherapeutic agents including, but not limited to, doxorubicin, daunorubicin, etoposide, cisplatin, oxaliplatin, carboplatin, gemcitabine, 5-fluorouracil, capecitabine, tegafur uracil (UFT), dacarbazine, fenretinide, camptothecin, irinotecan, fludarabine, vinblastine, taxol, mitomycin C.

In some embodiments, the compounds of Formula (I), (Ia), (Ib) and their pharmaceutical compositions and methods of administering them, are useful in treating various cancers when administered before, during or after patient's treatment with radiation therapy.

In accordance with an additional aspect, the present invention provides a method of inhibiting ceramidase-related activity by contacting a biological sample with a compound of Formula (I), (Ia), (Ib) as described above.

In certain embodiments the biological sample is an in vitro cell sample or an in vivo cell sample. The biological sample includes cells in culture media or lysed cells containing acid ceramidase. The biological sample includes cells present in plasma, urine, a tissue or organ sample or present in a subject. Accordingly in certain embodiments the methods of the invention can be used in medical or scientific research related to acid ceramidase and ceramidase-related activity.

IX. Biological Methods to Evaluate the Activity of the Compounds of the Invention Fluorescent-Based In Vitro Assay
General:
To evaluate the potency of the compounds towards acid ceramidase, a fluorescence-based in vitro assay previously described in literature (Bedia C et al., *ChemBioChem*, 2007, 8, 642-648) was implemented and optimized. This assay is based on a "fluorogenic probe" containing a coumarin group and a sphingoid base moiety (see figure below), which is not fluorescent in itself, but upon enzymatic cleavage by acid ceramidase followed by a chemical transformation liberates the fluorescent molecule umbelliferone (7-hydroxychromen-2-one). By quantifying the generation of umbelliferone using a fluorescence plate-reader, the level of enzymatic activity can be measured, whereby $IC_{50}$ values of compounds that inhibit this activity can be generated.

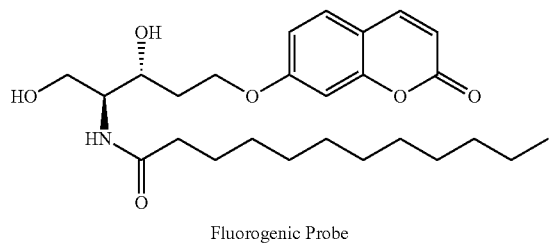 [SMILES: CCCCCCCCCCCC(=O)N[C@@H](CO)[C@H](O)CCOc1ccc2ccc(=O)oc2c1]

Fluorogenic Probe

Lysosomal lysate, enriched with acid ceramidase, was prepared from a cell line stably expressing human acid ceramidase. In the assay, the fluorogenic probe (or substrate) serves as a ceramide-analogue, which is recognized and hydrolyzed at the amide bond by acid ceramidase from the enriched lysate to yield the fatty acid and coumarinic aminodiol. By treating the solution with sodium periodate ($NaIO_4$), the coumarinic aminodiol is subsequently oxidized into an aldehyde intermediate, which undergoes a β-elimination reaction to release the strongly fluorescent umbelliferone.

Synthesis of the Fluorogenic Probe:

The fluorogenic probe was synthesized by the improved method described by Xia Z et al (*Bioorg. Med. Chem.*, 2010, 18, 1003-1009), except for the last step (i.e. the acylation of the coumarinic aminodiol with dodecanoic acid), which was carried out as described by Bedia C et al (*J. Lipid Res.*, 2010, 3542-3547), using 1-ethyl-3-(3-dimethylaminopropyl)carbodiimide hydrochloride (EDC.HCl), 1-hydroxybenzotriazole, and N,N-diisopropylethylamine in DMF. Analytical data of the fluorogenic probe:

N-[(1S,2R)-2-hydroxy-1-(hydroxymethyl)-4-(2-oxochromen-7-yl)oxy-butyl]dodecanamide White solid. Purity >95%; $^1$H NMR (400 MHz, DMSO-$d_6$): δ 0.85 (t, J=7.1 Hz, 3H), 1.19-1.26 (m, 16H), 1.41-1.54 (m, 2H), 1.66-1.76 (m, 1H), 1.92-2.02 (m, 1H), 2.04-2.17 (m, 2H), 3.51-3.57 (m, 2H), 3.64-3.76 (m, 2H), 4.19 (t, J=6.6 Hz, 2H), 4.54 (t, J=5.5 Hz, 1H), 4.84 (d, J=6.2 Hz, 1H), 6.30 (d, J=9.5 Hz, 1H), 6.93 (d, J=2.4 Hz, 1H), 6.96 (m, 1H), 7.54 (d, J=8.4 Hz, 1H), 7.64 (d, J=8.4 Hz, 1H), 8.01 (d, J=9.5 Hz, 1H). $^{13}$C NMR (101 MHz, $CDCl_3$): δ 13.90, 22.04, 25.33, 28.60, 28.67, 28.78, 28.95, 28.99 (2C), 31.26, 32.85, 35.47, 55.16, 60.58, 65.60, 66.72, 101.09, 112.18, 112.31, 112.61, 129.42, 144.29, 155.38, 160.24, 161.87, 172.17. $[\alpha]^{20}_D$= −10.13±0.6 (c=0.43, $CHCl_3$). MS (ESI) m/z: 462.2 $[M-H]^+$.

Preparation of Enzyme-Enriched Lysate:

A lysosomal human acid ceramidase protein preparation was obtained from HEK293 cells stably expressing acid ceramidase suspended in 20 mM Tris HCl (pH 7.5) with 0.32 M sucrose. The cell solution was sonicated and centrifuged at 800×g for 15 min at 4° C. Supernatants were then centrifuged at 12,000×g for 30 min at 4° C. Pellets were re-suspended in phosphate-buffered saline (PBS) pH 7.4 and subjected to two freeze-thaw cycles at −80° C. The suspension was finally centrifuged at 105,000×g for 1 h at 4° C. and protein concentration was measured in the supernatant with bicinchonic-acid based protein assay. This human acid ceramidase-enriched preparation allowed us to further optimize the enzymatic assay and to use smaller amounts of lysate (2 µg/well) and substrate (5 µM).

Procedure for Fluorescent-Based In Vitro Assay:

The assay was performed in Optiplate 96-wells black plates, with each reaction well containing a mixture of 25 mM sodium acetate buffer pH 4.5 and a fixed amount of protein (2 µg) in a volume of 85 µL. After 30 min of pre-incubation with test compounds (diluted 20× from DMSO stock solutions at different concentrations), the fluorogenic probe was added (diluted 20× from EtOH stock solution, final concentration 5 µM). After incubation for 3 h at 37° C., the reactions were stopped with 50 µl of methanol and 100 µl of a 2.5 mg/mL $NaIO_4$ fresh solution in 100 mM Glycine/NaOH pH 10.6. The plate was incubated at 37° C. for 2 h in the dark and fluorescence intensities were measured at excitation/emission wavelengths of 360/446 nm. Negative control samples consisted of the same incubation mixture in the absence of protein extracts. The $IC_{50}$ values or percent of inhibition, at the indicated concentration, of selected compounds described in the invention are reported in Table 2.

Procedure for LC-MS Based In Vitro Assay:

hAC protein preparation (10 µg) was preincubated with inhibitors (final DMSO concentration 1%) in assay buffer (100 mM sodium phosphate, 0.1% Nonidet P-40, 150 mM NaCl, 3 mM DTT, 100 mM sodium citrate, pH 4.5) for 30 min at 37° C. Reactions were started by the addition of 50 µM N-lauroyl ceramide (Nu-Chek Prep, Elysian, Minn.) and carried on for 30 min at 37° C. Reactions were stopped by addition of a mixture of chloroform/methanol (2:1) containing 1 nmol 11-lauroleic acid (NuChek Prep). The organic phases were collected, dried under nitrogen and analyzed by UPLC/MS (Acquity, Waters). In the negative-ion mode monitoring the reaction product (lauric acid, m/z=199) using 11-lauroleic acid as internal standard.

Lipids were eluted on an Acquity UPLC BEH $C_{18}$ column (50×2.1 mmID, particle size 1.7 µm), column flow at 0.5 mL/min for 1.5 min with a gradient of acetonitrile and water, both containing 0.25% acetic acid and 5 mM ammonium acetate (70% to 100% acetonitrile in 0.5 min, 100% acetonitrile for 0.5 min, 70% acetonitrile for 0.4 min). The column temperature was 40° C. Electrospray ionization (ESI) was in the negative mode, capillary voltage was 1 kV and cone voltage was 50 V. $N_2$ was used as drying gas at a flow rate of 500 L/h and at a temperature of 400° C.

The $[M-H]^-$ ion was monitored in the selected-ion monitoring mode (m/z values: lauric acid 199, 11-lauroleic acid 197.35). Calibration curves were generated with authentic lauric acid (Nu Check Prep). Inhibition of AC activity was calculated as reduction of lauric acid in the samples compared to vehicle controls. $IC_{50}$ values were calculated by non-linear regression analysis of log [concentration]/inhibition curves using GraphPad Prism 5 (GraphPad Software Inc., CA—USA) applying a standard slope curve fitting.

Lipid Extraction and Ceramide, Sphingosine and Sphinganine Analysis

Lipids were extracted from mouse tissue lysate with a chloroform/methanol mixture (2:1, 3 mL) containing internal standards. The organic phase was collected, dried under nitrogen, and dissolved in chloroform/methanol (1:3) for LC-MS analyses. Ceramides, sphingosine and sphinganine were analyzed by LC-MS/MS, using a Waters Acquity UPLC coupled with a Waters Xevo TAMS and interfaced with ESI. Separation was done on a Waters Acquity BEH $C_{18}$ 1.7 µm column (2.1×50 mm) at 60° C. A step gradient of 0.1% formic acid in acetonitrile/water (20:80) as solvent A and 0.1 formic acid in acetonitrile/isopropyl alcohol (20:80) as solvent B was applied at a flow rate of 0.4 mL/min. Detection was in the positive ionization mode.

Capillary voltage was 3.5 kV and cone voltage was 25 V. The source temperature and desolvation temperatures were set at 120° C. and 600° C. respectively. Desolvation gas and cone gas ($N_2$) flow were 800 and 20 L/h, respectively.

Tissue-derived ceramides were identified by comparison of their LC retention times and $MS^2$ fragmentation patterns with those of authentic standards (Avanti Polar Lipids). Extracted ion chromatograms were used to quantify myristoyl ceramide (C14:0, m/z 510.5>492.5>264.3), palmitoyl ceramide (C16:0, m/z 538.5>520.3>264.3), stearoyl ceramide (C18:0 m/z 566.5>548.3>264.3), lignoceroyl ceramide (C24:0 m/z 650.5>632.3>264.3), nervonoyl ceramide (C24:1 m/z 648.5>630.3>264.3) and using lauroyl ceramide standard (m/z 482.5>464.5>264.3). Detection and analysis were controlled by Waters MassLynx software version 4.1.

Tissue-derived sphingosine and sphinganine were identified by comparison of their LC retention times and $MS^2$ fragmentation patterns with those of authentic standards (Avanti Polar Lipids). Extracted ion chromatograms were used to quantify sphingosine ($C_{18}$:0, m/z 300.5>282.5) and sphinganine standard ($C_{18}$:0, m/z 303>285). Detection and analysis were controlled by Waters MassLynx software version 4.1.

Cell Viability and Proliferation Assays

Cell viability can be defined as the number of living cells in a sample. There are many well-described and widely used methods to evaluate cell viability such as trypan blue dye exclusion, MTT reduction or ATP measurement [for a review, see Stoddart M J, *Cell viability assays: introduction, Methods in Molecular Biology*, 2011, Vol. 740].

Cells are seeded in 12- or 96-well plates in complete medium 24 h before treatment and then incubated for 24 h (single treatment) or 72 h (multiple treatments) with different compounds-concentrations.

Cell viability can be evaluated using the trypan blue exclusion assay, which is based on the principle that viable cells have intact cell membrane and can therefore exclude the trypan blue dye, while damaged/dead cells cannot. Cells are harvested, centrifuged at 800×g for 10 min and pellets re-suspended in PBS. Cells are diluted 1:1 with 0.4% trypan blue dye (Sigma), incubated for 1 min and white (viable) cells are counted with a hemacytometer.

Alternatively, cell viability can be assessed measuring mitochondrial functionality by the MTT assay, which is based on the reduction of the soluble tetrazolium salt MTT [(3-(4,5-dimethylthiazol-2-yl)-2,5-diphenyltetrazolium bromide] into insoluble formazan by mitochondria. Briefly, cells are treated with selected compounds for 24 or 72 h, washed with PBS and incubated with 0.5 mg/mL MTT for 2 h at room temperature. MTT reduction is quantified by absorbance at 570 nm using a UV-visible plate reader.

In some experiments, crystal violet assay can be used to evaluate cells morphology and proliferation: at different time points after treatment cells are washed with PBS and fixed with 4% formaldehyde for 10 min. Cells are stained with 0.4% crystal violet in 50% MeOH for 20 min and extensively washed with water to remove excess dye. Crystal violet is dissolved in DMSO. The absorbance of the dissolved dye, corresponding to the number of viable cells, is measured in a UV-visible plate reader at 570 nm.

Finally, the CellTiter-Glo® Luminescent Cell Viability Assay can be used to determine the number of viable cells in culture based on quantitation of the ATP present, which signals the presence of metabolically active cells. Briefly, a volume of CellTiter-Glo® Reagent equal to the volume of cell culture medium present in each well is added to 96-well plates after drug treatment. Contents are mixed for 2 min on an orbital shaker to induce cell lysis and plate was incubated at room temperature for 10 min to stabilize signal before reading luminescence.

Isobolographic Analysis

Interaction between drugs can be assessed by isobolographic analysis, based on the concept of dose-equivalence which follows from the dose effect curves of the individual drugs (Tallarida R J, *Interactions between drugs and occupied receptors. Pharmacol. Ther.* 2007, 113, 197-209; Tallarida R J, Raffa R B, *The application of drug dose equivalence in the quantitative analysis of receptor occupation and drug combinations. Pharmacol. Ther.* 2010, 127, 165-174). Specifically, the individual drugs' potency and efficacy allow calculating the expected effect of a combination of the two drugs.

In the experiment of combined treatment, isobolograms are constructed by plotting on vertical and horizontal axes the $ED_{50}$ data of the single drugs measured by trypan blue assay after subcronic treatment for 72 hr. The straight line with axial intercepts represents the isobole of additivity and allows calculating the theoretical additive dose. Synergism is indicated by an observed pair (x, y) that plots below the isobole for the specified effect, whereas sub-additivity is indicated when an observed pair (x, y) plots above the isobole.

Statistics

GraphPad Prism software (GraphPad Software, Inc., USA) was used for statistical analysis. Data were analyzed using the Student t-test or 1-way ANOVA followed by Bonferroni post hoc test for multiple comparisons. Two-way ANOVA was used to compare the means of data with two independent variables. Differences between groups were considered statistically significant at values of $p<0.05$. Results are expressed as mean±SEM.

PREPARATIVE EXAMPLES

Abbreviations used for solvents and reagents are: acetonitrile (MeCN), ammonium chloride ($NH_4Cl$), n-butyl lithium (n-BuLi), m-chloroperbenzoic acid (m-CPBA), dichloromethane (DCM), 4-(dimethylamino)-pyridine (DMAP), N,N-diisopropylethylamine (DIPEA), N,N-dimethylformamide (DMF), dimethylsulfoxide (DMSO), diethyl azodicarboxylate (DEAD), ethanol (EtOH), ethyl acetate (EtOAc), hydrochloric acid (HCl), lithium aluminum hydride ($LiAlH_4$), methanol (MeOH), oxalyl chloride (($COCl)_2$)—potassium carbonate ($K_2CO_3$), potassium permanganate ($KMnO_4$), sodium bicarbonate ($NaHCO_3$), sodium carbonate ($Na_2CO_3$), sodium hydroxide (NaOH), sodium sulfate ($Na_2SO_4$), sodium thiosulfate ($Na_2S_2O_3$), sulfuric acid ($H_2SO_4$), tetrahydrofuran (THF), tetrakis(triphenylphosphine) palladium(0) ($Pd(PPh_3)_4$), triethylamine ($Et_3N$), triphenylphosphine ($Ph_3P$). Other abbreviations used are: aqueous (aq.), based on recovery starting material (brsm), equivalents (eq.), hours (h), minutes (min), room temperature (rt), saturated (sat.).

Hydrogenation reactions were performed using H-Cube™ continuous hydrogenation equipment (SS-reaction line version), employing disposable catalyst cartridges (CatCart™) preloaded with the required heterogeneous catalyst. Microwave heating was performed using Explorer™-48 positions instrument (CEM).

UPLC-MS analyses were run on a Waters ACQUITY UPLC-MS instrument consisting of a SQD Single Quadropole Mass Spectrometer equipped with an electrospray ionization interface and a photodiode array (PDA) detector. The UPLC column was an ACQUITY UPLC BEH $C_{18}$ column (50×2.1 mmID, particle size 1.7 μm) with a Van-Guard BEH $C_{18}$ pre-column (5×2.1 mmID, particle size 1.7 μm). The mobile phases were 10 mM ammonium acetate at pH 5 adjusted with acetic acid (A) and 10 mM ammonium acetate in MeCN-water (95:5) at pH 5 (B). Electrospray ionization in positive and negative mode was used in the mass scan range 100-500 Da, and PDA range was 210-400 nm.

Purifications by automated column chromatography were done using a Teledyne ISCO apparatus (CombiFlash™ Rf) with pre-packed silica gel columns of different sizes (from 4-80 g). Mixtures of increasing polarity of cyclohexane (A) and EtOAc (B) or DCM (A) and MeOH (B) were used as eluents.

Purification by preparative HPLC-MS were run on a Waters Autopurification system consisting of a 3100 Single Quadropole Mass Spectrometer equipped with an electrospray ionization interface and a 2998 Photodiode Array Detector. The HPLC system included a 2747 Sample Manager, 2545 Binary Gradient Module, System XBridge™ Prep $C_{18}$ OBD column (100×19 mmID, particle size 5 μm) with a XBridge™ Prep $C_{18}$ (10×19 mmID, particle size 5 μm) Guard Cartridge. The mobile phases were either 1) water (A) and MeCN (B) or 2) 10 mM ammonium acetate at pH 5 adjusted with acetic acid (A) and 10 mM ammonium acetate in MeCN:water (95:5) at pH 5 (B). Electrospray ionization in positive and negative mode was used in the mass scan range 100-500 Da.

NMR experiments were run on a Bruker Avance III 400 system (400.13 MHz for $^1H$, and 100.62 MHz for $^{13}C$), equipped with a BBI probe and Z-gradients. Spectra were acquired at 300 K, using deuterated dimethylsulfoxide (DMSO-$d_6$), deuterated chloroform (CDCl$_3$) or deuterated methanol (MeOD) as solvents. Chemical shifts for $^1H$ and $^{13}C$ spectra were recorded in parts per million using the residual non-deuterated solvent as the internal standard (for CDCl$_3$: 7.26 ppm, $^1H$ and 77.16 ppm, $^{13}C$; for DMSO-$d_6$: 2.50 ppm, $^1H$; 39.52 ppm, $^{13}C$; for MeOD: 3.31 ppm, $^1H$; 49.00 ppm $^{13}C$). All final compounds were >95% pure by NMR ($^1H$, $^{13}C$, $^1H$-$^1H$ COSY, $^1H$-$^{13}C$ HSQC) and UPLC (UV). DMSO stock solutions of final compounds used for biological tests were evaluated prior to tests (NMR, UPLC), and the concentration was evaluated by quantitative NMR.

General Procedure I: Synthesis of Compounds of Formula I (Scheme 1)

Method A:

In an oven-dried flask, triphosgene (1.0 eq.) was dissolved in dry DCM (5 mL per mmol triphosgene). A solution of the optionally substituted 3H-1,3-benzoxazol-2-one 11 (1.0 eq.) and Et$_3$N (4.0 eq.) in dry DCM (5.6 mL per mmol II) was added at 0° C., and the reaction was stirred for 1 h at rt under nitrogen. Then a solution of the amine III (1.5 eq.) and Et$_3$N (1.5 eq.) in dry DCM (6.5 mL per mmol III) was added at 0° C., and the reaction was stirred at rt for 3 h. The reaction mixture was diluted with DCM (20 mL per mmol II) and quenched with sat. aq. NH$_4$Cl solution (30 mL per mmol II). The two phases were separated and the aqueous layer was extracted with DCM (3×20 mL per mmol II). The combined organic phases were dried over Na$_2$SO$_4$, evaporated on silica, and the compound was purified by column chromatography using the Teledyne ISCO apparatus (cyclohexane:EtOAc).

Method B:

In an oven-dried flask, p-nitrochloroformate (1.1 eq.) was dissolved in dry DCM (5 mL per mmol p-nitrochloroformate). A solution of the optionally substituted 3H-1,3-benzoxazol-2-one II (1.0 eq.) and Et$_3$N (2.2 eq.) in dry DCM (5.6 mL per mmol II) was added at 0° C., and the reaction was stirred for 1 h at rt under nitrogen. Then a solution of the amine III (1.5 eq.) and Et$_3$N (1.5 eq.) in dry DCM (6.5 mL per mmol III) was added at 0° C., and the reaction was stirred at rt for 3 h. The reaction mixture was diluted with DCM (20 mL per mmol II) and quenched with sat. aq. NH$_4$Cl solution (30 mL per mmol II). The two phases were separated and the aqueous layer was extracted with DCM (3×20 mL per mmol II). The combined organic phases were dried over Na$_2$SO$_4$, evaporated on silica, and the compound was purified by column chromatography using the Teledyne ISCO apparatus (cyclohexane:EtOAc).

General Procedure II: Synthesis of Compounds of Formula II (Scheme 2a)

IV, e.g. bromo-substituted 3H-1,3-benzoxazol-2-one, (1 eq.) was suspended in a 1:1 toluene/EtOH mixture (10 mL per mmol IV). The boronic acid V (1.5 eq.) was added followed by aq. Na$_2$CO$_3$ (2 M, 0.55 mL per mmol IV, 1.1 eq.). The resulting suspension was degassed under nitrogen for 10 min, followed by addition of Pd(PPh$_3$)$_4$ (0.1 eq.) and heating under microwave irradiation at 100° C. for 30 min. The reaction mixture was diluted with EtOAc (40 mL per mmol IV), and water (40 mL per mmol IV) was added. The two phases were separated and the aqueous layer was extracted with EtOAc (2×40 mL per mmol IV). The combined organic phases were dried over Na$_2$SO$_4$, evaporated on silica, and the compound was purified by column chromatography using the Teledyne ISCO apparatus (cyclohexane:EtOAc).

General Procedure III: Synthesis of Compounds of Formula II (Scheme 2b)

Step 1:

This procedure is similar to the General Procedure II, except that vinylboronic acids VI are used instead of boronic acids V.

Step 2:

The alkenyl-substituted 3H-1,3-benzoxazol-2-one VII (1 eq.), was dissolved in EtOAc (75 mL per mmol VII) and hydrogenated in the H-Cube apparatus at 50° C. using 10% Pd/C as catalyst-cartridge and 1 bar hydrogen pressure. The reaction mixture was concentrated under reduced pressure affording pure product.

General Procedure IV: Synthesis of Compounds of Formula II (Scheme 2c)

IV, e.g. bromo-substituted 3H-1,3-benzoxazol-2-one, (1 eq.) was suspended in dry THF (5 mL per mmol IV). n-BuLi (2.2 eq.) was added dropwise at −78° C. and the reaction was stirred for 30 min at −78° C. In a separate flask, the electrophile VIIIa or VIIIb (2.2 eq.) was suspended in dry THF (5 mL per mmol VII) and cooled to −78° C., then the solution containing IV and n-BuLi was added dropwise and the reaction stirred at −78° C. for 30 min. The reaction was quenched with sat. aq. NH$_4$Cl solution (10 mL per mmol II). The two phases were separated and the aqueous layer was extracted with EtOAc (3×10 mL per mmol II). The combined organic phases were dried over Na$_2$SO$_4$, evaporated on silica, and the compound was purified by column chromatography using the Teledyne ISCO apparatus (cyclohexane:EtOAc).

General Procedure V: Synthesis of Compounds of Formula IV (Scheme 2d)

1,1'-Carbonyldiimidazole (1.2 eq.) was added to a solution of the optionally substituted aminophenol IX (1 eq.) in DMF (2.0 mL per mmol IX), and the reaction was heated to 60° C. for 2 h. After cooling to rt, the reaction mixture was poured into water (15 mL per mmol V) and extracted with EtOAc (3×15 mL per mmol IX). The combined organic phases were washed with brine (15 mL per mmol IX), dried over $Na_2SO_4$, and evaporated on silica. The compound was purified by column chromatography using the Teledyne ISCO apparatus (cyclohexane:EtOAc).

General Procedure VI: Synthesis of Compounds of Formula III (Scheme 3a)

Step 1a:

In an oven-dried flask, phthalimide (1.0 eq.), $Ph_3P$ (1.0 eq.) and alcohol X (1.0 eq.) were dissolved in dry THF (1.4 mL per mmol X). The resulting solution was cooled to 0° C. and a solution of DEAD (40% wt in toluene, 1.0 eq.) in dry THF (0.5 mL per mmol X) was added dropwise. The reaction mixture was allowed to warm to rt and stirred under nitrogen for 15 h. The solvent was evaporated under reduced pressure, the residue suspended in $Et_2O$ and the flask placed on ice. The precipitate was filtered off and the filtrate was evaporated on silica. Pure compound XI was obtained by column chromatography using the Teledyne ISCO apparatus (cyclohexane:EtOAc).

Step 1b:

XII (1.0 eq.) and phthalimide (1.0 eq.) were dissolved in dry DMF (2.0 mL per mmol XII) and $K_2CO_3$ (1.0 eq.) was added. The reaction mixture was stirred at rt for 15 h, then diluted with EtOAc (5.0 mL per mmol XII) and filtered. The filtrate was evaporated under reduced pressure and the crude was used in the following step without further purification.

Step 2:

XI (1.0 eq) and hydrazine monohydrate (1.0 eq) in EtOH (8 mL per mmol XI) were refluxed for 3-12 h, depending on XI. A precipitate was formed, and the suspension was cooled to rt, filtered, acidified with conc. HCl, and filtered once more. The filtrate was concentrated under reduced pressure to afford amine III as the hydrochloride salt, which was used in the following step without further purification.

General Procedure VII: Synthesis of Compounds of Formula III (Scheme 3b)

Step 1:

MeCN (2.2 eq.) was dissolved in AcOH (1.0 mL per mmol X) and $H_2SO_4$ (0.15 mL per mmol X), then alcohol X (1.0 eq.) was slowly added at 0° C. The resulting solution was warmed up to 25° C. and stirred for 1 h, then poured on ice water (10 mL per mmol X). Sat. aq. $Na_2CO_3$ solution (10 mL per mmol X) was added, the aqueous layer extracted with $Et_2O$ (3×15 mL per mmol X) and the solvent of the combined organic layers was evaporated under reduced pressure to leave an off-white solid which was used in the following step without further purification.

Step 2:

The crude acetamide from step 1a was dissolved in ethylene glycol (5.0 mL per mmol X), then NaOH 50% (2.0 mL per mmol X) and water (2.0 mL per mmol X), are added and the solution was heated under microwave irradiation to 200° C. for 5 h. Sat. aq. $Na_2CO_3$ solution (10 mL per mmol X) was added, the aqueous layer extracted with $Et_2O$ (3×15 mL per mmol X) and the solvent of the combined organic layers was evaporated under reduced pressure. The residue was dissolved in $Et_2O$ (2.0 mL per mmol X) and the product was precipitated as hydrochloride salt by addition of HCl (4.0 M in dioxane, 0.5 mL per mmol X). The product was filtered off and washed with $Et_2O$ (5.0 mL per mmol X), to leave pure compound III.

General Procedure VIII: Synthesis of Compounds of Formula III (Scheme 3c)

Step 1:

$K_2CO_3$ (1.0 eq.) and the dihaloalkane (XIII, 1.0 eq.) were added to a solution of the appropriate thio-derivative XIV (1.0 eq.) in DMF (0.5 mL per mmol XIII). The reaction mixture was stirred under nitrogen atmosphere for 5 h at rt. The crude reaction mixture was filtered and concentrated under reduced pressure. Sat. aq. $NaHCO_3$ solution (1.0 mL per mmol XIII) was added and the mixture extracted with $Et_2O$ (3×1.0 mL per mmol XIII). The combined organic layers were evaporated on silica. Pure compound XV was obtained by column chromatography using the Teledyne ISCO apparatus (cyclohexane:EtOAc).

Step 2:

XV (1.0 eq.) and phthalimide (1.0 eq.) were dissolved in dry DMF (2.0 mL per mmol XV) and $K_2CO_3$ (1.0 eq.) was added. The reaction mixture was stirred at 100° C. for 3 h, then diluted with EtOAc (5.0 mL per mmol XV) and filtered. The filtrate was evaporated under reduced pressure and the crude XVI was used in the following step without further purification.

Step 3a:

XVI (1.0 eq.) was dissolved in DCM (5.0 mL per mmol XVI) and cooled to −20° C. m-CPBA (1.0 eq.) was added in small portions and the reaction was stirred at −20° C. for 2 h. Sat. aq. $Na_2S_2O_3$ solution (3.0 mL per mmol XVI) was added and the mixture extracted with DCM (3×5.0 mL per mmol XVI). The combined organic layers were evaporated on silica. Pure sulfoxide-containing derivative was obtained by column chromatography using the Teledyne ISCO apparatus (cyclohexane:EtOAc).

Step 3b:

XVI (1.0 eq.) was dissolved in DCM (5.0 mL per mmol XVI) and m-CPBA (2.5 eq.) was added in small portions and the reaction was stirred at rt for 2 h. Sat. aq. $Na_2S_2O_3$ solution (3.0 mL per mmol XVI) was added and the mixture extracted with DCM (3×5.0 mL per mmol XVI). The combined organic layers were evaporated on silica. Pure sulfone-containing derivative was obtained by column chromatography using the Teledyne ISCO apparatus (cyclohexane:EtOAc).

Step 4:

The appropriate amine III, containing sulfur, sulfoxide or sulfone, was obtained as hydrochloride salt according to the General Procedure VI (Step 2), and was used in the following step without further purification.

General Procedure IX: Synthesis of Compounds of Formula X (Scheme 4a)

Step 1:

In an oven-dried flask, to a stirred solution of oxalyl chloride (1.3 eq) in dry DCM (2.6 mL per mmol of XVII) at −78° C. under nitrogen atmosphere, DMSO (1.2 eq) was added in a fast manner. After 15 minutes a solution of alcohol XVII (1.0 eq) in dry DCM (1.2 mL per mmol of XVII) was added and the reaction mixture was stirred at −78° C. for 2 h, then $Et_3N$ (3.0 eq) was added. The reaction was stirred at rt and the solvent was evaporated under reduced pressure. The residue was taken up with diethyl ether and sat. aq. $NH_4Cl$ solution. The two phases were separated and the aqueous layer was extracted with diethyl ether (3×15 mL). The combined organic phases were dried over $Na_2SO_4$, and the solvent was evaporated under reduced pressure. The crude aldehyde XVIII was used in the next step without further purification.

Step 2:

In an oven-dried flask, to a stirred solution of the crude XVIII (1.0 eq) in dry THF (5 mL per mmol of XVIII) at −78° C. under nitrogen atmosphere, 1.6M solution of MeLi in $Et_2O$ (1.1 eq) was added dropwise. The reaction was stirred at −78° C. for 2 h, then at rt for 1 h. The reaction was then cooled to 0° C. and quenched with water. THF was evaporated under reduced pressure. The residue was taken up with DCM, dried over Na₂SO₄, and the solvent was evaporated under reduced pressure. Pure compound X was obtained by column chromatography using the Teledyne ISCO apparatus (cyclohexane:EtOAc).

General Procedure X: Synthesis of Compounds of Formula X (Scheme 4b)

Step 1:

Alcohol XVII (1.0 eq.) was dissolved in water (2 mL per mmol XVII) and conc H₂SO₄ (0.05 mL per mmol XVII), then KMnO₄ (2.0 eq.) was added in small portions at 0° C. After complete addition, the solution was stirred at 25° C. for 1 h, and then was turned basic by addition of solid NaOH. The manganese salts were removed by filtration and the filtrate was extracted with diethyl ether. The aqueous layer was acidified by addition of 2N HCl and the precipitate was filtered off and dried under reduced pressure to give the crude carboxylic acid which was used in the following step without further purification. The acid was dissolved in MeOH (2.0 mL per mmol of acid), and 5 drops of conc H₂SO₄ were added. The reaction was stirred at reflux for 1 h. The solution was then neutralized with sat. aq. Na₂CO₃ solution, extracted with EtOAc, and the solvent was evaporated on silica. The compound XIX was purified by column chromatography using the Teledyne ISCO apparatus (cyclohexane:EtOAc).

Step 2:

In an oven-dried flask, XIX (1.0 eq.) was dissolved in dry THF (2 mL per mmol XIX) and the solution was cooled to −78° C., then MeLi (2.5 eq.) was slowly added and the reaction was warmed to rt and stirred for 1 h. The solution was quenched with sat. aq. NH₄Cl solution and the aqueous phase was extracted with EtOAc. The two phases were separated and the aqueous layer was extracted with EtOAc (3×15 mL). The combined organic phases were dried over Na₂SO₄, evaporated on silica, and the compound was purified by column chromatography using the Teledyne ISCO apparatus (cyclohexane:EtOAc).

Intermediate 1. 7-bromo-3H-1,3-benzoxazol-2-one

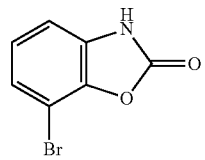 [SMILES: O=c1[nH]c2cccc(Br)c2o1]

The title compound was obtained according to the General Procedure V, starting from 2-amino-6-bromo-phenol (1.88 g, 10.0 mmol) and 1,1'-carbonyldiimidazole (1.95 g, 12.0 mmol). Orange solid (1.85 g, 86%). ¹H NMR (DMSO-d₆) δ 7.06-7.14 (m, 2H), 7.25-7.32 (m, 1H), 11.93 (s, 1H). MS (ESI) m/z: 212 [M-H]⁻.

Intermediate 2. 7-bromo-5-chloro-3H-1,3-benzoxazol-2-one

The title compound was obtained according to the General Procedure V, starting from 2-amino-6-bromo-4-chlorophenol (1.0 g, 4.50 mmol) and 1,1'-carbonyldiimidazole (1.10 g, 6.74 mmol). White powder (740 mg, 89%). ¹H NMR (400 MHz, DMSO-d₆) δ 7.19 (d, J=2.0 Hz, 1H), 7.42 (d, J=1.9 Hz, 1H), 12.15 (s, 1H). MS (ESI) m/z: 246 [M-H]⁻.

Intermediate 3. 6-(4-fluorophenyl)-3H-1,3-benzoxazol-2-one

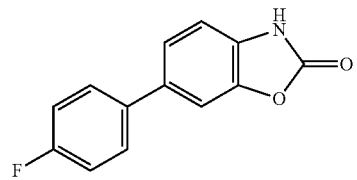 [SMILES: O=c1[nH]c2ccc(-c3ccc(F)cc3)cc2o1]

The title compound was obtained according to the General Procedure II, starting from 6-bromobenzoxazolone (500 mg, 2.34 mmol) and (4-fluorophenyl)boronic acid (490 mg, 3.50 mmol). White solid (450 mg, 42%). ¹H NMR (400 MHz, CDCl₃) δ 7.08 (m, 3H), 7.33 (dd, J=8.1, 1.6 Hz, 1H), 7.39 (d, J=1.4 Hz, 1H), 7.47-7.52 (m, 2H), 7.91 (s, 1H). MS (ESI) m/z: 228 [M-H]⁻.

Intermediate 4. 5-(4-fluorophenyl)-3H-1,3-benzoxazol-2-one

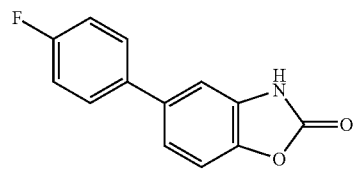 [SMILES: O=c1[nH]c2cc(-c3ccc(F)cc3)ccc2o1]

The title compound was obtained according to the General Procedure II, starting from 5-bromobenzoxazolone (600 mg, 2.80 mmol) and (4-fluorophenyl)boronic acid (590 mg, 4.20 mmol). White powder (0.32 g, 50%). ¹H NMR (400 MHz, DMSO-d₆) δ 7.24-7.32 (m, 3H), 7.34 (d, J=1.7 Hz, 1H), 7.36 (d, J=8.3 Hz, 1H), 7.62-7.73 (m, 2H), 11.75 (s, 1H). MS (ESI) m/z: 228 [M-H]⁻.

Intermediate 5. 5-(2-fluorophenyl)-3H-1,3-benzoxazol-2-one

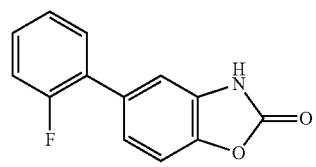 [SMILES: O=c1[nH]c2cc(-c3ccccc3F)ccc2o1]

The title compound was obtained according to the General Procedure II, starting from 5-bromobenzoxazolone (200 mg, 0.93 mmol) and (2-fluorophenyl)boronic acid (190 mg, 1.40 mmol). White solid (154 mg, 72%). ¹H NMR (400 MHz, DMSO-d₆) δ 7.19-7.26 (m, 2H), 7.27-7.35 (m, 2H), 7.39 (d, J=8.5 Hz, 1H), 7.38-7.45 (m, 1H), 7.53 (td, J=7.9, 1.7 Hz, 1H), 11.77 (s, 1H). MS (ESI) m/z: 228 [M-H]⁻.

Intermediate 6. 5-[4-(trifluoromethyl)phenyl]-3H-1,3-benzoxazol-2-one

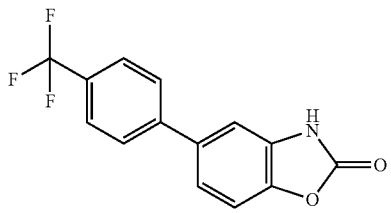 [SMILES: O=c1[nH]c2cc(-c3ccc(C(F)(F)F)cc3)ccc2o1]

The title compound was obtained according to the General Procedure II, starting from 5-bromobenzoxazolone (200 mg, 0.93 mmol) and (4-trifluoromethyl)phenyl boronic acid (270 mg, 1.40 mmol). White solid (98 mg, 38%). $^1$H NMR (400 MHz, DMSO-$d_6$) δ 7.39 (d, J=1.7 Hz, 1H), 7.41 (d, J=8.4 Hz, 1H), 7.45 (dd, J=8.4, 1.7 Hz, 1H), 7.79-7.81 (m, 2H), 7.86-7.88 (m, 2H), 11.85 (s, 1H). MS (ESI) m/z: 278 [M-H]⁻.

Intermediate 7. 7-(4-fluorophenyl)-3H-1,3-benzoxazol-2-one

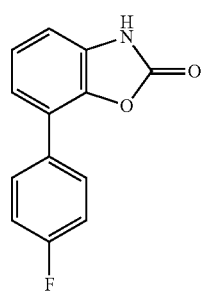 [SMILES: O=c1[nH]c2cccc(-c3ccc(F)cc3)c2o1]

The title compound was obtained according to the General Procedure II, starting from Intermediate 1 (200 mg, 0.93 mmol) and (4-fluorophenyl)boronic acid (190 mg, 1.40 mmol). Yellow powder (104 mg, 49%). $^1$H NMR (400 MHz, DMSO-$d_6$) δ 7.08 (dd, J=8.0, 1.2 Hz, 1H), 7.24 (t, J=8.0 Hz, 1H), 7.31 (dd, J=8.0, 1.2 Hz, 1H), 7.33-7.39 (m, 2H), 7.75-7.86 (m, 2H), 11.78 (s, 1H). MS (ESI) m/z: 228 [M-H]⁻.

Intermediate 8. 7-(4-methoxyphenyl)-3H-1,3-benzoxazol-2-one

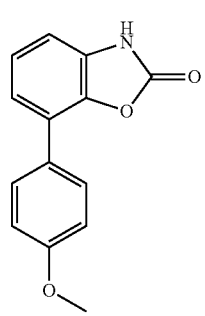 [SMILES: COc1ccc(-c2cccc3[nH]c(=O)oc23)cc1]

The title compound was obtained according to the General Procedure II, starting from Intermediate 1 (200 mg, 0.93 mmol) and (4-methoxyphenyl)boronic acid (210 mg, 1.40 mmol). Yellow powder (124 mg, 55%). $^1$H NMR (400 MHz, DMSO-$d_6$) δ 3.81 (s, 3H), 7.03 (dd, J=7.8, 1.2 Hz, 1H), 7.05-7.13 (m, 2H), 7.21 (t, J=7.8 Hz, 1H), 7.25-7.32 (m, 1H), 7.68-7.73 (m, 2H), 11.72 (s, 1H). MS (ESI) m/z: 242 [M-H]⁺; 279 [M-NH$_4$]⁺. MS (ESI) m/z: 240 [M-H]⁻.

Intermediate 9. 5-(4-methoxybenzoyl)-3H-1,3-benzoxazol-2-one

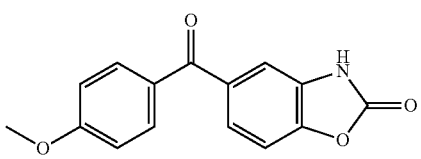 [SMILES: COc1ccc(C(=O)c2ccc3oc(=O)[nH]c3c2)cc1]

The title compound was obtained according to the General Procedure IV, starting from 5-bromobenzoxazolone (300 mg, 1.40 mmol) and 4-methoxybenzoyl chloride (735 mg, 3.08 mmol). White solid (84 mg, 22%). $^1$H NMR (400 MHz, DMSO-$d_6$) δ 3.87 (s, 3H), 7.06-7.13 (m, 2H), 7.35-7.38 (m, 1H), 7.44-7.45 (m, 1H), 7.46 (d, J=1.5 Hz, 1H), 7.73-7.78 (m, 2H), 11.88 (s, 1H). MS (ESI) m/z: 268 [M-H]⁻.

Intermediate 10. 6-(4-methoxybenzoyl)-3H-1,3-benzoxazol-2-one

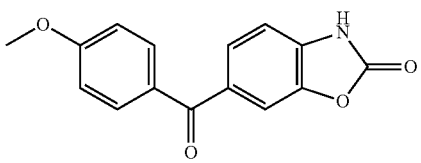 [SMILES: COc1ccc(C(=O)c2ccc3[nH]c(=O)oc3c2)cc1]

The title compound was obtained according to the General Procedure IV, starting from 6-bromobenzoxazolone (300 mg, 1.40 mmol) and 4-methoxybenzoyl chloride (735 mg, 3.08 mmol). White solid (69 mg, 18%). $^1$H NMR (400 MHz, DMSO-$d_6$) δ 3.87 (s, 3H), 7.06-7.13 (m, 2H), 7.23 (d, J=8.1 Hz, 1H), 7.55 (dd, J=8.1, 1.5 Hz, 1H), 7.61 (d, J=1.4 Hz, 1H), 7.69-7.78 (m, 2H), 12.08 (s, 1H). MS (ESI) m/z: 268 [M-H]⁻.

Intermediate 11. (±)-6-[hydroxy-(4-methoxyphenyl)methyl]-3H-1,3-benzoxazol-2-one

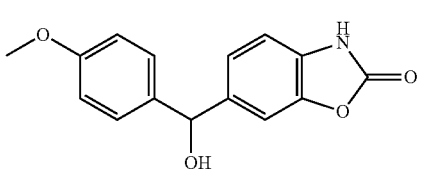 [SMILES: COc1ccc(C(O)c2ccc3[nH]c(=O)oc3c2)cc1]

The title compound was obtained according to the General Procedure IV, starting from 6-bromobenzoxazolone (321 mg, 1.50 mmol) and 4-methoxybenzaldehyde (450 mg, 3.30 mmol). White solid (168 mg, 41%). $^1$H NMR (400 MHz, DMSO-d$_6$) δ 3.72 (s, 3H), 5.67 (bs, 1H), 5.80-5.90 (m, 1H), 6.83-6.89 (m, 2H), 7.00 (d, J=8.0 Hz, 1H), 7.11 (dd, J=8.1, 1.1 Hz, 1H), 7.25 (d, J=1.1 Hz, 1H), 7.25-7.30 (m, 2H), 11.56 (s, 1H). MS (ESI) m/z: 270 [M-H]$^-$.

Intermediate 12.
7-(4-fluorobenzoyl)-3H-1,3-benzoxazol-2-one

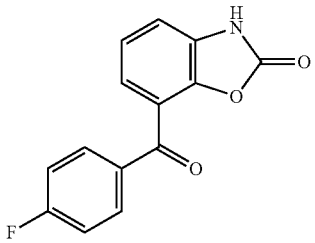 [SMILES: O=C(c1ccc(F)cc1)c1cccc2[nH]c(=O)oc12]

The title compound was obtained according to the General Procedure IV, starting from Intermediate 1 (300 mg, 1.40 mmol) and 4-fluorobenzoyl chloride (317 mg, 2.00 mmol). Off-white solid (44 mg, 12%). $^1$H NMR (400 MHz, DMSO-d$_6$) δ 7.28-7.43 (m, 5H), 7.88-7.94 (m, 2H), 11.96 (s, 1H). MS (ESI) m/z: 256 [M-H]$^-$.

Intermediate 13. 5-chloro-7-(4-fluorophenyl)-3H-1,3-benzoxazol-2-one

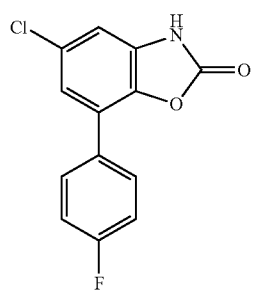 [SMILES: O=c1[nH]c2cc(Cl)cc(-c3ccc(F)cc3)c2o1]

The title compound was obtained according to the General Procedure II, starting from Intermediate 2 (150 mg, 0.60 mmol) and (4-fluorophenyl)boronic acid (130 mg, 0.90 mmol). Pale yellow powder (86 mg, 54%). $^1$H NMR (400 MHz, DMSO-d$_6$) δ 7.15 (d, J=2.1 Hz, 1H), 7.33-7.40 (m, 3H), 7.78-7.88 (m, 2H), 11.99 (s, 1H). MS (ESI) m/z: 262 [M-H]$^-$.

Intermediate 14.
2-(5-phenylpentyl)isoindoline-1,3-dione

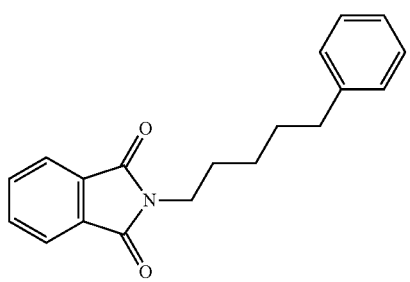 [SMILES: O=C1c2ccccc2C(=O)N1CCCCCc1ccccc1]

The title compound was obtained according to the General Procedure VI (Step 1b), starting from (5-bromopentyl)benzene (1.54 g, 6.79 mmol) and phthalimide (1.0 g, 6.79 mmol). White solid (1.73 g, 87%). $^1$H NMR (400 MHz, DMSO-d$_6$) δ 1.21-1.34 (m, 2H), 1.49-1.69 (m, 4H), 2.52-2.56 (m, 1H), 3.55 (t, J=7.1 Hz, 2H), 7.08-7.17 (m, 3H), 7.17-7.28 (m, 2H), 7.79-7.91 (m, 4H). MS (ESI) m/z: 294 [M-H]$^+$; 311 [M-NH$_4$]$^+$. MS (ESI) m/z: 292 [M-H]$^-$.

Intermediate 15. 5-phenylpentan-1-amine hydrochloride

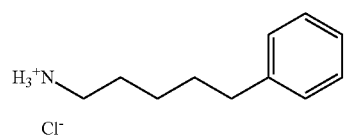

The title compound was obtained according to the General Procedure VI (Step 2), starting from Intermediate 14 (1.14 g, 5.00 mmol). White solid (807 mg, 81%). $^1$H NMR (400 MHz, CDCl$_3$) δ 1.38-1.51 (m, 2H), 1.60-1.72 (m, 2H), 1.75-1.88 (m, 2H), 2.62 (t, J=7.6 Hz, 2H), 2.94-3.03 (m, 2H), 7.13-7.21 (m, 3H), 7.25-7.31 (m, 2H), 8.27 (s, 3H). MS (ESI) m/z: 164 [M]$^+$.

Intermediate 16.
2-(6-phenylhexyl)isoindoline-1,3-dione

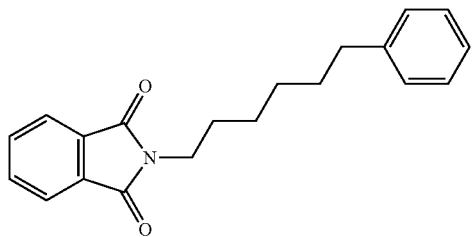 [SMILES: O=C1c2ccccc2C(=O)N1CCCCCCc1ccccc1]

The title compound was obtained according to the General Procedure VI (Step 1a), starting from 6-phenylhexan-1-ol (1.0 g, 5.61 mmol). White solid (1.35 g, 78%). $^1$H NMR (400 MHz, DMSO-d$_6$) δ 1.23-1.38 (m, 4H), 1.47-1.64 (m, 4H), 2.53 (t, J=8.0 Hz, 2H), 3.55 (t, J=7.1 Hz, 2H), 7.10-7.18 (m, 3H), 7.20-7.30 (m, 2H), 7.80-7.91 (m, 4H). MS (ESI) m/z: 308 [M-H]$^+$.

Intermediate 17. 6-phenylhexan-1-amine hydrochloride

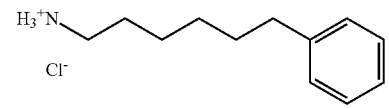

The title compound was obtained according to the General Procedure VI (Step 2), starting from Intermediate 16 (1.35 g, 4.40 mmol). White solid (470 mg, crude). $^1$H NMR (400 MHz, DMSO-d$_6$) δ 1.18-1.41 (m, 4H), 1.45-1.67 (m, 4H), 2.57 (t, J=8.0 Hz, 2H), 2.68-2.80 (m, 2H), 7.10-7.23 (m, 3H), 7.23-7.33 (m, 2H), 7.74-7.98 (m, 3H). MS (ESI) m/z: 178 [M-H]⁺.

Intermediate 18. 5-phenylpentanal

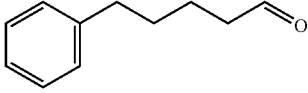 [SMILES: O=CCCCCc1ccccc1]

The title compound was obtained according to the General Procedure IX (Step 1), starting from the commercial 5-phenylpentan-1-ol (600 mg, 3.65 mmol). Colorless oil (560 mg, crude). ¹H NMR (400 MHz, CDCl₃) δ 1.64-1.72 (m, 4H), 2.40-2.52 (m, 2H), 2.61-2.69 (m, 2H), 7.14-7.21 (m, 4H), 7.25-7.32 (m, 1H), 9.76 (t, J=1.7 Hz, 1H). MS (ESI) m/z: non-ionizable compound under routine conditions used.

Intermediate 19. (±)-6-phenylhexan-2-ol

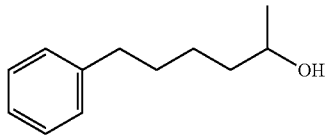

The title compound was obtained according to the General Procedure IX (Step 2), starting from Intermediate 18 (560 mg, 3.46 mmol). Colorless oil (200 mg, 31% over two steps). ¹H NMR (400 MHz, CDCl₃) δ 1.18 (d, J=6.2 Hz, 3H), 1.41-1.56 (m, 4H), 1.59-1.76 (m, 2H), 2.63 (t, J=7.7 Hz, 2H), 3.74-3.87 (m, 1H), 7.14-7.21 (m, 3H), 7.26-7.31 (m, 2H). MS (ESI) m/z: 196 [M-NH₄]⁺.

Intermediate 20. (±)-2-(1-methyl-5-phenyl-pentyl)isoindoline-1,3-dione

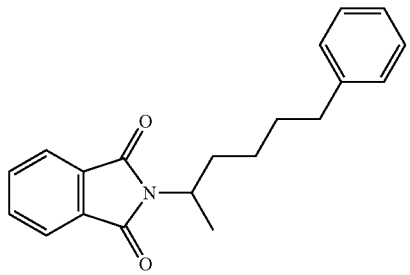 [SMILES: CC(CCCCc1ccccc1)N1C(=O)c2ccccc2C1=O]

The title compound was obtained according to the General Procedure VI (Step 1a), starting from Intermediate 19 (200 mg, 1.13 mmol). Colorless oil (190 mg, 55%). ¹H NMR (400 MHz, CDCl₃) δ 1.20-1.41 (m, 2H), 1.46 (d, J=6.9 Hz, 3H), 1.58-1.70 (m, 2H), 1.71-1.86 (m, 1H), 2.00-2.24 (m, 1H), 2.45-2.67 (m, 2H), 4.27-4.44 (m, 1H), 7.09-7.16 (m, 3H), 7.18-7.26 (m, 2H), 7.70 (dd, J=5.4, 3.1 Hz, 2H), 7.82 (dd, J=5.4, 3.1 Hz, 2H). MS (ESI) m/z: 308 [M-H]⁺, 325 [M-NH₄]⁺, 330 [M-Na]⁺.

Intermediate 21. (±)-(1-methyl-5-phenyl-pentyl)-1-amine hydrochloride

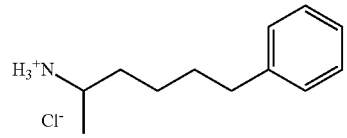

The title compound was obtained according to the General Procedure VI (Step 2) starting from Intermediate 20 (190 mg, 0.62 mmol). Pale yellow solid (100 mg, crude). ¹H NMR (400 MHz, DMSO-d₆) δ 1.15 (d, J=6.5 Hz, 3H), 1.27-1.38 (m, 2H), 1.40-1.49 (m, 2H), 1.52-1.61 (m, 2H), 2.58 (dt, J=8.2, 3.7 Hz, 2H), 3.07-3.17 (m, 1H), 7.14-7.22 (m, 3H), 7.24-7.32 (m, 2H), 7.82-7.98 (m, 3H).

Intermediate 22. methyl 5-phenylpentanoate

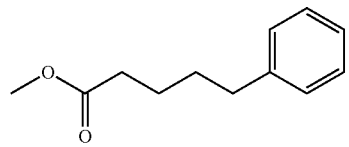

The title compound was obtained according to the General Procedure X (Step 1) starting from 5-phenylpentan-1-ol (3.28 g, 20.0 mmol). Colorless liquid (1.77 g, 46%). ¹H NMR (400 MHz, CDCl₃) δ 1.65-1.74 (m, 4H), 2.36 (t, J=7.1 Hz, 2H), 2.65 (t, J=7.1 Hz, 2H), 3.69 (s, 3H), 7.18-7.23 (m, 3H), 7.27-7.33 (m, 2H). MS (ESI) m/z: 193 [M-H]⁺.

Intermediate 23. 2-methyl-6-phenyl-hexan-2-ol

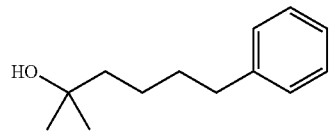

The title compound was obtained according to the General Procedure X (Step 2) starting from Intermediate 22 (1.76 g, 9.15 mmol). Colorless liquid (940 mg, 53%). ¹H NMR (400 MHz, CDCl₃) δ 1.23 (s, 6H), 1.38-1.48 (m, 2H), 1.50-1.61 (m, 2H), 1.62-1.70 (m, 2H), 2.66 (t, J=7.8 Hz, 2H), 7.18-7.23 (m, 3H), 7.28-7.33 (m, 2H). MS (ESI) m/z: non-ionizable compound under routine conditions used.

Intermediate 24. (1,1-dimethyl-5-phenyl-pentyl)-1-amine hydrochloride

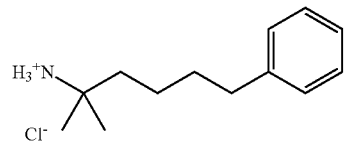

The title compound was obtained according to the General Procedure VII (Step 1 and 2) starting from Intermediate 23 (385 mg, 2.0 mmol). Colorless solid (181 mg, 40%). $^1$H NMR (400 MHz, CDCl$_3$) δ 1.43 (s, 6H), 1.45-1.54 (m, 2H), 1.61-1.71 (m, 2H), 1.73-1.80 (m, 2H), 2.63 (t, J=7.6 Hz, 2H), 7.18 (dd, J=11.5, 7.6 Hz, 3H), 7.25-7.31 (m, 2H), 8.39 (s, 3H). MS (ESI) m/z: 192 [M-H]$^+$.

Intermediate 25. 4-phenylsulfanylbutylammonium chloride

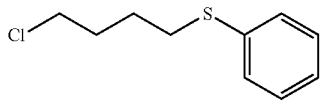 [SMILES: ClCCCCSc1ccccc1]

The title compound was obtained according to the General Procedure VIII (Step 1) starting from 1-bromo-4-chlorobutane (8.57 g, 50.0 mmol) and thiophenol (5.51 g, 50.0 mmol). Colorless liquid (8.06 g, 80%). $^1$H NMR (400 MHz, CDCl$_3$) δ 1.79-1.88 (m, 2H), 1.91-1.99 (m, 2H), 2.98 (t, J=7.1 Hz, 2H), 3.57 (t, J=6.5 Hz, 2H), 7.17-7.24 (m, 1H), 7.28-7.34 (m, 2H), 7.35-7.39 (m, 2H). MS (ESI) m/z: non-ionizable compound under routine conditions used.

Intermediate 26. (±)-2-[4-(benzenesulfinyl)butyl]isoindoline-1,3-dione

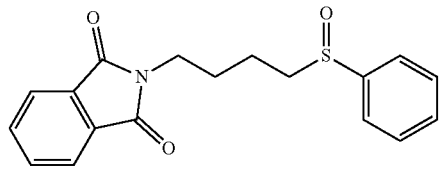 [SMILES: O=C1c2ccccc2C(=O)N1CCCCS(=O)c1ccccc1]

The title compound was obtained according to the General Procedure VIII (Step 2 and 3a) starting from Intermediate 25 (660 mg, 3.30 mmol) and phthalimide (490 mg, 3.30 mmol). Colourless solid (820 mg, 76%). $^1$H NMR (400 MHz, CDCl$_3$) δ 1.64-1.73 (m, 1H), 1.77-1.90 (m, 3H), 2.80-2.94 (m, 2H), 3.71 (t, J=6.8 Hz, 2H), 7.46-7.56 (m, 3H), 7.61-7.65 (m, 2H), 7.74 (dd, J=5.4, 3.1 Hz, 2H), 7.86 (dd, J=5.4, 3.1 Hz, 2H). MS (ESI) m/z: 328 [M-H]$^+$.

Intermediate 27. 2-[4-(benzenesulfonyl)butyl]isoindoline-1,3-dione

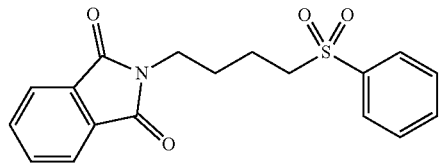 [SMILES: O=C1c2ccccc2C(=O)N1CCCCS(=O)(=O)c1ccccc1]

The title compound was obtained according to the General Procedure VIII (Step 2 and 3b) starting from Intermediate 25 (660 mg, 3.30 mmol) and phthalimide (490 mg, 3.30 mmol). Colorless solid (990 mg, 87%). $^1$H NMR (400 MHz, CDCl$_3$) δ 1.74-1.86 (m, 4H), 3.10-3.22 (m, 2H), 3.68 (t, J=6.5 Hz, 2H), 7.55-7.61 (m, 2H), 7.64-7.69 (m, 1H), 7.74 (dd, J=5.5, 3.1 Hz, 2H), 7.85 (dd, J=5.4, 3.1 Hz, 2H), 7.91-7.94 (m, 2H). MS (ESI) m/z: 344 [M-H]$^+$.

Intermediate 28. 4-chlorobutylsulfanylbenzene

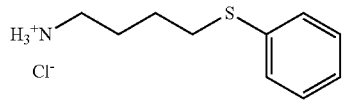

The title compound was obtained according to the General Procedure VIII (Step 2 and 4) starting from Intermediate 25 (803 mg, 4.00 mmol). Colorless solid (370 mg, 42%). $^1$H NMR (400 MHz, MeOD) δ 1.68-1.84 (m, 4H), 2.88-2.94 (m, 2H), 3.01 (t, J=6.9 Hz, 2H), 4.64 (s, 3H), 7.18-7.23 (m, 1H), 7.29-7.34 (m, 2H), 7.35-7.39 (m, 2H). MS (ESI) m/z: 218 [M-H]$^+$.

Intermediate 29. (±)-4-(benzenesulfinyl)butylammonium chloride

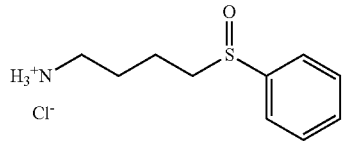

The title compound was obtained according to the General Procedure VIII (Step 4) starting from Intermediate 26 (820 mg, 2.51 mmol). Colorless solid (388 mg, 66%). $^1$H NMR (400 MHz, MeOD) δ 1.68-1.78 (m, 1H), 1.78-1.91 (m, 3H), 2.90-2.99 (m, 3H), 3.01-3.10 (m, 1H), 4.95 (s, 3H), 7.60-7.66 (m, 3H), 7.70-7.74 (m, 2H). MS (ESI) m/z: 234 [M-H]$^+$.

Intermediate 30. 4-(benzenesulfonyl)butylammonium chloride

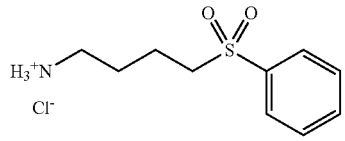

The title compound was obtained according to the General Procedure VIII (Step 4) starting from Intermediate 27 (920 mg, 2.68 mmol). Colorless solid (480 mg, 71%). $^1$H NMR (400 MHz, MeOD) δ 1.77-1.84 (m, 4H), 2.92-2.97 (m, 2H), 3.28-3.32 (m, 2H), 4.84 (s, 3H), 7.65-7.71 (m, 2H), 7.74-7.80 (m, 1H), 7.94-7.98 (m, 2H). MS (ESI) m/z: 250 [M-H]$^+$.

The following Examples provide embodiments illustrative of the present invention.

Example 1. 6-(4-fluorophenyl)-2-oxo-N-(5-phenylpentyl)-1,3-benzoxazole-3-carboxamide The title compound was obtained according to the General Procedure I (Method A), starting from Intermediate 3

(50 mg, 0.22 mmol) and Intermediate 15 (65 mg, 0.33 mmol). White powder (53 mg, 57%; 79% brsm). $^1$H NMR (400 MHz, CDCl$_3$) δ 1.37-1.52 (m, 2H), 1.63-1.78 (m, 4H), 2.56-2.74 (m, 2H), 3.44 (td, J=7.2, 5.7 Hz, 2H), 7.11-7.16 (m, 2H), 7.16-7.20 (m, 3H), 7.24-7.31 (m, 2H), 7.40 (d, J=1.7 Hz, 1H), 7.44 (dd, J=8.3, 1.7 Hz, 1H), 7.52 (dd, J=8.8, 5.2 Hz, 2H), 8.04 (t, J=5.8 Hz, 1H), 8.10 (d, J=8.3 Hz, 1H). $^{13}$C NMR (101 MHz, CDCl$_3$) δ 26.56, 29.44, 31.16, 35.89, 40.38, 108.55, 115.89 (d, J=7.9 Hz), 116.14, 123.91, 125.86, 127.30, 128.43, 128.52, 128.85 (d, J=8.2 Hz), 137.50, 141.40, 142.38, 142.45, 149.82, 153.32, 162.81 (d, J=247.2 Hz). MS (ESI) m/z: non-ionizable compound under routine conditions used.

Example 2. 6-(2-fluorophenyl)-2-oxo-N-(5-phenylpentyl)-1,3-benzoxazole-3-carboxamide The title compound was obtained according to the General Procedure I (Method A), starting from Intermediate 5 (50 mg, 0.22 mmol) and Intermediate 15 (65 mg, 0.33 mmol). White powder (48 mg, 52%; 63% brsm). $^1$H NMR (400 MHz, CDCl$_3$) δ 1.40-1.49 (m, 2H), 1.63-1.74 (m, 4H), 2.60-2.69 (m, 2H), 3.43 (td, J=7.1, 5.7 Hz, 2H), 7.13-7.20 (m, 4H), 7.22 (dd, J=7.5, 1.2 Hz, 1H), 7.24-7.28 (m, 2H), 7.30 (d, J=8.6 Hz, 1H), 7.32-7.38 (m, 1H), 7.40-7.47 (m, 2H), 8.06 (t, J=5.6 Hz, 1H), 8.28 (t, J=1.5 Hz, 1H). $^{13}$C NMR (101 MHz, CDCl$_3$) δ 26.55, 29.43, 31.16, 35.88, 40.36, 109.84, 116.18, 116.31-116.49 (m), 124.56 (d, J=3.7 Hz), 125.65 (d, J=3.4 Hz), 125.84, 128.21 (d, J=5.3 Hz), 128.32, 128.42, 128.51, 129.54 (d, J=8.4 Hz), 131.02 (d, J=3.2 Hz), 133.19, 141.31 (d, J=8.8 Hz), 142.46, 149.86, 153.39, 159.72 (d, J=248.2 Hz). MS (ESI) m/z: non-ionizable compound under routine conditions used.

Example 3. 2-oxo-N-(6-phenylhexyl)-5-[4-(trifluoromethyl)phenyl]-1,3-benzoxazole-3-carboxamide The title compound was obtained according to the General Procedure I (Method A), starting from Intermediate 6 (50 mg, 0.18 mmol) and Intermediate 17 (57 mg, 0.27 mmol). White powder (36 mg, 41%; 62% brsm). $^1$H NMR (400 MHz, CDCl$_3$) δ 0.92-1.07 (m, 4H), 1.14-1.30 (m, 4H), 2.10-2.29 (m, 2H), 3.00 (td, J=7.1, 5.8 Hz, 2H), 6.70-6.76 (m, 2H), 6.79-6.86 (m, 3H), 6.89 (d, J=8.4 Hz, 1H), 7.03 (dd, J=8.4, 1.9 Hz, 1H), 7.24-7.28 (m, 4H), 7.63 (t, J=5.8 Hz, 1H), 7.92 (d, J=1.9 Hz, 1H). $^{13}$C NMR (101 MHz, CDCl$_3$) δ 26.85, 29.00, 29.50, 31.45, 35.97, 40.48, 110.38, 114.68, 123.81, 124.18 (q, J=281.6 Hz), 125.79, 125.95 (q, J=3.6 Hz), 127.75, 128.40, 128.52, 128.84, 129.92 (q, J=14.4 Hz), 137.36, 141.85, 142.70, 143.64, 149.88, 153.31. MS (ESI) m/z: non-ionizable compound under routine conditions used.

Example 4. 7-(4-fluorophenyl)-2-oxo-N-(6-phenylhexyl)-1,3-benzoxazole-3-carboxamide The title compound was obtained according to the General Procedure I (Method A), starting from Intermediate 7 (50 mg, 0.22 mmol) and Intermediate 17 (70 mg, 0.33 mmol). White powder (36 mg, 38%; 64% brsm). $^1$H NMR (400 MHz, CDCl$_3$) δ 1.36-1.47 (m, 4H), 1.60-1.70 (m, 4H), 2.62 (t, J=7.5 Hz, 2H), 3.39-3.47 (m, 2H), 7.14-7.22 (m, 5H), 7.24-7.30 (m, 2H), 7.30-7.38 (m, 2H), 7.65-7.72 (m, 2H), 8.07 (t, J=7.2, 2.0 Hz, 1H), 8.09-8.12 (m, 1H). $^{13}$C NMR (101 MHz, CDCl$_3$) δ 26.86, 29.00, 29.51, 31.45, 35.98, 40.47, 114.64, 116.02 (d, J=21.4 Hz), 124.20, 125.52, 125.78, 128.39, 128.52, 128.72, 130.26 (d, J=8.2 Hz), 135.83, 142.72, 149.87, 153.30, 160.51 (d, J=239.5 Hz). MS (ESI) m/z: non-ionizable compound under routine conditions used.

Example 5. 7-(4-methoxyphenyl)-2-oxo-N-(5-phenylpentyl)-1,3-benzoxazole-3-carboxamide The title compound was obtained according to the General Procedure I (Method A), starting from Intermediate 8 (40 mg, 0.16 mmol) and Intermediate 15 (48 mg, 0.24 mmol). White powder (11 mg, 16%). $^1$H NMR (400 MHz, CDCl$_3$) δ 1.40-1.53 (m, 2H), 1.62-1.75 (m, 4H), 2.64 (t, J=8.0 Hz, 2H), 3.32-3.50 (m, 2H), 3.87 (s, 3H), 6.99-7.06 (m, 2H), 7.14-7.21 (m, 3H), 7.24-7.28 (m, 2H), 7.31 (t, J=8.0 Hz, 1H), 7.37 (dd, J=8.0, 1.3 Hz, 1H), 7.61-7.72 (m, 2H), 8.02 (dd, J=8.0, 1.3 Hz, 1H), 8.11 (t, J=5.3 Hz, 1H). $^{13}$C NMR (101 MHz, CDCl$_3$) δ 26.57, 29.46, 31.16, 35.90, 40.38, 55.52, 113.94, 114.45, 123.97, 125.42, 125.77, 125.85, 126.75, 128.43, 128.53, 128.67, 129.70, 138.23, 142.48, 149.98, 153.40, 159.92. MS (ESI) m/z: non-ionizable compound under routine conditions used.

Example 6. 6-(4-methoxybenzoyl)-2-oxo-N-(5-phenylpentyl)-1,3-benzoxazole-3-carboxamide The title compound was obtained according to the General Procedure I (Method A), starting from Intermediate 10 (20 mg, 0.074 mmol) and Intermediate 15 (22 mg, 0.11 mmol). White powder (14 mg, 42%; 69% brsm). $^1$H NMR (400 MHz, CDCl$_3$) δ 1.37-1.52 (m, 2H), 1.63-1.77 (m, 4H), 2.64 (t, J=8.4 Hz, 2H), 3.34-3.58 (m, 2H), 3.90 (s, 3H), 6.93-7.03 (m, 2H), 7.14-7.21 (m, 3H), 7.25-7.30 (m, 2H), 7.70-7.74 (m, 2H), 7.75-7.87 (m, 2H), 8.04 (t, J=5.6 Hz, 1H), 8.16 (d, J=8.7 Hz, 1H). $^{13}$C NMR (101 MHz, CDCl$_3$) δ 26.53, 29.39, 31.13, 35.87, 40.47, 55.70, 111.44, 113.89, 115.04, 125.87, 127.70, 128.43, 128.51, 129.82, 131.12, 132.60, 134.95, 141.67, 142.41, 149.52, 153.16, 163.55, 193.72. MS (ESI) m/z: 459 [M-H]$^+$.

Example 7. (±)-6-[hydroxy-(4-methoxyphenyl)methyl]-2-oxo-N-(5-phenylpentyl)-1,3-benzoxazole-3-carboxamide The title compound was obtained according to the General Procedure I (Method A), starting from Intermediate 11 (30 mg, 0.11 mmol) and Intermediate 15 (33 mg, 0.17 mmol). White solid (14 mg, 28%). $^1$H NMR (400 MHz, CDCl$_3$) δ 1.41-1.50 (m, 2H), 1.64-1.75 (m, 4H), 2.26 (s, 1H), 2.65 (t, J=7.6 Hz, 2H), 3.39-3.47 (m, 2H), 3.82 (s, 3H), 5.87 (s, 1H), 6.88-6.92 (m, 2H), 7.16-7.22 (m, 3H), 7.26-7.32 (m, 5H), 7.34-7.36 (m, 1H), 8.02 (d, J=8.3 Hz, 1H), 8.03-8.07 (m, 1H). $^{13}$C NMR (101 MHz, CDCl$_3$) δ 26.41, 29.30, 31.03, 35.75, 40.20, 47.57, 55.32, 75.30, 107.96, 110.49, 114.09, 115.25, 123.07, 125.71, 127.04, 127.91, 128.29, 128.38, 141.24, 141.87, 148.88, 153.29, 159.35. MS (ESI) m/z: 461 [M-H]$^+$.

Example 8. 5-(4-methoxybenzoyl)-2-oxo-N-(6-phenylhexyl)-1,3-benzoxazole-3-carboxamide The title compound was obtained according to the General Procedure I (Method A), starting from Intermediate 9 (30 mg, 0.11 mmol) and Intermediate 17 (35 mg, 0.17 mmol). Colorless oil (7 mg, 13%). $^1$H NMR (400 MHz, CDCl$_3$) δ 1.38-1.46 (m, 4H), 1.61-1.70 (m, 4H), 2.63 (t, J=7.6 Hz, 2H), 3.40-3.46 (m, 2H), 3.92 (s, 3H), 6.97-7.02 (m, 2H), 7.16-7.21 (m, 3H), 7.26-7.31 (m, 2H), 7.37 (d, J=8.4 Hz, 1H), 7.77 (dd, J=8.4, 1.7 Hz, 1H), 7.80-7.86 (m, 2H), 8.01 (t, J=5.4 Hz, 1H), 8.49 (d, J=1.6 Hz, 1H). $^{13}$C NMR (101 MHz, CDCl$_3$) δ 26.70, 28.84, 29.34, 31.29, 35.82, 40.36, 55.53, 109.85, 113.77, 117.32, 125.65, 126.85, 127.71, 128.26, 128.38, 129.77, 132.49, 135.57, 142.55, 143.99, 149.39, 163.42, 175.07, 193.96. MS (ESI) m/z: 473 [M-H]$^+$.

Example 9. 7-(4-fluorobenzoyl)-2-oxo-N-(5-phenyl-pentyl)-1,3-benzoxazole-3-carboxamide The title compound was obtained according to the General Procedure I (Method A), starting from Intermediate 12 (39 mg, 0.15 mmol) and Intermediate 15 (36 mg, 0.18 mmol). Colorless oil (12 mg, 18%). $^1$H NMR (400 MHz, CDCl$_3$) δ 1.41-1.51 (m, 2H), 1.65-1.76 (m, 4H), 2.66 (t, J=7.7 Hz, 2H), 3.42-3.49 (m, 2H), 7.16-7.23 (m, 5H), 7.26-7.32 (m, 2H), 7.41 (dd, J=8.0, 7.9 Hz, 1H), 7.51 (dd, J=7.9, 1.0 Hz, 1H), 7.90 (dd, J=8.7, 5.4 Hz, 2H), 8.03 (t, J=4.9 Hz, 1H), 8.29-8.36 (m, 1H). $^{13}$C NMR (101 MHz, CDCl$_3$) δ 26.40, 29.27, 31.00, 35.74, 40.32, 115.90 (d, J=22.0 Hz), 118.76, 121.56, 124.94, 125.47, 125.74, 128.34 (d, J=7.7 Hz), 128.72, 132.61, 132.70, 133.16 (d, J=2.6 Hz), 139.76, 142.28, 149.45, 152.51, 166.10 (d, J=256.2 Hz), 190.18. MS (ESI) m/z: 447 [M-H]$^+$.

Example 10. N-(1,1-dimethyl-5-phenyl-pentyl)-7-(4-methoxyphenyl)-2-oxo-1,3-benzoxazole-3-carboxamide The title compound was obtained according to the General Procedure I (Method A), starting from Intermediate 8 (29 mg, 0.12 mmol) and Intermediate 24 (33 mg, 0.14 mmol). Colorless oil (18 mg, 33%). $^1$H NMR (400 MHz, CDCl$_3$) δ 1.40-1.46 (m, 2H), 1.47 (s, 6H), 1.65-1.74 (m, 2H), 1.82-1.89 (m, 2H), 2.67 (t, J=7.9 Hz, 2H), 3.90 (s, 3H), 7.03-7.07 (m, 2H), 7.14-7.22 (m, 3H), 7.24-7.29 (m, 2H), 7.33 (dd, J=8.0, 7.9 Hz, 1H), 7.39 (dd, J=8.0, 1.3 Hz, 1H), 7.67-7.72 (m, 2H), 8.03-8.08 (m, 2H). $^{13}$C NMR (101 MHz, CDCl$_3$) δ 23.69, 26.88, 31.70, 35.77, 40.30, 54.40, 55.38, 113.93, 114.30, 123.69, 123.92, 125.16, 125.63, 126.70, 128.24, 128.38, 128.65, 129.56, 138.60, 142.48, 148.20, 153.47, 159.74. MS (ESI) m/z: non-ionizable compound under routine conditions used.

Example 11. N-(1,1-dimethyl-5-phenyl-pentyl)-6-(4-fluorophenyl)-2-oxo-1,3-benzoxazole-3-carboxamide The title compound was obtained according to the General Procedure I (Method A), starting from Intermediate 3 (46 mg, 0.20 mmol) and Intermediate 24 (55 mg, 0.24 mmol). White solid (50 mg, 56%). $^1$H NMR (400 MHz, CDCl$_3$) δ 1.39-1.45 (m, 2H), 1.47 (s, 6H), 1.65-1.74 (m, 2H), 1.81-1.88 (m, 2H), 2.61-2.70 (m, 2H), 7.13-7.18 (m, 2H), 7.18-7.22 (m, 3H), 7.24-7.29 (m, 2H), 7.43 (d, J=1.6 Hz, 1H), 7.46 (dd, J=8.3, 1.6 Hz, 1H), 7.53-7.58 (m, 2H), 8.00 (s, 1H), 8.13 (d, J=8.3 Hz, 1H). $^{13}$C NMR (101 MHz, CDCl$_3$) δ 23.67, 26.85, 31.68, 35.76, 40.39, 54.46, 108.33, 115.84, 115.88 (d, J=21.5 Hz), 123.66, 125.65, 127.33, 128.25, 128.37, 128.72 (d, J=8.1 Hz), 136.08 (d, J=3.3 Hz), 137.20, 142.18, 142.45, 148.06, 153.43, 162.67 (d, J=247.5 Hz). MS (ESI) m/z: non-ionizable compound under routine conditions used.

Example 12. (±)-6-(4-fluorophenyl)-N-(1-methyl-5-phenyl-pentyl)-2-oxo-1,3-benzoxazole-3-carboxamide The title compound was obtained according to the General Procedure I (Method A), starting from Intermediate 3 (50 mg, 0.22 mmol) and Intermediate 21 (70 mg, 0.33 mmol). White powder (15 mg, 16%; 26% brsm). $^1$H NMR (400 MHz, CDCl$_3$) δ 1.28 (d, J=6.6 Hz, 3H), 1.40-1.50 (m, 2H), 1.58-1.72 (m, 4H), 2.63 (t, J=7.7 Hz, 2H), 3.98-4.11 (m, 1H), 7.11-7.19 (m, 5H), 7.22-7.28 (m, 2H), 7.41 (d, J=1.6 Hz, 1H), 7.44 (dd, J=8.3, 1.7 Hz, 1H), 7.53 (ddd, J=8.3, 5.2, 2.6 Hz, 2H), 7.87 (d, J=7.8 Hz, 1H), 8.10 (d, J=8.3 Hz, 1H). $^{13}$C NMR (101 MHz, CDCl$_3$) δ 21.03, 25.71, 31.32, 35.91, 36.64, 46.86, 108.54, 115.91 (d, J=3.3 Hz), 116.14, 123.90, 125.83, 128.11, 128.41, 128.52, 128.87 (d, J=8.1 Hz), 137.48, 141.97, 142.40, 142.51, 149.21, 153.35, 162.83 (d, J=247.7 Hz). MS (ESI) m/z: non-ionizable compound under routine conditions used.

Example 13. N-(3-butoxypropyl)-6-(4-fluorophenyl)-2-oxo-1,3-benzoxazole-3-carboxamide The title compound was obtained according to the General Procedure I (Method A), starting from Intermediate 3 (50 mg, 0.22 mmol) and the commercial 3-butoxypropyl amine (0.051 mL, 0.33 mmol). White powder (42 mg, 49%; 72% brsm). $^1$H NMR (400 MHz, CDCl$_3$) δ 0.93 (t, J=7.4 Hz, 3H), 1.31-1.46 (m, 2H), 1.50-1.67 (m, 2H), 1.82-2.03 (m, 2H), 3.45 (t, J=6.7 Hz, 2H), 3.52-3.61 (m, 4H), 7.10-7.19 (m, 2H), 7.39 (d, J=1.7 Hz, 1H), 7.43 (dd, J=8.3, 1.7 Hz, 1H), 7.48-7.58 (m, 2H), 8.10 (d, J=8.3 Hz, 1H), 8.28 (t, J=5.4 Hz, 1H). $^{13}$C NMR (101 MHz, CDCl$_3$) δ 14.08, 19.50, 29.45, 31.79, 38.58, 68.86, 71.31, 108.53, 115.87 (d, J=9.2 Hz), 116.13, 123.85, 127.38, 128.76 (d, J=9.2 Hz), 137.43, 142.39, 142.42, 149.85, 153.11, 162.80 (d, J=247.2 Hz). MS (ESI) m/z: 387 [M-H]$^+$, 309 [M-Na]$^+$.

Example 14. 5-chloro-7-(4-fluorophenyl)-2-oxo-N-(5-phenylpentyl)-1,3-benzoxazole-3-carboxamide The title compound was obtained according to the General Procedure I (Method A), starting from Intermediate 13 (126 mg, 0.52 mmol) and Intermediate 15 (155 mg, 0.78 mmol). White powder (42 mg, 18%). $^1$H NMR (400 MHz, CDCl$_3$) δ 1.38-1.50 (m, 2H), 1.62-1.78 (m, 4H), 2.58-2.72 (m, 2H), 3.32-3.58 (m, 2H), 7.14-7.23 (m, 5H), 7.24-7.30 (m, 2H), 7.36 (d, J=2.2 Hz, 1H), 7.63-7.70 (m, 2H), 8.00 (t, J=5.4 Hz, 1H), 8.11 (d, J=2.2 Hz, 1H). $^{13}$C NMR (101 MHz, CDCl$_3$) δ 26.52, 29.39, 31.11, 35.87, 40.48, 114.88, 116.22 (d, J=21.9 Hz), 124.02, 124.40, 125.86, 128.43, 128.51, 129.24 (d, J=3.2 Hz), 129.37, 130.27 (d, J=8.5 Hz), 131.12, 137.32, 142.41, 149.41, 152.94, 163.22 (d, J=249.6 Hz). MS (ESI) m/z: non-ionizable compound under routine conditions used.

Example 15. 5-(4-fluorophenyl)-2-oxo-N-(4-phenyl-sulfanylbutyl)-1,3-benzoxazole-3-carboxamide The title compound was obtained according to the General Procedure I (Method A), starting from Intermediate 4 (34 mg, 0.15 mmol) and Intermediate 28 (39 mg, 0.18 mmol). White solid (12 mg, 18%). $^1$H NMR (400 MHz, CDCl$_3$) δ 1.73-1.88 (m, 4H), 3.00 (t, J=6.8 Hz, 2H), 3.44-3.51 (m, 2H), 7.12-7.21 (m, 3H), 7.26-7.33 (m, 3H), 7.34-7.39 (m, 2H), 7.43 (dd, J=8.4, 1.7 Hz, 1H), 7.53-7.60 (m, 2H), 8.11 (t, J=4.9 Hz, 1H), 8.30 (d, J=1.6 Hz, 1H). $^{13}$C NMR (101 MHz, CDCl$_3$) δ 26.29, 28.53, 33.31, 39.79, 110.04, 114.27, 115.75 (d, J=21.5 Hz), 123.37, 126.02, 128.47, 128.90, 128.93 (d, J=6.4 Hz), 129.38, 136.21, 136.37 (d, J=2.9 Hz), 137.85, 141.12, 149.85, 153.24, 162.63 (d, J=247.0 Hz). MS (ESI) m/z: non-ionizable compound under routine conditions used.

Example 16. N-[4-(benzenesulfonyl)butyl]-5-(4-fluorophenyl)-2-oxo-1,3-benzoxazole-3-carboxamide The title compound was obtained according to the General Procedure I (Method A), starting from Intermediate 4 (34 mg, 0.15 mmol) and Intermediate 30 (45 mg, 0.18 mmol). White solid (25 mg, 36%). $^1$H NMR (400 MHz, CDCl$_3$) δ 1.73-1.91 (m, 4H), 3.19 (d, J=7.6 Hz, 2H), 3.42-3.49 (m, 2H), 7.11-7.19 (m, 2H), 7.31 (d, J=8.4 Hz, 1H), 7.43 (dd, J=8.4, 1.8 Hz, 1H), 7.53-7.60 (m, 4H), 7.62-7.67 (m, 1H), 7.91-7.96 (m, 2H), 8.11 (t, J=5.6 Hz, 1H), 8.25 (d, J=1.7 Hz, 1H). $^{13}$C NMR (101 MHz, CDCl$_3$) δ 20.09, 28.20, 39.41, 55.62, 110.09, 114.22, 115.78 (d, J=21.5 Hz), 123.47, 128.06, 128.35, 128.92 (d, J=8.2 Hz), 129.32, 133.75, 136.34 (d, J=3.1 Hz), 137.88, 138.98, 141.11, 149.91, 153.19, 162.65 (d, J=247.2 Hz). MS (ESI) m/z: 469 [M-H]$^+$.

Example 17. (±)-N-[4-(benzenesulfinyl)butyl]-6-(4-fluorophenyl)-2-oxo-1,3-benzoxazole-3-carboxamide The title compound was obtained according to the General Procedure I (Method A), starting from Intermediate 3 (34 mg, 0.15 mmol) and Intermediate 29 (42 mg, 0.18 mmol). White solid (18 mg, 27%). $^1$H NMR (400 MHz, CDCl$_3$) δ 1.71-1.98 (m, 4H), 2.82-2.95 (m, 2H), 3.44-3.51 (m, 2H), 7.14-7.19 (m, 2H), 7.43 (d, J=1.5 Hz, 1H), 7.46 (dd, J=8.2, 1.7 Hz, 1H), 7.50-7.57 (m, 5H), 7.65 (dd, J=8.2, 1.5 Hz, 2H), 8.07-8.08 (m, 1H), 8.09 (d, J=8.3 Hz, 1H). $^{13}$C NMR (101 MHz, CDCl$_3$) δ 19.46, 28.60, 39.64, 56.41, 108.47, 115.66, 115.91 (d, J=21.5 Hz), 123.81, 124.00, 127.04, 128.72 (d, J=8.1 Hz), 129.26, 131.02, 135.98 (d, J=3.0 Hz), 137.50, 142.25, 143.67, 149.75, 153.12, 162.70 (d, J=247.3 Hz). MS (ESI) m/z: 453 [M-H]$^+$.

Exemplary compounds according to the present invention are reported in the following Table 1.

TABLE 1

Exemplified compounds of the invention

| Example | Structure | Formula | MW | Name |
|---|---|---|---|---|
| 1 | 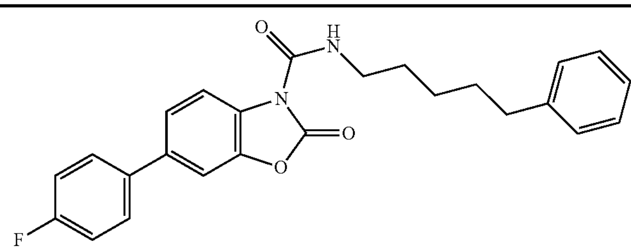 | $C_{25}H_{23}FN_2O_3$ | 418.5 | 6-(4-fluorophenyl)-2-oxo-N-(5-phenylpentyl)-1,3-benzoxazole-3-carboxamide |
| 2 | 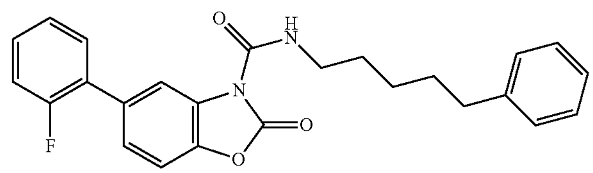 [SMILES: O=C(NCCCCCc1ccccc1)n1c(=O)oc2ccc(-c3ccccc3F)cc21] | $C_{25}H_{23}FN_2O_3$ | 418.5 | 6-(2-fluorophenyl)-2-oxo-N-(5-phenylpentyl)-1,3-benzoxazole-3-carboxamide |
| 3 | 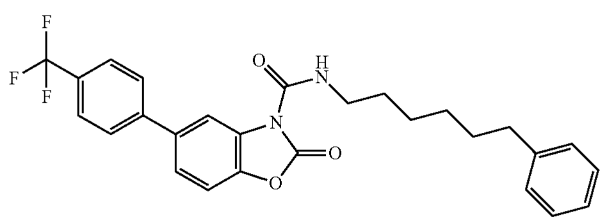 [SMILES: O=C(NCCCCCCc1ccccc1)n1c(=O)oc2ccc(-c3ccc(C(F)(F)F)cc3)cc21] | $C_{27}H_{25}F_3N_2O_3$ | 482.5 | 2-oxo-N-(6-phenylhexyl)-5-[4-(trifluoromethyl) phenyl]-1,3-benzoxazole-3-carboxamide |
| 4 | 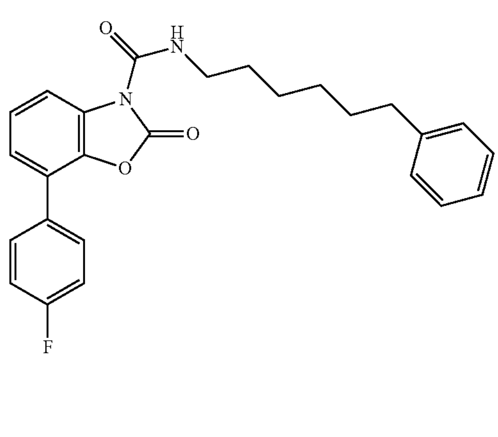 [SMILES: O=C(NCCCCCCc1ccccc1)n1c(=O)oc2c(-c3ccc(F)cc3)cccc21] | $C_{26}H_{25}FN_2O_3$ | 432.5 | 7-(4-fluorophenyl)-2-oxo-N-(6-phenylhexyl)-1,3-benzoxazole-3-carboxamide |

TABLE 1-continued

Exemplified compounds of the invention

| Example | Structure | Formula | MW | Name |
|---|---|---|---|---|
| 5 | 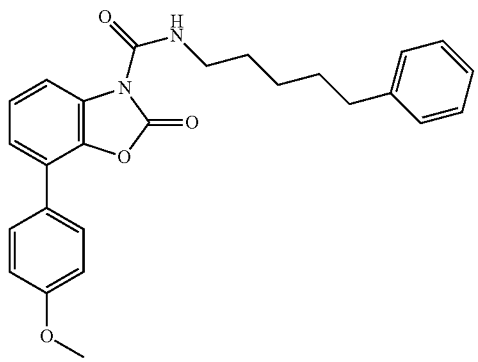 [SMILES: COc1ccc(-c2cccc3c2oc(=O)n3C(=O)NCCCCCc2ccccc2)cc1] | $C_{26}H_{26}N_2O_4$ | 430.5 | 7-(4-methoxyphenyl)-2-oxo-N-(5-phenylpentyl)-1,3-benzoxazole-3-carboxamide |
| 6 | 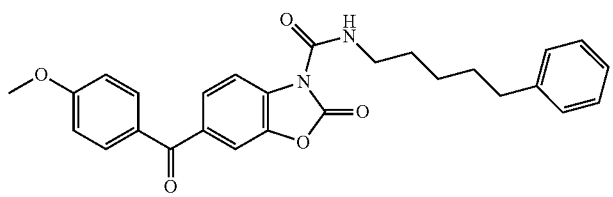 [SMILES: COc1ccc(C(=O)c2ccc3c(c2)oc(=O)n3C(=O)NCCCCCc2ccccc2)cc1] | $C_{27}H_{26}N_2O_5$ | 458.5 | 6-(4-methoxybenzoyl)-2-oxo-N-(5-phenylpentyl)-1,3-benzoxazole-3-carboxamide |
| 7 | 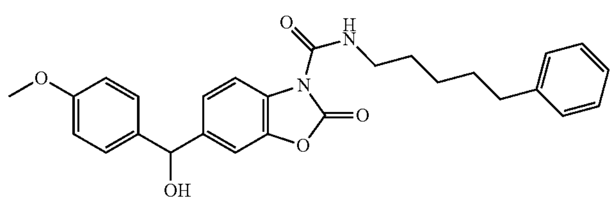 [SMILES: COc1ccc(C(O)c2ccc3c(c2)oc(=O)n3C(=O)NCCCCCc2ccccc2)cc1] | $C_{27}H_{28}N_2O_5$ | 460.5 | (±)-6-[hydroxy-(4-methoxyphenyl)methyl]-2-oxo-N-(5-phenylpentyl)-1,3-benzoxazole-3-carboxamide |
| 8 | 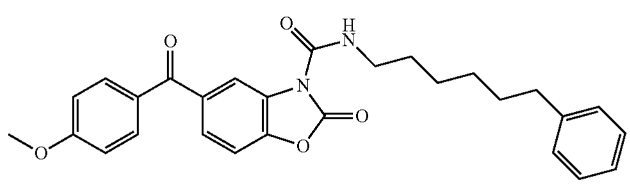 [SMILES: COc1ccc(C(=O)c2ccc3oc(=O)n(C(=O)NCCCCCCc4ccccc4)c3c2)cc1] | $C_{28}H_{28}N_2O_5$ | 472.5 | 5-(4-methoxybenzoyl)-2-oxo-N-(6-phenylhexyl)-1,3-benzoxazole-3-carboxamide |
| 9 | 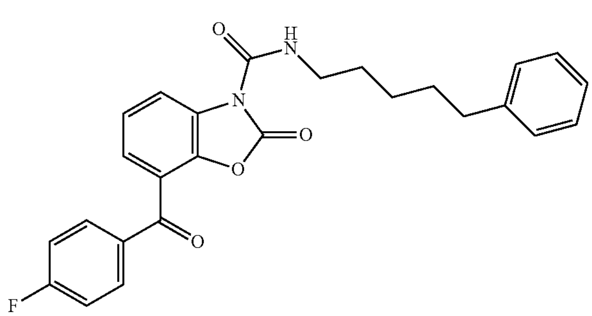 [SMILES: O=C(c1ccc(F)cc1)c1cccc2c1oc(=O)n2C(=O)NCCCCCc1ccccc1] | $C_{26}H_{23}FN_2O_4$ | 446.5 | 7-(4-fluorobenzoyl)-2-oxo-N-(5-phenylpentyl)-1,3-benzoxazole-3-carboxamide |

TABLE 1-continued

Exemplified compounds of the invention

| Example | Structure | Formula | MW | Name |
|---|---|---|---|---|
| 10 | 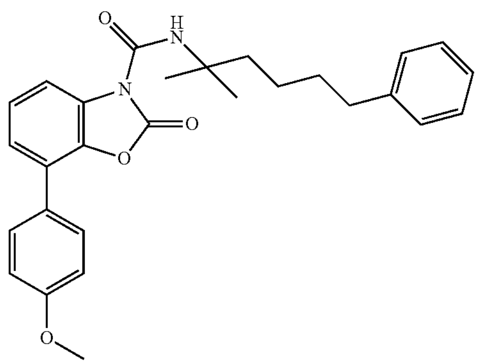 [SMILES: COc1ccc(-c2cccc3c2oc(=O)n3C(=O)NC(C)(C)CCCCc2ccccc2)cc1] | $C_{28}H_{30}N_2O_4$ | 458.6 | N-(1,1-dimethyl-5-phenyl-pentyl)-7-(4-methoxyphenyl)-2-oxo-1,3-benzoxazole-3-carboxamide |
| 11 | 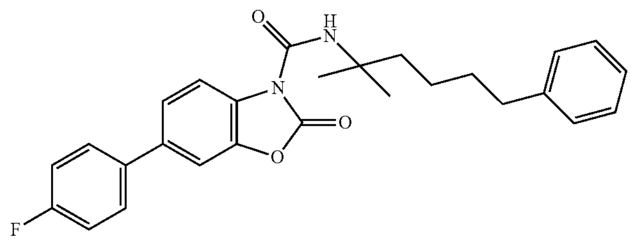 [SMILES: CC(C)(CCCCc1ccccc1)NC(=O)n1c(=O)oc2cc(-c3ccc(F)cc3)ccc21] | $C_{22}H_{22}FN_2O_3$ | 446.5 | N-(1,1-dimethyl-5-phenyl-pentyl)-6-(4-fluorophenyl)-2-oxo-1,3-benzoxazole-3-carboxamide |
| 12 | 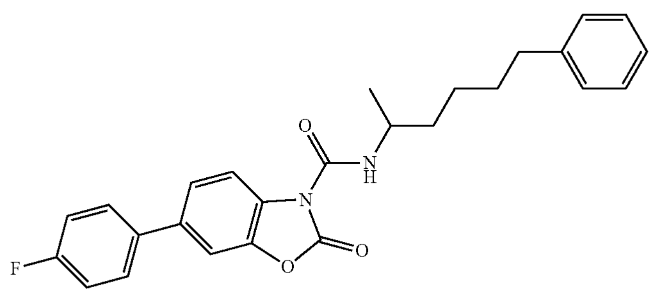 [SMILES: CC(CCCCc1ccccc1)NC(=O)n1c(=O)oc2cc(-c3ccc(F)cc3)ccc21] | $C_{26}H_{25}FN_2O_3$ | 432.5 | (±)-6-(4-fluorophenyl)-N-(1-methyl-5-phenyl-pentyl)-2-oxo-1,3-benzoxazole-3-carboxamide |
| 13 | 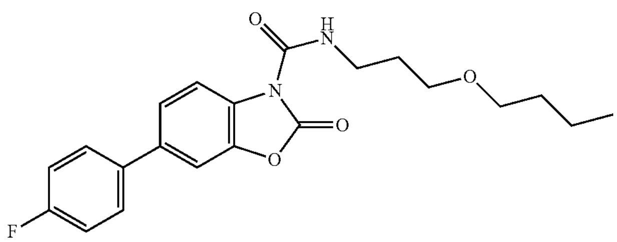 [SMILES: CCCCOCCCNC(=O)n1c(=O)oc2cc(-c3ccc(F)cc3)ccc21] | $C_{21}H_{23}FN_2O_4$ | 386.4 | N-(3-butoxypropyl)-6-(4-fluorophenyl)-2-oxo-1,3-benzoxazole-3-carboxamide |
| 14 | 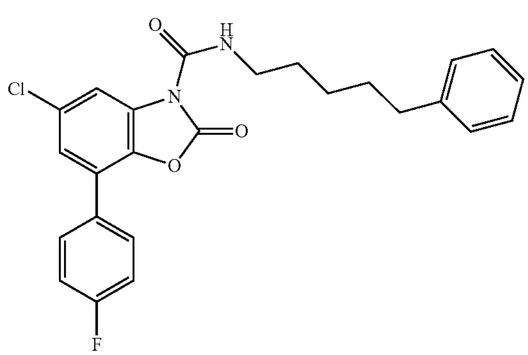 [SMILES: O=C(NCCCCCc1ccccc1)n1c(=O)oc2c(-c3ccc(F)cc3)cc(Cl)cc21] | $C_{25}H_{22}ClFN_2O_3$ | 452.9 | 5-chloro-7-(4-fluorophenyl)-2-oxo-N-(5-phenylpentyl)-1,3-benzoxazole-3-carboxamide |

TABLE 1-continued

Exemplified compounds of the invention

| Example | Structure | Formula | MW | Name |
|---|---|---|---|---|
| 15 | 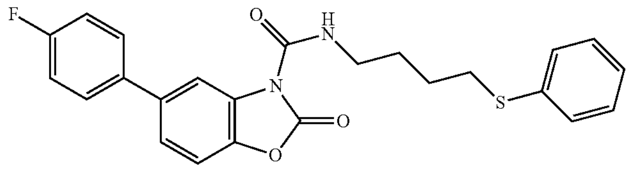 [SMILES: O=C(NCCCCSc1ccccc1)n1c(=O)oc2ccc(-c3ccc(F)cc3)cc21] | $C_{24}H_{21}FN_2O_3S$ | 436.5 | 5-(4-fluorophenyl)-2-oxo-N-(4-phenylsulfanylbutyl)-1,3-benzoxazole-3-carboxamide |
| 16 | 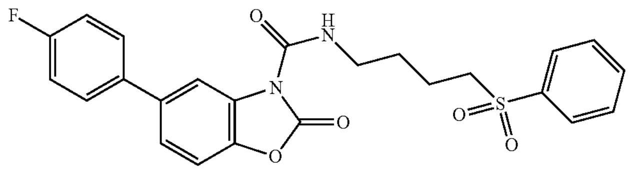 [SMILES: O=C(NCCCCS(=O)(=O)c1ccccc1)n1c(=O)oc2ccc(-c3ccc(F)cc3)cc21] | $C_{24}H_{21}FN_2O_5S$ | 468.5 | N-[4-(benzenesulfonyl) butyl]-5-(4-fluorophenyl)-2-oxo-1,3-benzoxazole-3-carboxamide |
| 17 | 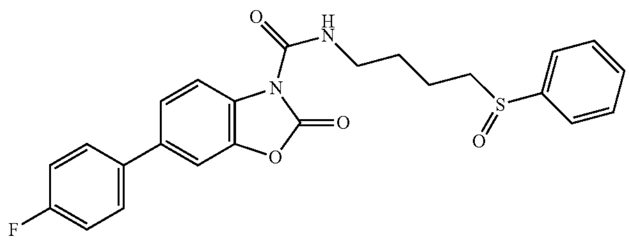 [SMILES: O=C(NCCCCS(=O)c1ccccc1)n1c(=O)oc2cc(-c3ccc(F)cc3)ccc21] | $C_{24}H_{21}FN_2O_4S$ | 452.5 | (±)-N-[4-(benzenesulfinyl) butyl]-6-(4-fluorophenyl)-2-oxo-1,3-benzoxazole-3-carboxamide |

TABLE 2

$IC_{50}$ values of selected compounds of the invention on human (hAC) acid ceramidase, via fluorescent-based in vitro assay

| Example | $IC_{50}$ (nM) ± SD | n |
|---|---|---|
| 1 | 75 ± 20 | 2 |
| 2 | 102 ± 33 | 2 |
| 3 | 111 ± 30 | 2 |
| 4 | 125 ± 79 | 3 |
| 6 | 26 ± 3 | 2 |
| 7 | 220 ± 70 | 2 |
| 8 | 46 ± 31 | 2 |
| 9 | 66 ± 15 | 2 |
| 13 | 132 ± 5 | 3 |
| 14 | 37 | 1 |
| 15 | 240 ± 58 | 2 |

COMPARATIVE EXAMPLE

Experimental evidence of lack of inhibitory activity of the compounds of the invention towards the molecular/biological targets (MAG-hydrolyzing enzymes including MGL and HSL and EL) of benzoxazol-2-one derivatives disclosed in U.S. Pat. No. 7,709,513 B2 as lipase and phospholipase inhibitors.

Premise

Compounds of Formula (I) (Ia), (Ib) of the invention are able to inhibit AC in vitro and in vivo, resulting in an increase in the levels of ceramides and a decrease in the levels of sphingosine and its bioactive metabolite sphingosine-1-phosphate.

Comparative Test

Specifically, the compound of Example 1 was tested for its ability to inhibit the hydrolytic degradation of diacylglycerols (DAG) and monoacylglycerols (MAG) in live mice. DAG and MAG hydrolysis is catalyzed by multiple serine lipases, including diacylglycerol lipase (DGL), monoacylglycerol lipase (MGL), hormone-sensitive lipase (HSL), and endothelial lipase. Thus, by monitoring the effects of compound of Example 1 on MAG-hydrolysing activity as well as DAG and MAG levels ex vivo, we gain important information as to the ability of the compound to interfere with those lipases in a physiologically relevant setting.

Systemic administration of compound of Example 1 (10 mg-kg$^{-1}$, intraperitoneal, i.p.) to mice did not cause inhibition of MAG-hydrolysing activity in fat and other body organs, including brain, liver and heart as illustrated in FIG. 1.

Figure 2:
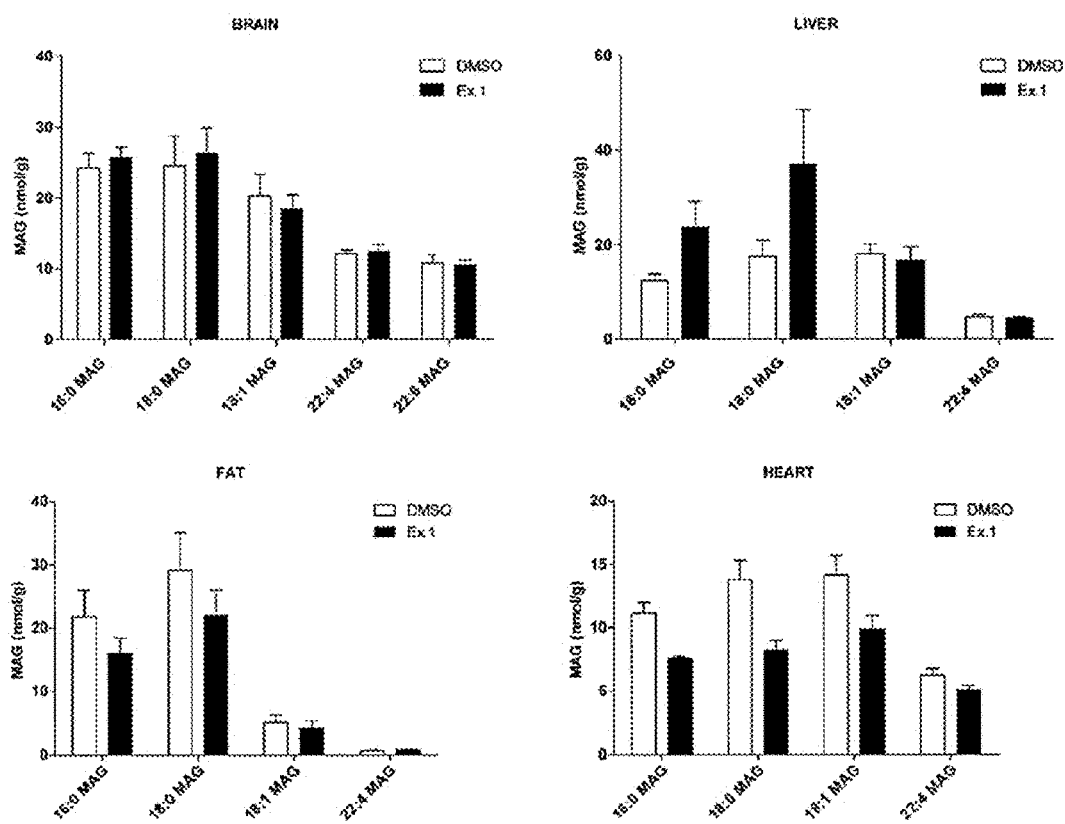
FIG. 2 shows the lack of effect of the compound of Example 1 on levels of various monoglycerides in brain, liver, fat and heart.

Specifically, FIG. 1 evidences the effect of Example 1 or vehicle (DMSO) on MGL activity in brain, liver, fat and heart. MAG-hydrolysing activity was measured 3 h after intraperitoneal injection of compound of Example 1 (10 mg-kg-1). Results are expressed as mean±s.e.m. (n=5). Furthermore, as shown in FIG. 2, the levels of the most representative MAGs in these tissues remained unchanged. The levels of MAGs were quantified after 3 hours after intraperitoneal injection of compound of Example 1 (10 mg-kg-1). Specifically, levels of 16:0 MAG, 18:0 MAG, 18:1 MAG, 22:4 MAG, 22:6 MAG were measured in the brain (a); levels of 16:0 MAG, 18:0 MAG, 18:1 MAG, 22:4 MAG were measured in the liver (b), in fat (c) and in the heart (d). Results are expressed as mean±s.e.m. (n=5).

These results demonstrate that compound of Example 1 has no inhibitory activity toward any MGL-hydrolysing enzymes in mice, including monoacylglycerol lipase (MGL), hormone-sensitive lipase (HSL), and endothelial lipase.

Methods

Procedure for Lipid Extraction

We homogenized tissue samples (20-30 mg) in methanol (1 mL) containing deuterium-labeled 2-AG (500 pmol) as internal standard (Cayman, Ann Arbor, Mich.). We extracted lipids with chloroform (2 mL) and water (1 mL). The organic phases were dried in a stream of $N_2$, reconstituted in chloroform (2 mL) and fractionated by open-bed silica gel column chromatography as described. The eluded fraction containing 2-AG and anandamide were dried under $N_2$, and residues were suspended in chloroform/methanol (1:3, vol:vol; 100 μL). Analyses were conducted using a liquid chromatography mass spectrometry (LC-MS) apparatus consisting of an Agilent 1100 system and 1946D mass spectrometer detector equipped with ESI interface (Agilent Technologies, Santa Clara, Calif., USA).

Procedure for LC-MS Based Assay

Tissue was homogenized in ice-cold Tris-HCl (50 mM, pH7.5, 10 vol) containing sucrose (0.32 M). Homogenates were centrifuged at 1,000×g for 10 min, and the supernatants (5 μg of protein) were incubated at 37° C. for 30 min in Tris-HCl (50 mM, pH 7.5, 0.5 mL) containing 10 μM oleoylglycerol (Sigma-Aldrich, St. Louis, Mo.). Reactions were stopped by adding 1.5 mL of chloroform/methanol (2:1, v:v) containing 17:0 fatty acid (m/z=269) as an internal standard. After centrifugation at 1,000×g at 4° C. for 10 min, the organic layers were collected and dried under $N_2$. The residues were suspended in 100 μL of chloroform/methanol (1:3, v:v) and analyzed by LC-MS.

The invention claimed is:

1. A compound of Formula (I) or a pharmaceutically acceptable salt thereof

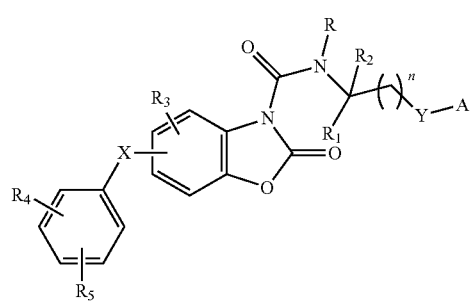

Formula (I)

wherein:

X is a bond, CO, CH(OH) or $CH_2$ group; wherein X can be attached to any position of the ring to which it is connected;

R, $R_1$ and $R_2$ are independently hydrogen or linear or branched $C_{1-6}$ alkyl;

n is an integer from 1 to 6;

A is a linear or branched $C_{1-9}$ alkyl, $C_{2-9}$ alkenyl or $C_{2-9}$ alkynyl group or a group:

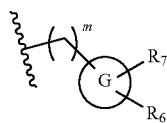

wherein:

m is 0 or an integer from 1 to 6;

G is a 3-10 membered saturated or unsaturated, aromatic or heteroaromatic, single or fused ring comprising up to three heteroatoms selected from N, O, and S; and $R_6$ and $R_7$ are as defined below;

$R_3$ is hydrogen, halogen, linear or branched $C_{1-6}$ alkyl, $C_{1-6}$ alkoxy or OH; wherein $R_3$ can be attached to any position of the ring to which it is connected;

$R_4$ and $R_5$ are independently selected from the group consisting of hydrogen, halogen, linear or branched $C_{1-6}$ alkyl, $C_{1-6}$ alkoxy, hydroxy $C_{1-6}$ alkyl, OH, CN, $NO_2$, fluoro $C_{1-6}$ alkyl, fluoro $C_{1-6}$ alkoxy, $COOR_8$, $CONR_9R_{10}$, $SO_2NR_9R_{10}$, and $SO_2R_{11}$;

$R_6$ and $R_7$ are independently selected from the group consisting of hydrogen, halogen, linear or branched $C_{1-6}$ alkyl, optionally substituted $C_{3-6}$ cycloalkyl, $C_{1-6}$ alkoxy, hydroxy $C_{1-6}$ alkyl, OH, CN, $NO_2$, fluoro $C_{1-6}$ alkyl, fluoro $C_{1-6}$ alkoxy, optionally substituted aryl or heteroaryl, $COOR_8$, $CONR_9R_{10}$, $SO_2NR_9R_{10}$, and $SO_2R_{11}$;

wherein $R_4$, $R_5$, $R_6$ and $R_7$ can be attached to any position of the ring to which they are connected;

Y is a bond or a heteroatom selected from the group consisting of O, S, SO, $SO_2$ and $NR_{12}$; and $R_8$, $R_9$, $R_{10}$, $R_{11}$ and $R_{12}$ are independently selected from the group consisting of hydrogen and linear or branched $C_{1-6}$ alkyl;

with the proviso that when Y is a bond, n+m is ≥4 and A is a group

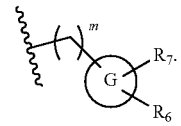

2. A compound according to claim 1 wherein:

X is a bond, CO, or CH(OH);

R is hydrogen;

$R_1$ and $R_2$ are independently hydrogen or linear or branched $C_{1-6}$ alkyl;

n is an integer from 1 to 6;

A is a linear $C_{1-6}$ alkyl or a group

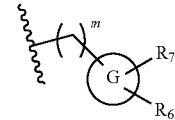

wherein m is an integer from 1 to 6;

G is an aryl selected from naphthyl or phenyl $(C_3-C_{10})$cycloalkyl, or a heteroaryl which is pyridyl, thiophenyl, pyrimidinyl, furyl, or indolyl;

$R_3$ is hydrogen or halogen;

$R_4$ and $R_5$ are independently selected from the group consisting of hydrogen, halogen, linear or branched $C_{1-6}$ alkyl, $C_{1-6}$ alkoxy, OH, CN, $NO_2$, $CF_3$, and hydroxy $C_{1-6}$ alkyl;

$R_6$ and $R_7$ are independently selected from the group consisting of hydrogen, halogen, linear or branched $C_{1-6}$ alkyl, $C_{1-6}$ alkoxy, hydroxy $C_{1-6}$ alkyl, OH, CN, $NO_2$, and $CF_3$;

Y is a bond or heteroatom selected from the group consisting of O, S, SO, and $SO_2$;

with the proviso that when Y is a bond, A is a group

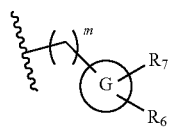

and n+m is ≥4.

3. A compound according to claim 1 having the Formula (Ia),

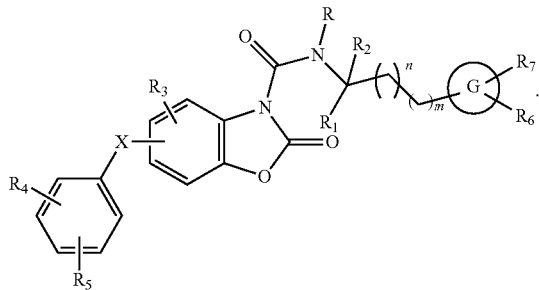

Formula (Ia)

4. A compound according to claim 3 having Formula (Ia) wherein:

X is a bond, CO, or CH(OH); wherein X can be attached to any position of the ring to which it is connected;

R is hydrogen;

$R_1$ and $R_2$ are independently hydrogen or methyl;

n is an integer from 2 to 4;

m is an integer from 2 to 4;

G is phenyl, thiophenyl, pyridyl, naphthyl or $C_{3-7}$ cycloalkyl;

$R_3$ is hydrogen or chlorine; wherein $R_3$ can be attached to any position of the ring to which it is connected;

$R_4$ is hydrogen;

$R_5$ is independently selected from the group consisting of halogen, Me, Et, MeO, EtO, OH, CN, $NO_2$, and $CF_3$; and $R_6$ and $R_7$ are independently selected from the group consisting of hydrogen, halogen, Me, Et, MeO, EtO, OH, CN, $NO_2$, and $CF_3$;

wherein $R_4$, $R_5$, $R_6$ and $R_7$ can be attached to any position of the ring to which they are connected.

5. A compound according to claim 1 having Formula (Ib)

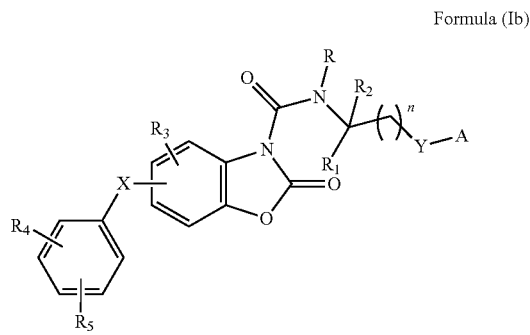

Formula (Ib)

wherein:

Y is a heteroatom selected from the group consisting of O, S, SO, $SO_2$ and $NR_{12}$; wherein $R_{12}$ is hydrogen or linear or branched $C_{1-6}$ alkyl.

6. A compound of Formula (Ib) according to claim 5, wherein

X is a bond, CO, or CH(OH); wherein X can be attached to any position of the ring to which it is connected;

R is hydrogen;

$R_1$ and $R_2$ are independently hydrogen or Me;

n is an integer from 1 to 4;

m is 0 or an integer from 1 to 4;

G is phenyl, thiophenyl, pyridyl, naphthyl or $C_{3-7}$ cycloalkyl;

$R_3$ is hydrogen or chlorine; wherein $R_3$ can be attached to any position of the ring to which it is connected;

$R_4$ is hydrogen;

$R_5$ is independently selected from the group consisting of halogen, Me, Et, MeO, EtO, OH, CN, $NO_2$, and $CF_3$; and $R_6$ and $R_7$ are independently selected from the group consisting of hydrogen, halogen, Me, Et, MeO, EtO, OH, CN, $NO_2$, and $CF_3$;

wherein $R_4$, $R_5$, $R_6$ and $R_7$ can be attached to any position of the ring to which they are connected.

7. A pharmaceutical composition comprising the compound, or a pharmaceutically acceptable salt thereof, of claim 1 and a pharmaceutically acceptable carrier.

8. The pharmaceutical composition of claim 7 comprising an additional pharmaceutically active ingredient.

9. The pharmaceutical composition of claim 8 wherein the additional pharmaceutically active ingredient is an anticancer agent, an anti-inflammatory agent, an analgesic compound, an agent for treating pulmonary diseases, or mixtures thereof.

10. A pharmaceutical composition comprising the compound of claim 3 and a pharmaceutically acceptable carrier.

11. A pharmaceutical composition comprising the compound of claim 5 and a pharmaceutically acceptable carrier.

* * * * *